(12) United States Patent
Zuk, Jr.

(10) Patent No.: US 6,660,171 B2
(45) Date of Patent: Dec. 9, 2003

(54) HIGH CAPACITY GRAVITY FEED FILTER FOR FILTERING BLOOD AND BLOOD PRODUCTS

(76) Inventor: Peter Zuk, Jr., 258 Old Littleton Rd., Harvard, MA (US) 01451

( * ) Notice: Subject to any disclaimer, the term of this patent is extended or adjusted under 35 U.S.C. 154(b) by 127 days.

(21) Appl. No.: 09/818,108

(22) Filed: Mar. 27, 2001

(65) Prior Publication Data

US 2002/0008063 A1 Jan. 24, 2002

Related U.S. Application Data

(60) Provisional application No. 60/192,733, filed on Mar. 27, 2000.

(51) Int. Cl.$^7$ .................. B01D 37/00; B01D 29/00
(52) U.S. Cl. .......... 210/767; 210/435; 210/436; 210/456; 210/472; 210/650
(58) Field of Search .................. 210/650, 767, 210/321.6, 433.1, 435, 436, 446, 455, 456, 472, 477

(56) References Cited

U.S. PATENT DOCUMENTS

| | | | |
|---|---|---|---|
| 4,304,670 A | * 12/1981 | Watanabe et al. | 210/446 |
| 4,422,939 A | * 12/1983 | Sharp et al. | 210/445 |
| 4,963,260 A | * 10/1990 | Naoi et al. | 210/446 |
| 5,439,587 A | * 8/1995 | Stankowski et al. | 210/321.64 |
| 5,622,626 A | * 4/1997 | Matkovich et al. | 210/649 |
| 6,010,633 A | 1/2000 | Zuk et al. | 210/767 |
| 6,214,574 B1 | * 4/2001 | Kopf | 435/41 |
| 6,231,770 B1 | 5/2001 | Bormann et al. | 210/767 |
| 6,251,292 B1 | 6/2001 | Zuk | 210/767 |
| 6,274,055 B1 | 8/2001 | Zuk | 210/767 |

* cited by examiner

Primary Examiner—John Kim

(57) ABSTRACT

A high capacity gravity feed filter for filtering blood and blood products or the like includes a body having an inlet port, an outlet port, two filter wells, at least one filter element disposed in each of said filter wells, between the inlet port and outlet port so as to filter liquid which flows into the filtration device via the inlet port. The filter elements divide each of said filter wells into a first chamber and a second chamber. The device allows gases to vent the filtration device through the outlet port. The means may include a vertical channel within each of said second chambers. The filtration device allows air therein to be purged downstream into a receiving blood bag without the manipulation of the height of the filtration device or the receiving blood bag.

33 Claims, 32 Drawing Sheets

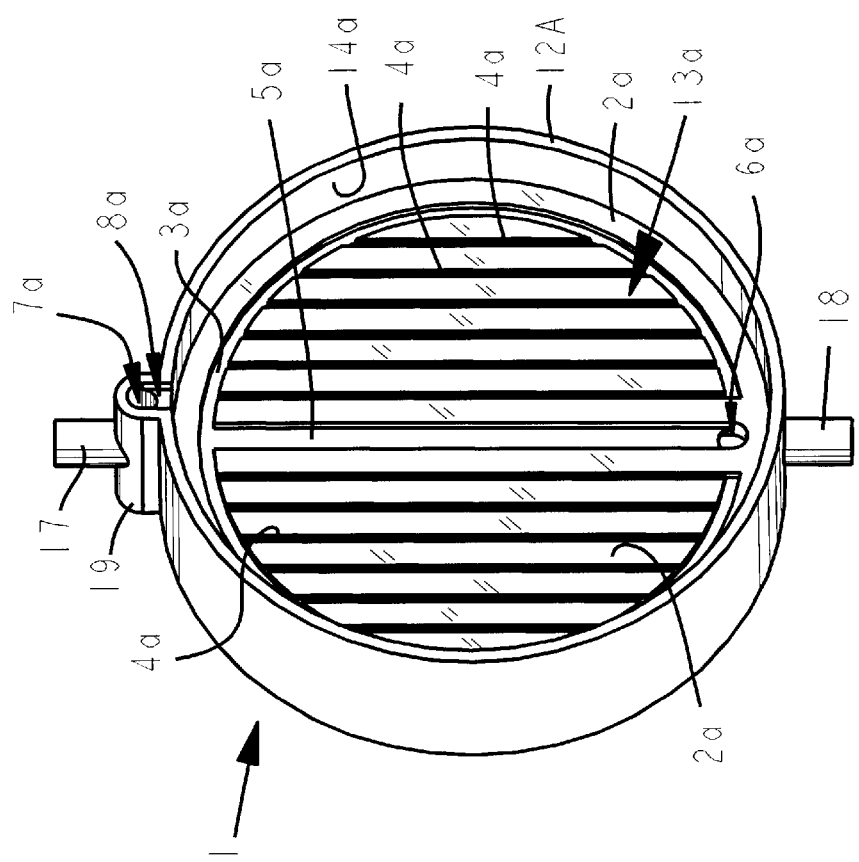
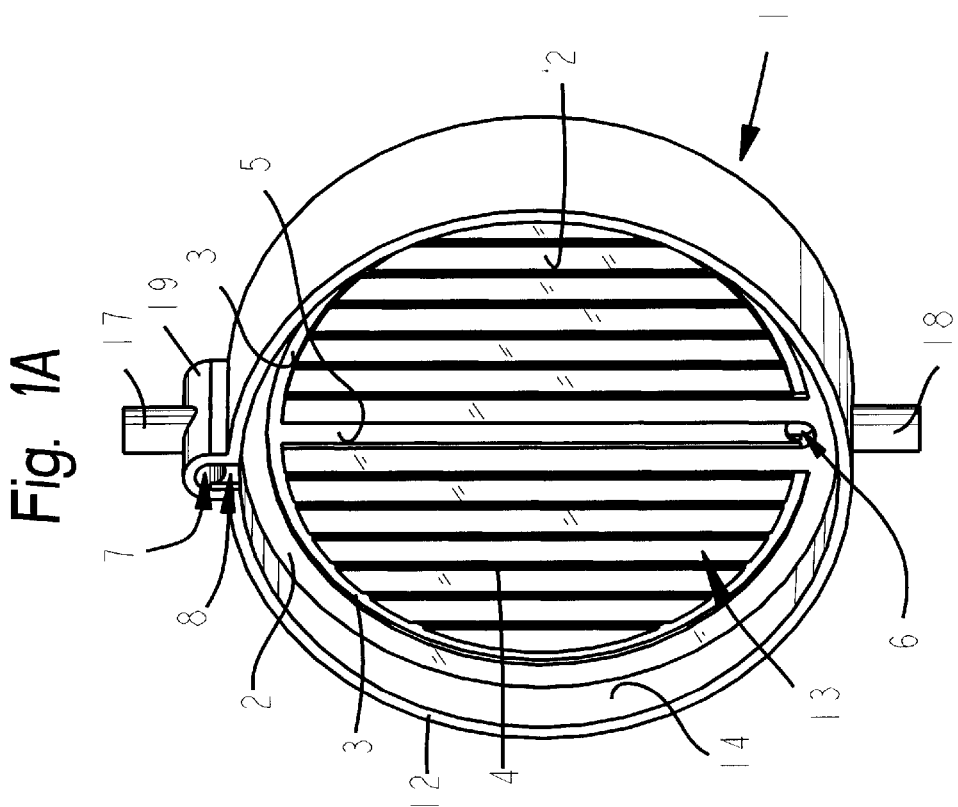

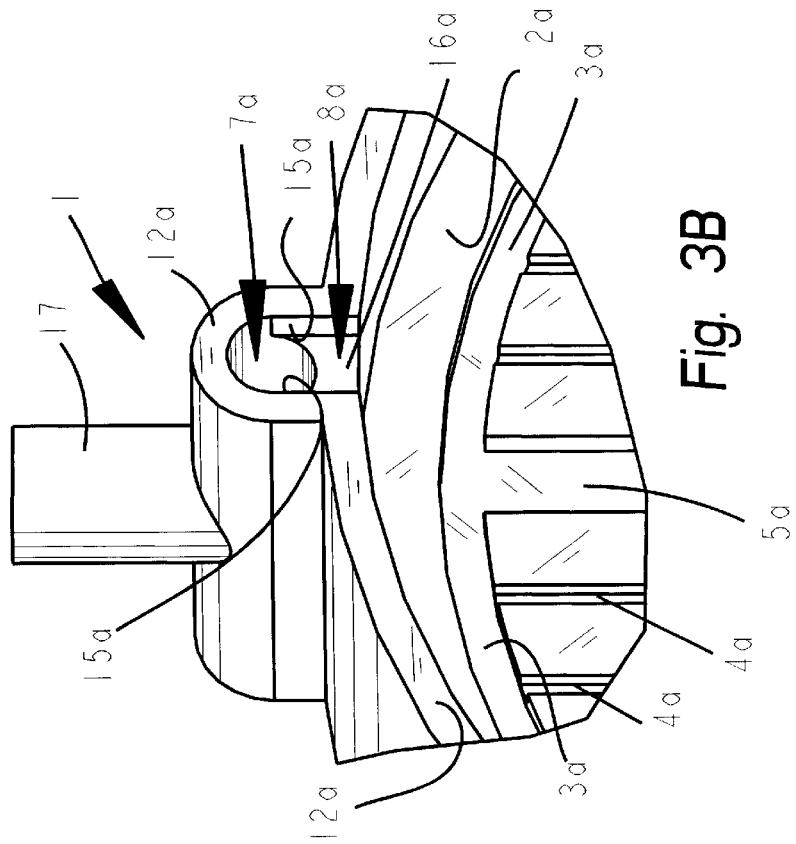
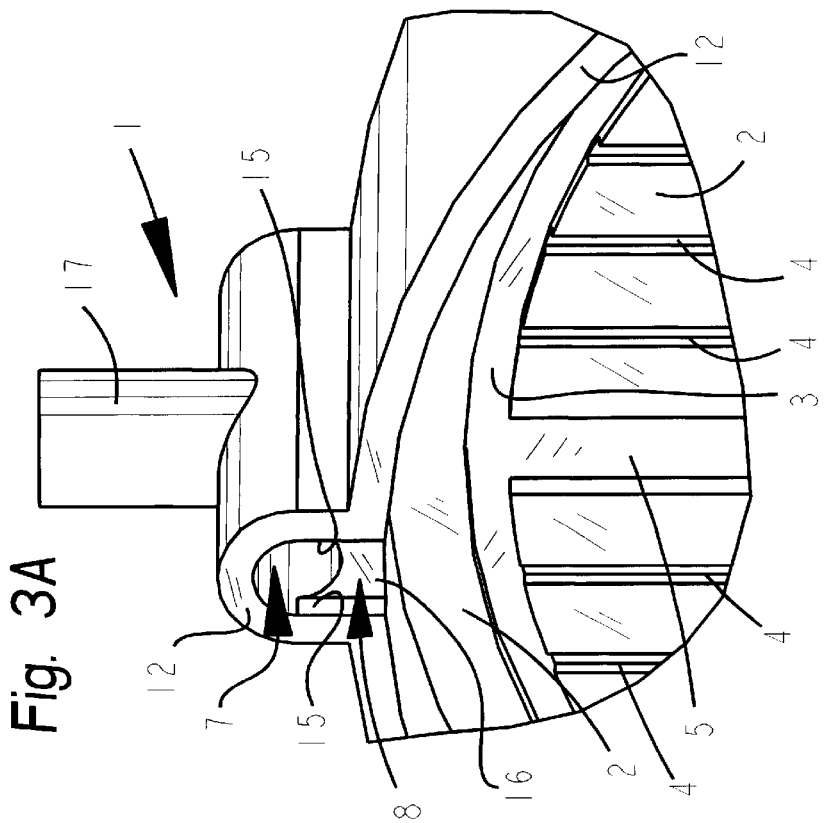
Fig. 3A
Fig. 3B

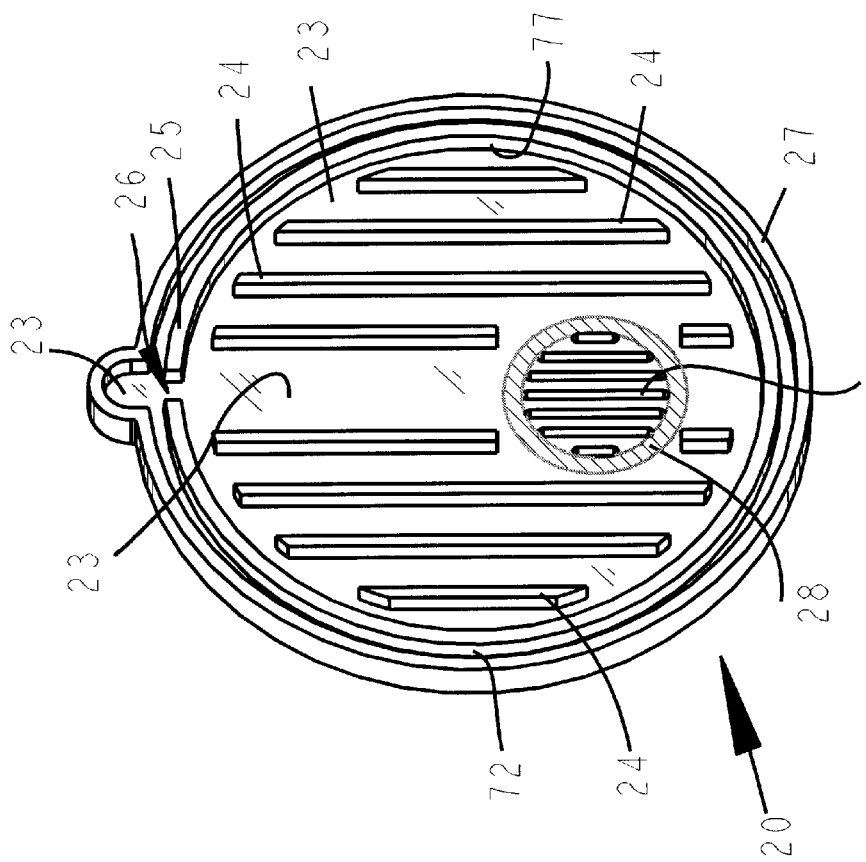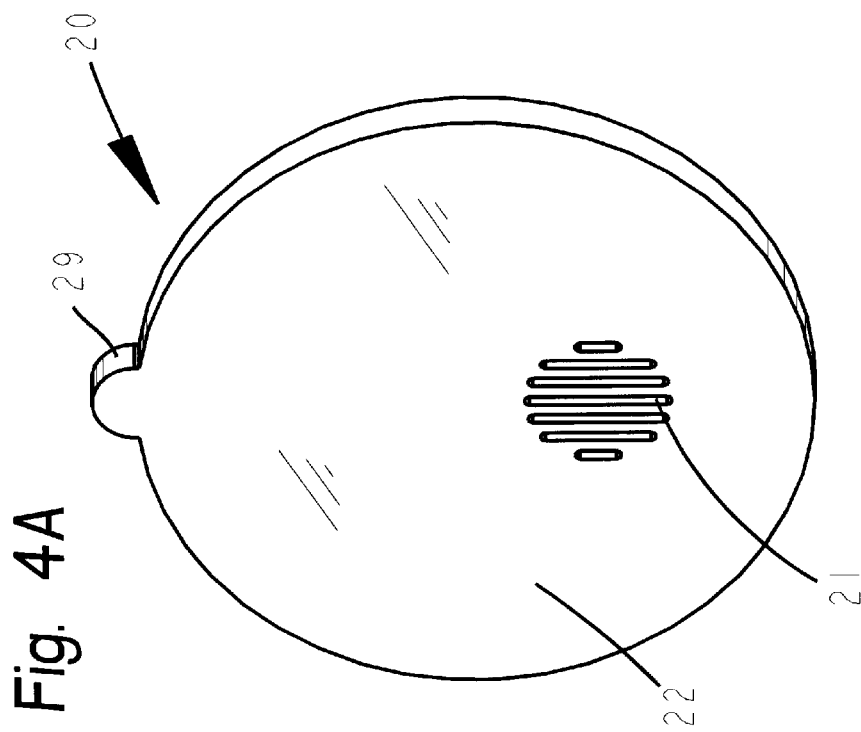

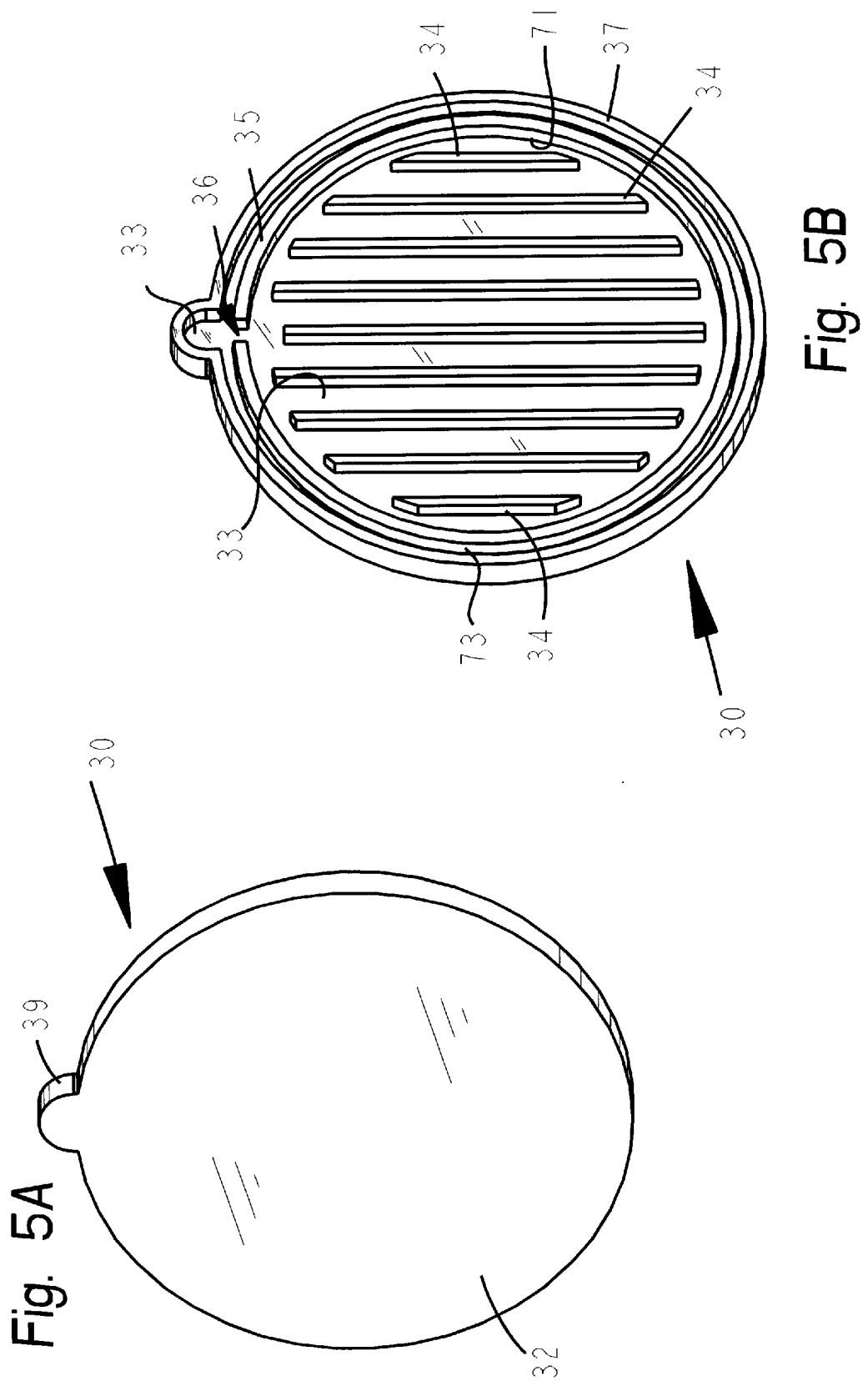

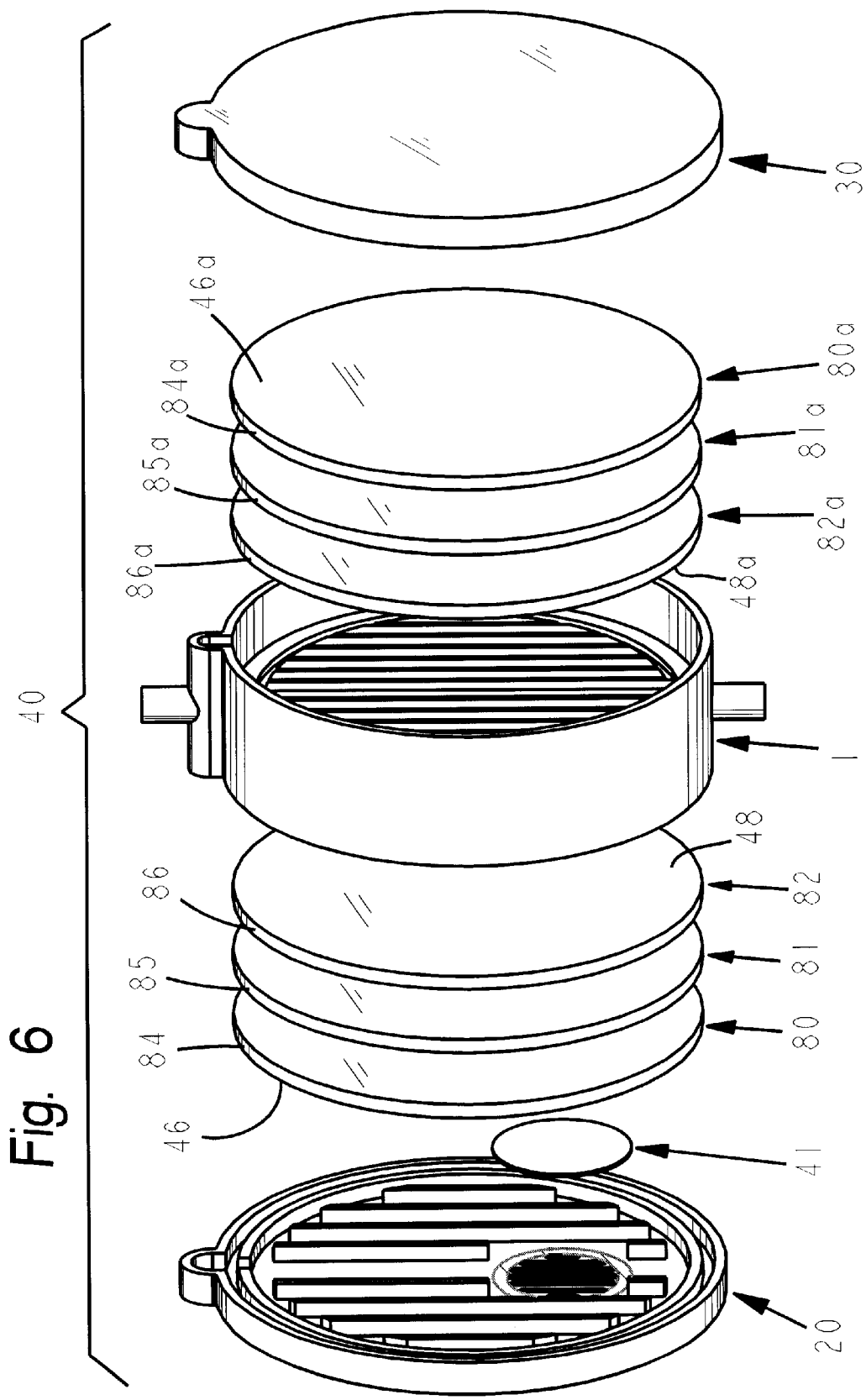

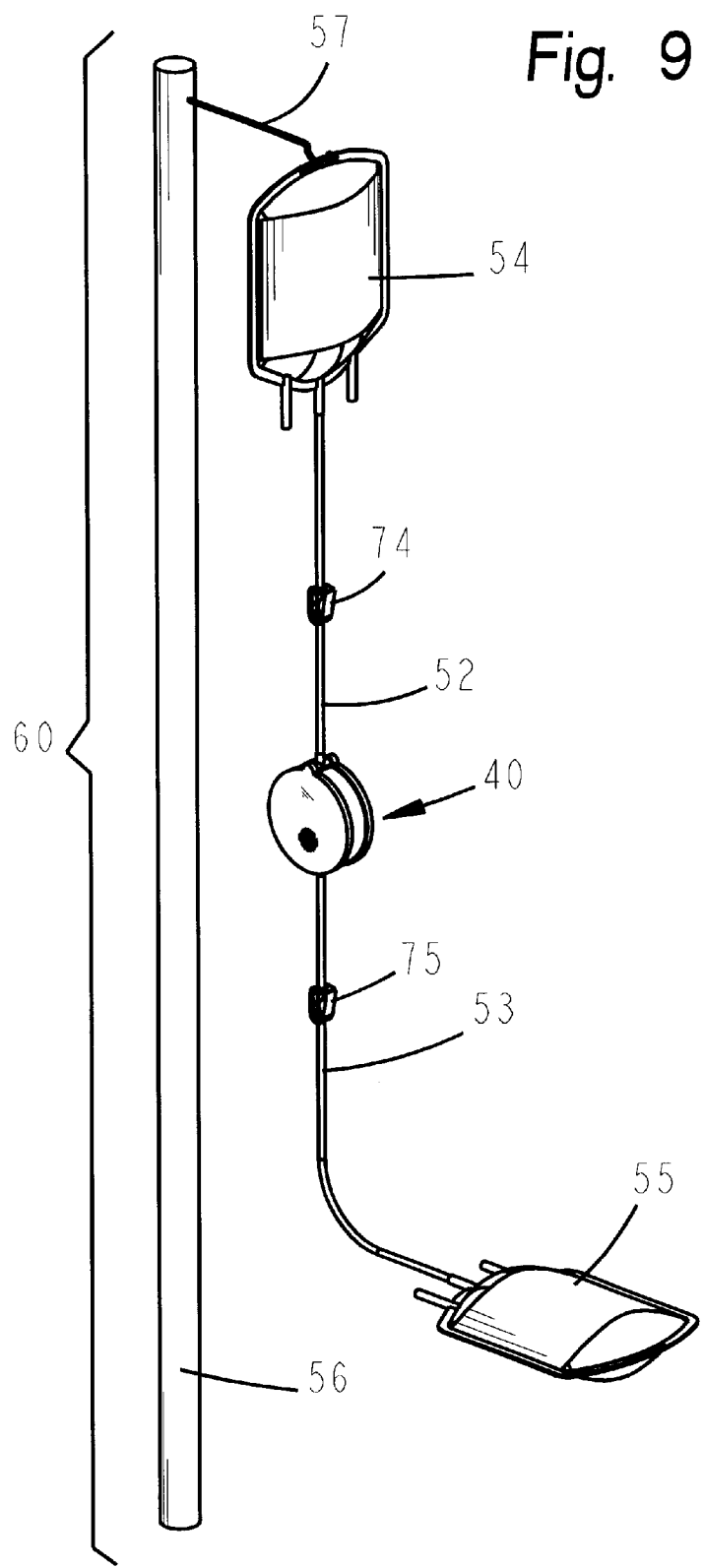

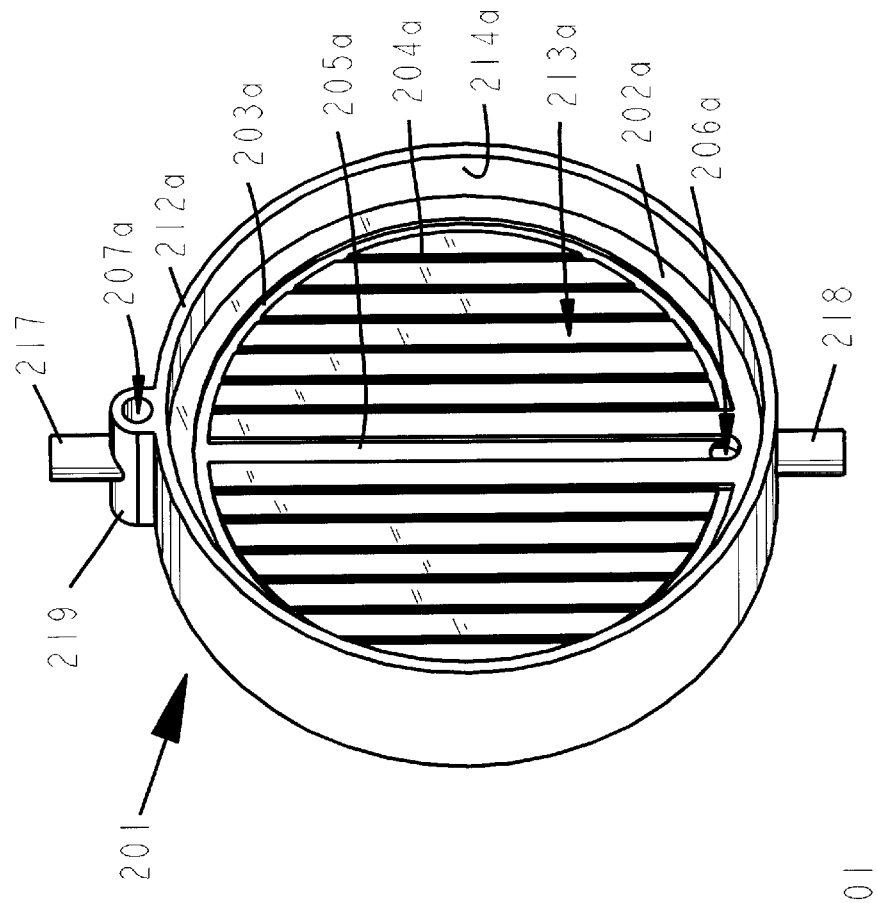
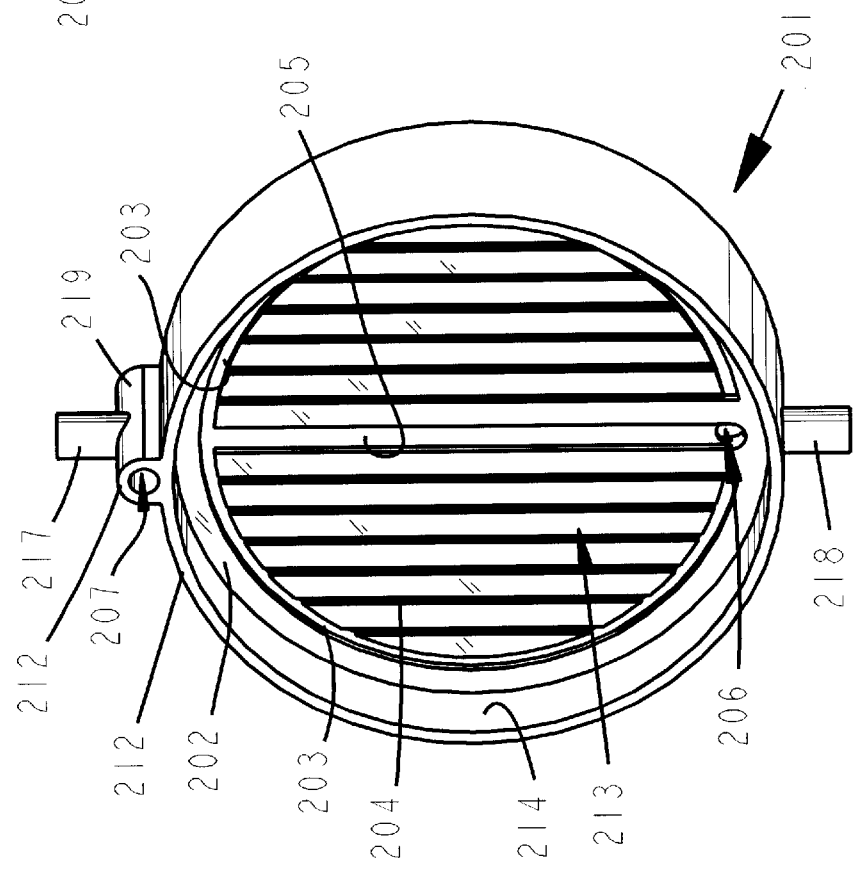

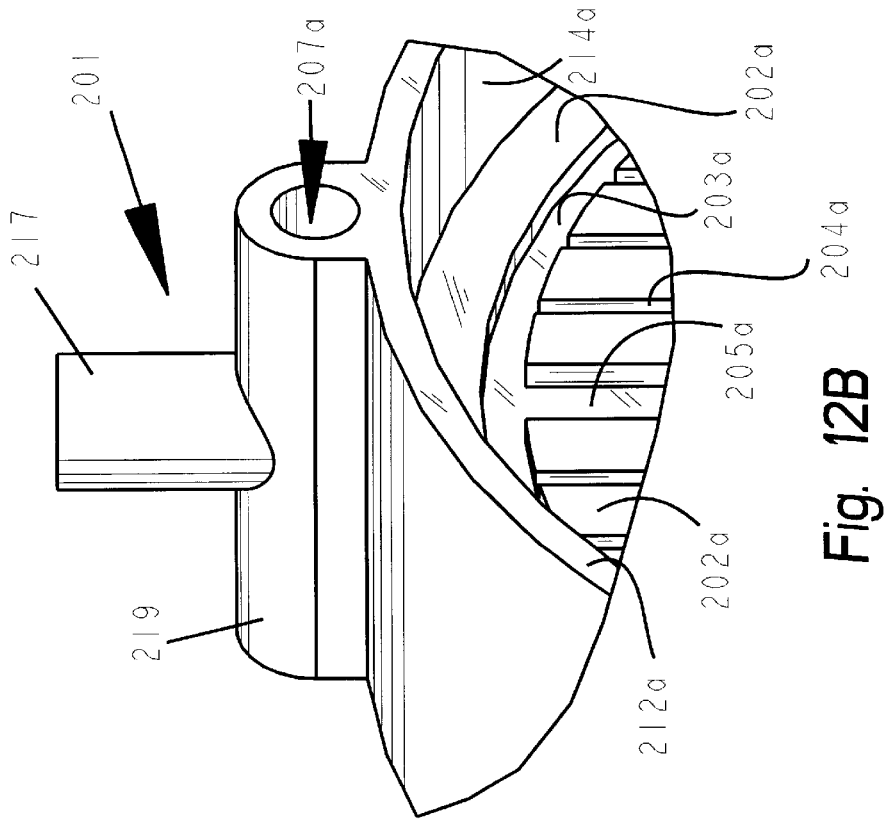
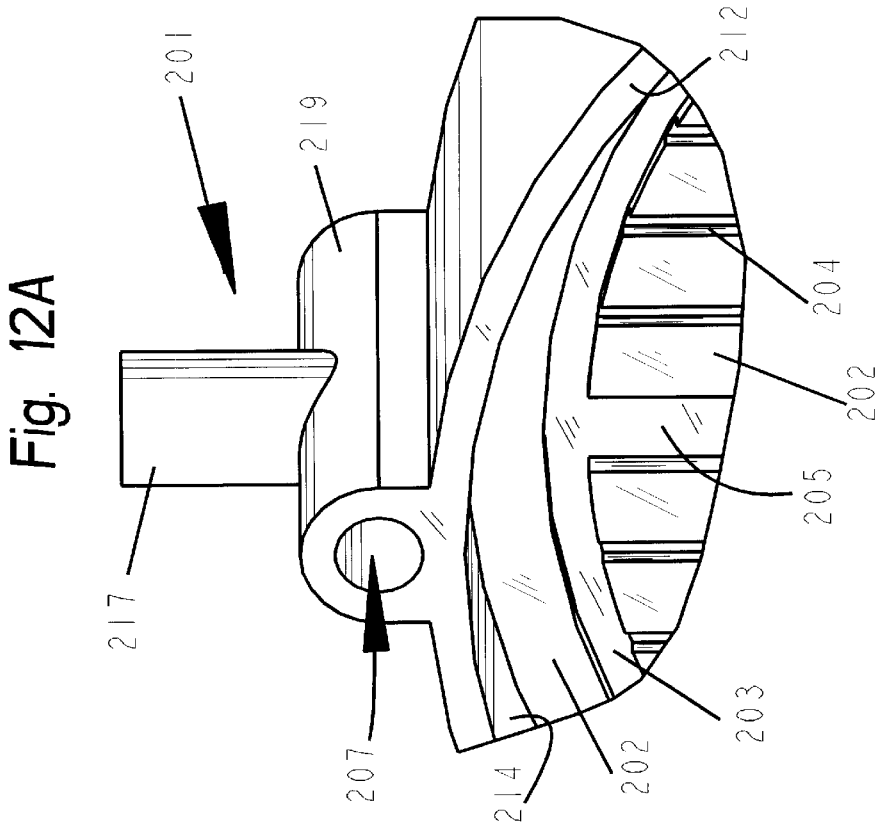

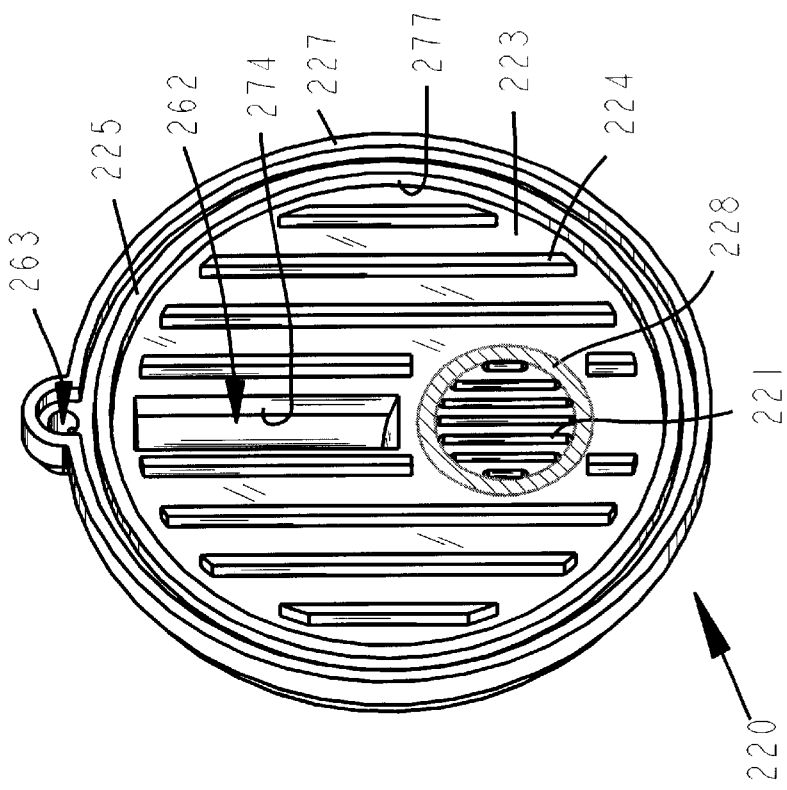
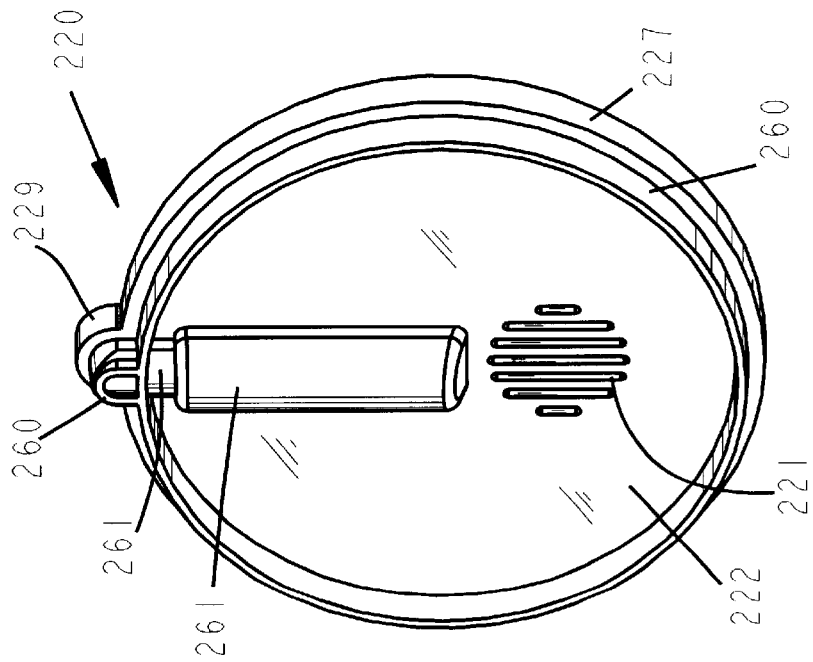

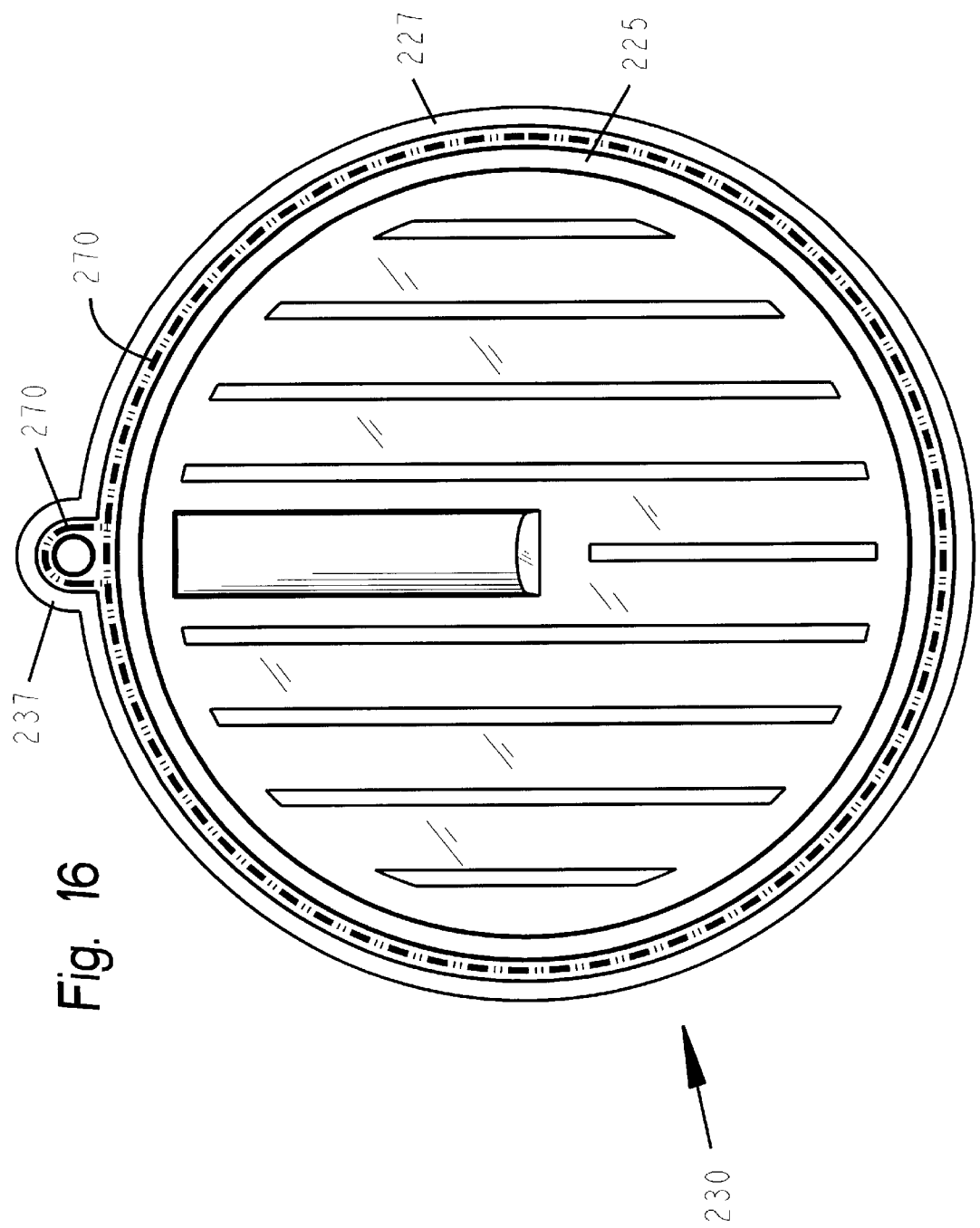

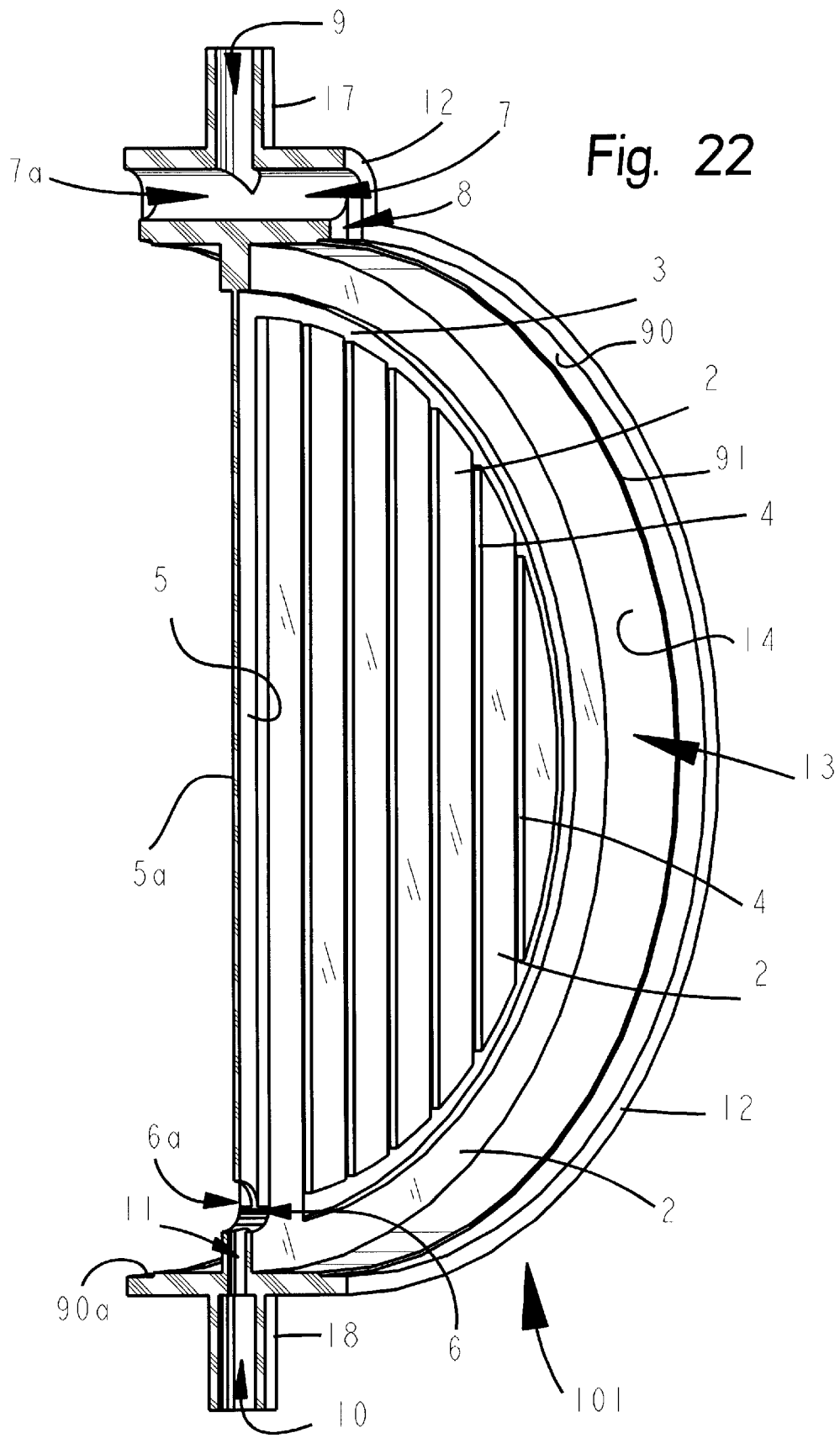

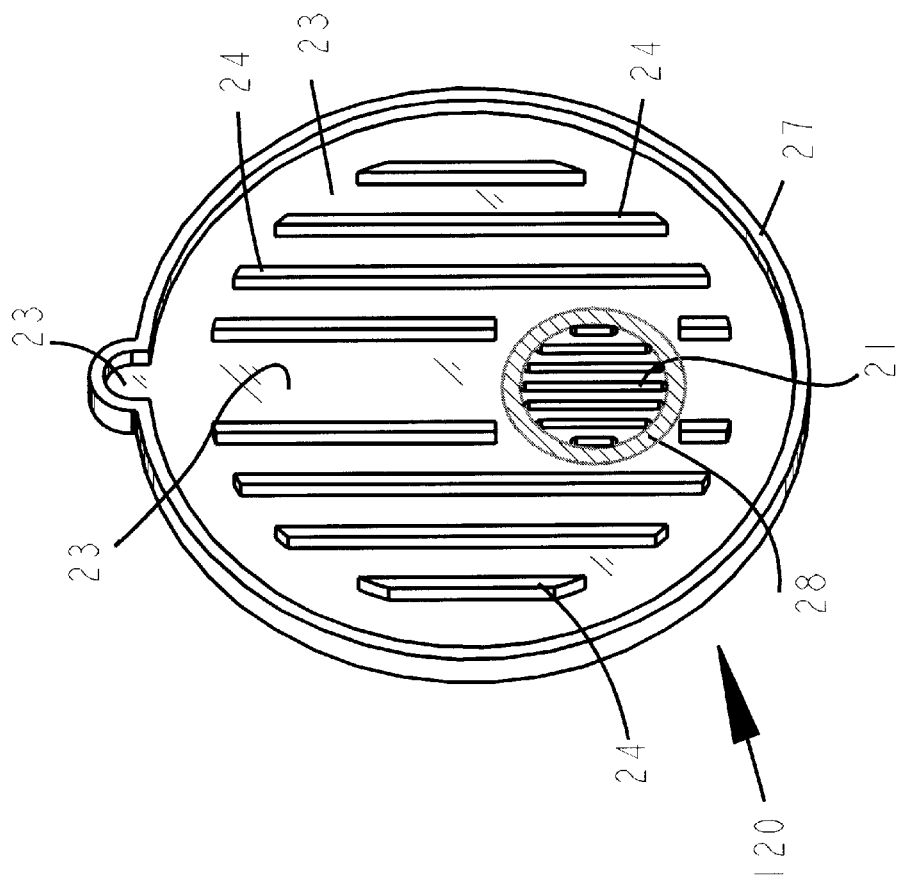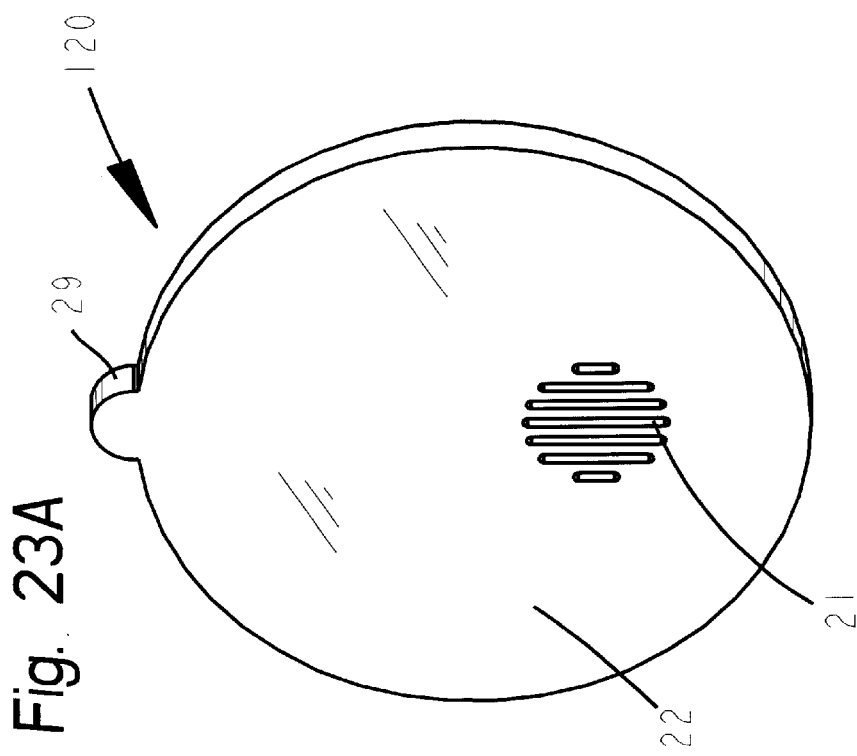

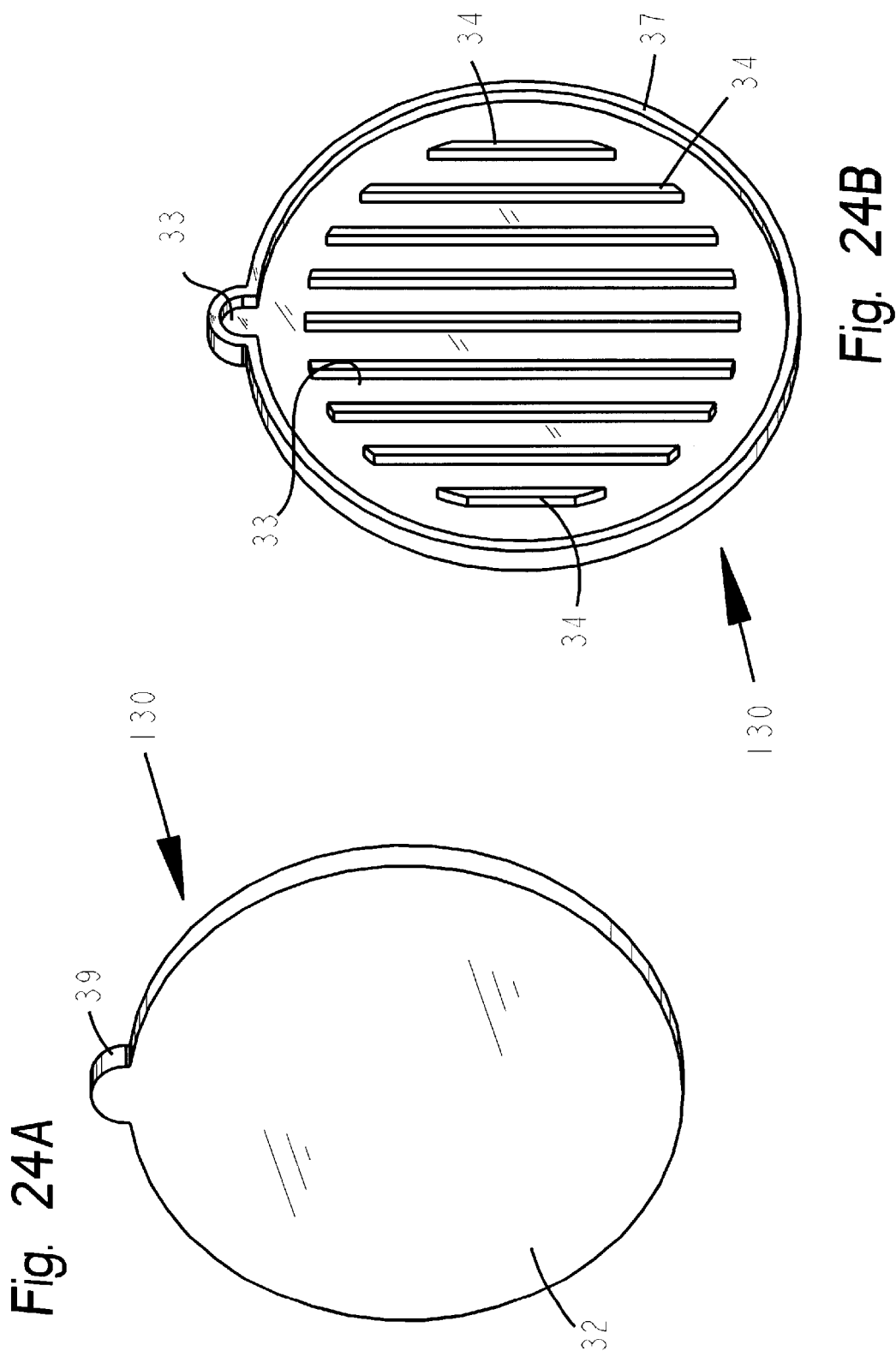

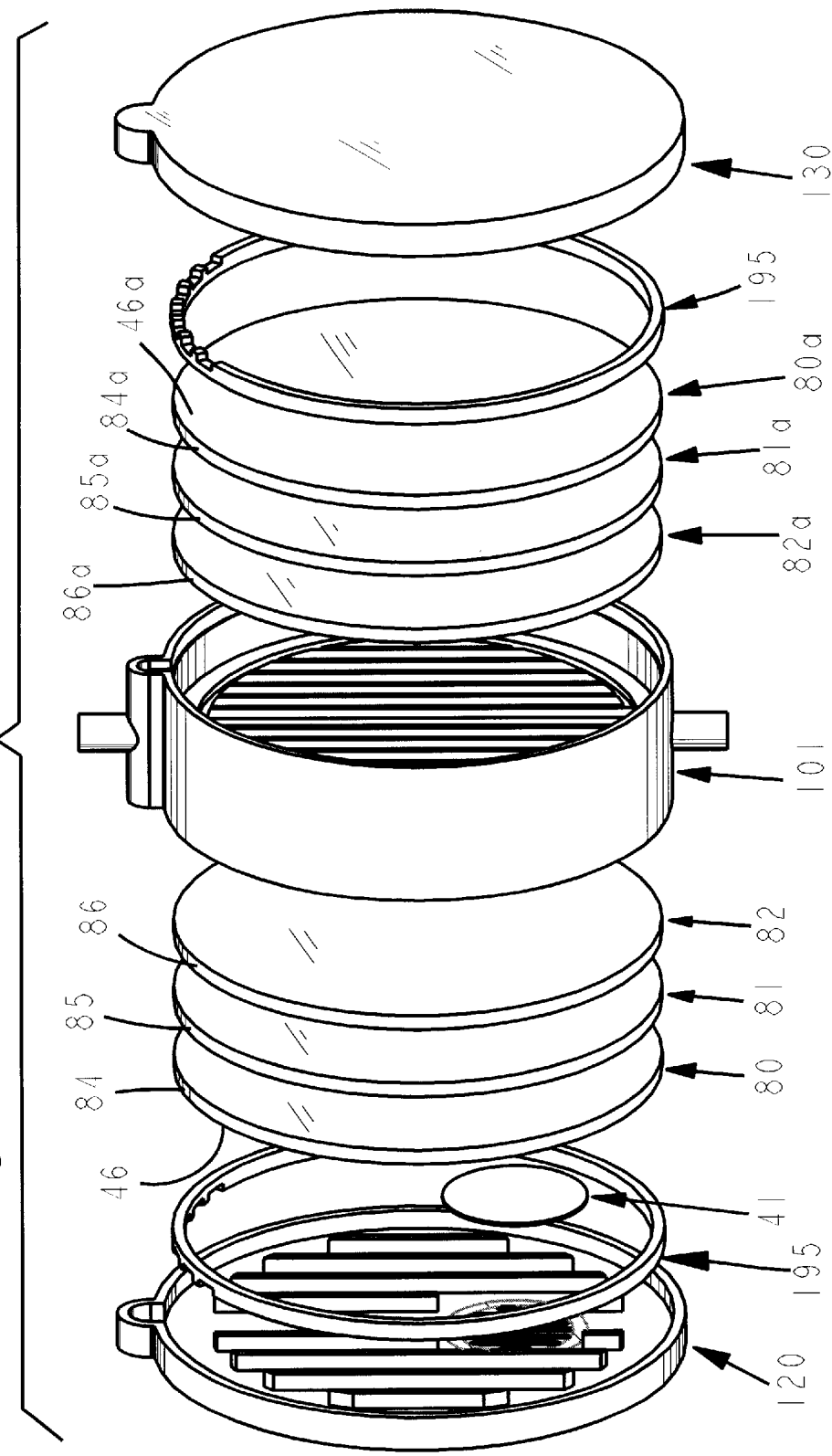

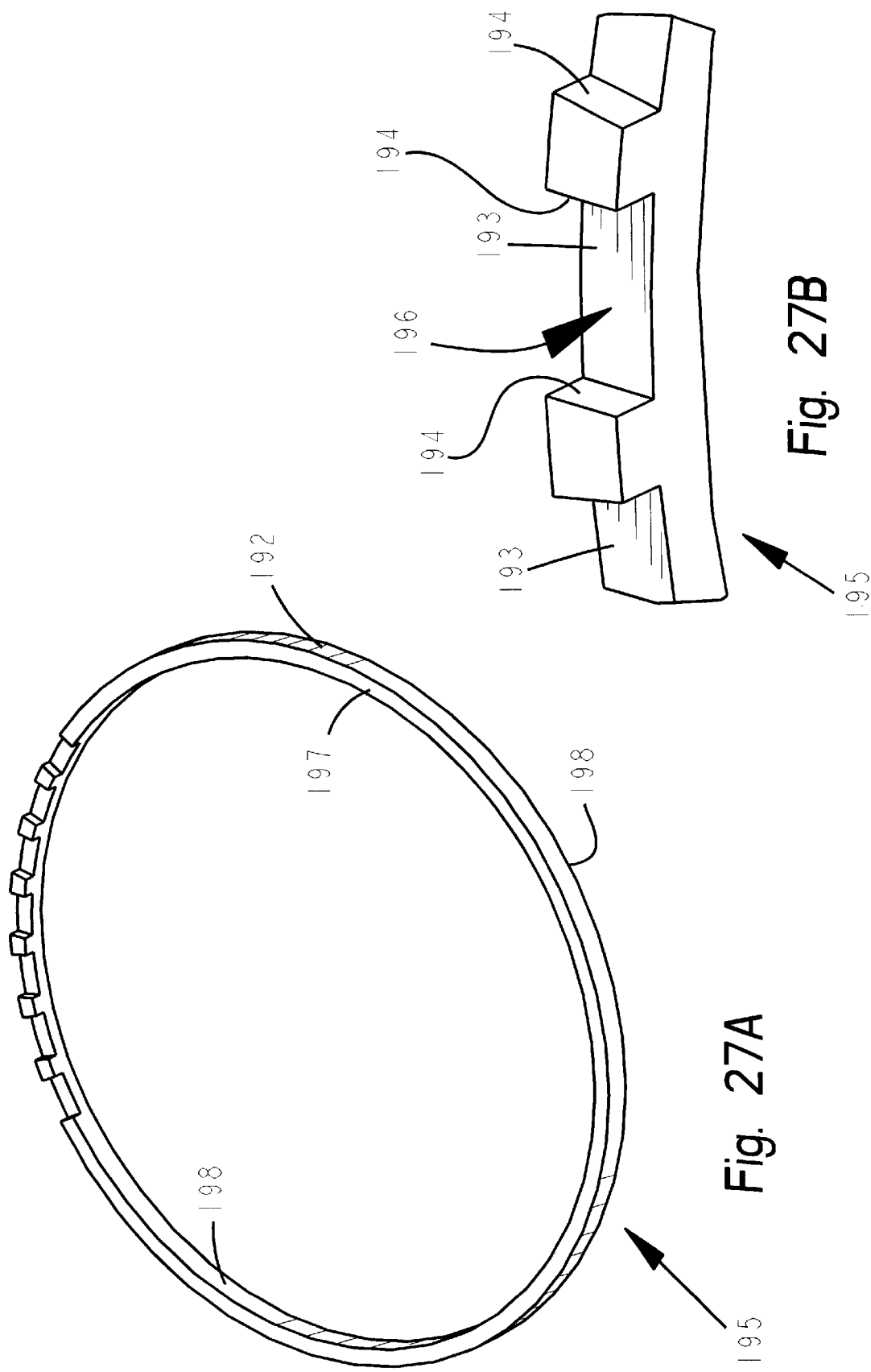

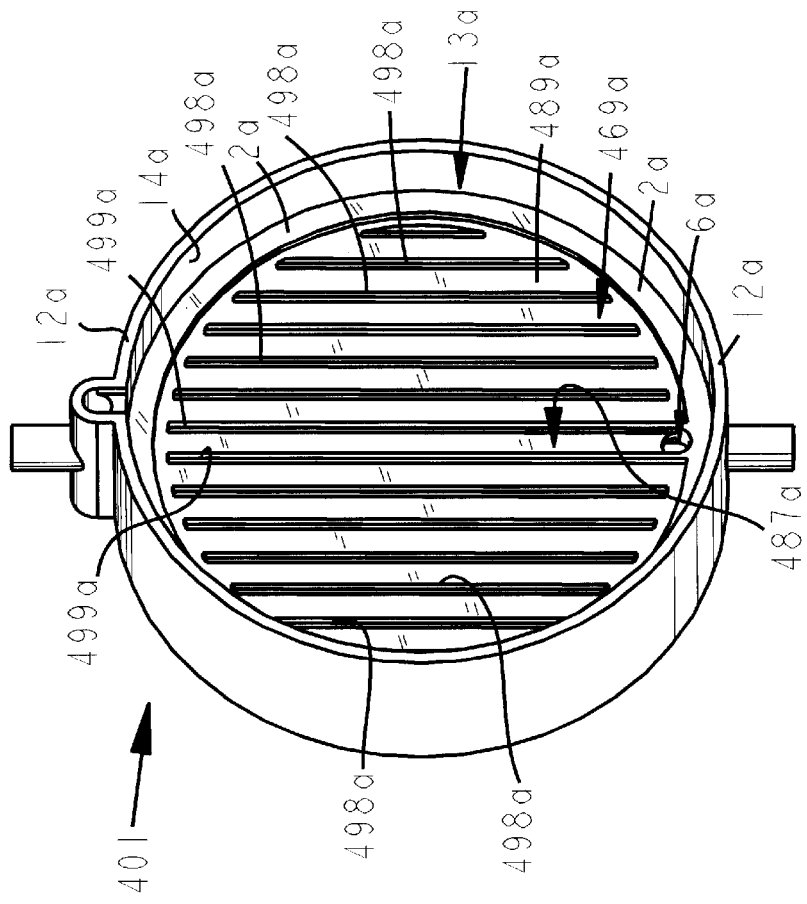
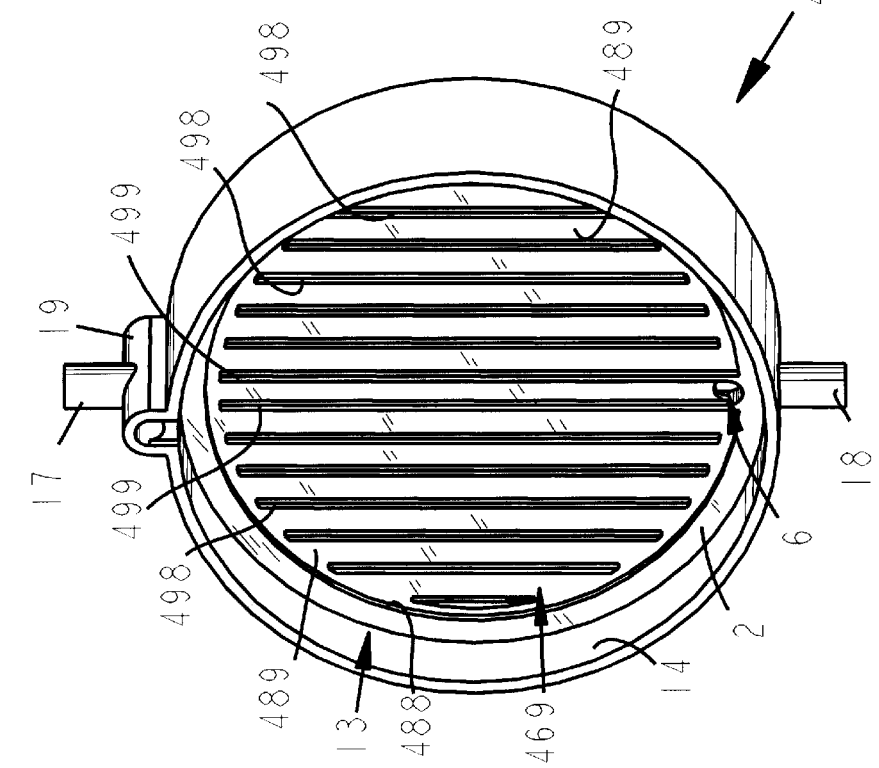
Fig. 28a
Fig. 28b

HIGH CAPACITY GRAVITY FEED FILTER FOR FILTERING BLOOD AND BLOOD PRODUCTS

This application claims priority of U.S. Provisional Application Serial No. 60/192,733 filed Mar. 27, 2000.

BACKGROUND OF THE INVENTION

This invention relates to the filtration field, and more particularly, to an improved gravity feed filtration device for filtering blood and blood products.

There are commercially available gravity filtration devices for filtering blood and blood products. The currently available gravity feed blood filters are capable of filtering a single unit of blood. Furthermore, certain types of blood or blood products foul the currently available devices before a single unit of blood can be filtered.

It is therefore an object of the present invention to provide a gravity feed filtration device capable of filtering any type of blood or blood product, and capable of filtering at least two units of blood.

SUMMARY OF THE INVENTION

The foregoing problems of the prior art are solved, and the objects of the present invention are achieved, by use of a filtration apparatus constructed in accordance with the principles of the present invention.

In accordance with the present invention, the filtration apparatus for the gravity filtration of blood or blood products is divided into two independent filtration chambers. The apparatus contains a common inlet port that is in fluid flow communication with inlet ports of the two independent filtration chambers, and a common outlet port that is in fluid flow communication with outlet ports of the two independent filtration chambers. The apparatus also contains a means to automatically drain the upstream portion of both of the filtration chambers once the filtration process is complete.

BRIEF DESCRIPTION OF THE DRAWINGS

These and other objects, features and advantages of the invention will be evident from the following detailed description when read in conjunction with the accompanying drawings in which:

FIG. 1A is a front isometric view of the body of the filtration apparatus depicted in FIG. 6;

FIG. 1B is a back isometric view of the body of the filtration apparatus depicted in FIG. 6;

FIG. 3A is a partial front isometric view of the top portion of the body depicted in FIG. 1a;

FIG. 3B is a partial back isometric view of the top portion of the body depicted in FIG. 1b;

FIG. 4A is a front isometric view of the front cover of the filtration apparatus depicted in FIG. 6;

FIG. 4B is a back isometric view of the front cover of the filtration apparatus depicted in FIG. 6;

FIG. 5A is a front isometric view of the back cover of the filtration apparatus depicted in FIG. 6;

FIG. 5B is a back isometric view of the back cover of the filtration apparatus depicted in FIG. 6;

FIG. 6 is an exploded isometric view of the components that comprise the first embodiment of the filtration apparatus, constructed in accordance with the principles of the present invention, usable for the gravity filtration of blood and blood products;

FIG. 9 is an isometric view of a blood filtration assembly containing the filtration apparatus depicted in FIG. 6;

FIG. 10A is a front isometric view of the body of the filtration apparatus depicted in FIG. 17;

FIG. 10B is a back isometric view of the body of the filtration apparatus depicted in FIG. 17;

FIG. 12A is a partial front isometric view of the top portion of the body depicted in FIG. 10A;

FIG. 12B is a partial back isometric view of the top portion of the body depicted in FIG. 10B;

FIG. 13A is a front isometric view of the front cover of the filtration apparatus depicted in FIG. 17;

FIG. 13B is a back isometric view of the front cover of the filtration apparatus depicted in FIG. 17;

FIG. 16 is a back view of the back cover of the filtration apparatus depicted in FIG. 17;

FIG. 22 is an isometric view, having portions thereof removed, of the body of the filtration apparatus depicted in FIG. 25;

FIG. 23A is a front isometric view of the front cover of the filtration apparatus depicted in FIG. 25;

FIG. 23B is a back isometric view of the front cover of the filtration apparatus depicted in FIG. 25;

FIG. 24A is a front isometric view of the back cover of the filtration apparatus depicted in FIG. 25;

FIG. 24B is a back isometric view of the back cover of the filtration apparatus depicted in FIG. 25;

FIG. 25 is an exploded isometric view of the components that comprise the third embodiment of the filtration apparatus, constructed in accordance with the principles of the present invention, usable for the gravity filtration of blood and blood products;

FIG. 27A is an isometric view of a filter compression ring of the filtration apparatus depicted in FIG. 25;

FIG. 27B is a partial isometric view of the top portion of the filter compression ring depicted in FIG. 27A;

FIG. 28A is a front isometric view of the body of the filtration apparatus depicted in FIG. 30;

FIG. 28B is a back isometric view of the body of the filtration apparatus depicted in FIG. 30;

DETAILED DESCRIPTION OF THE PREFERRED EMBODIMENTS

Figure 2:
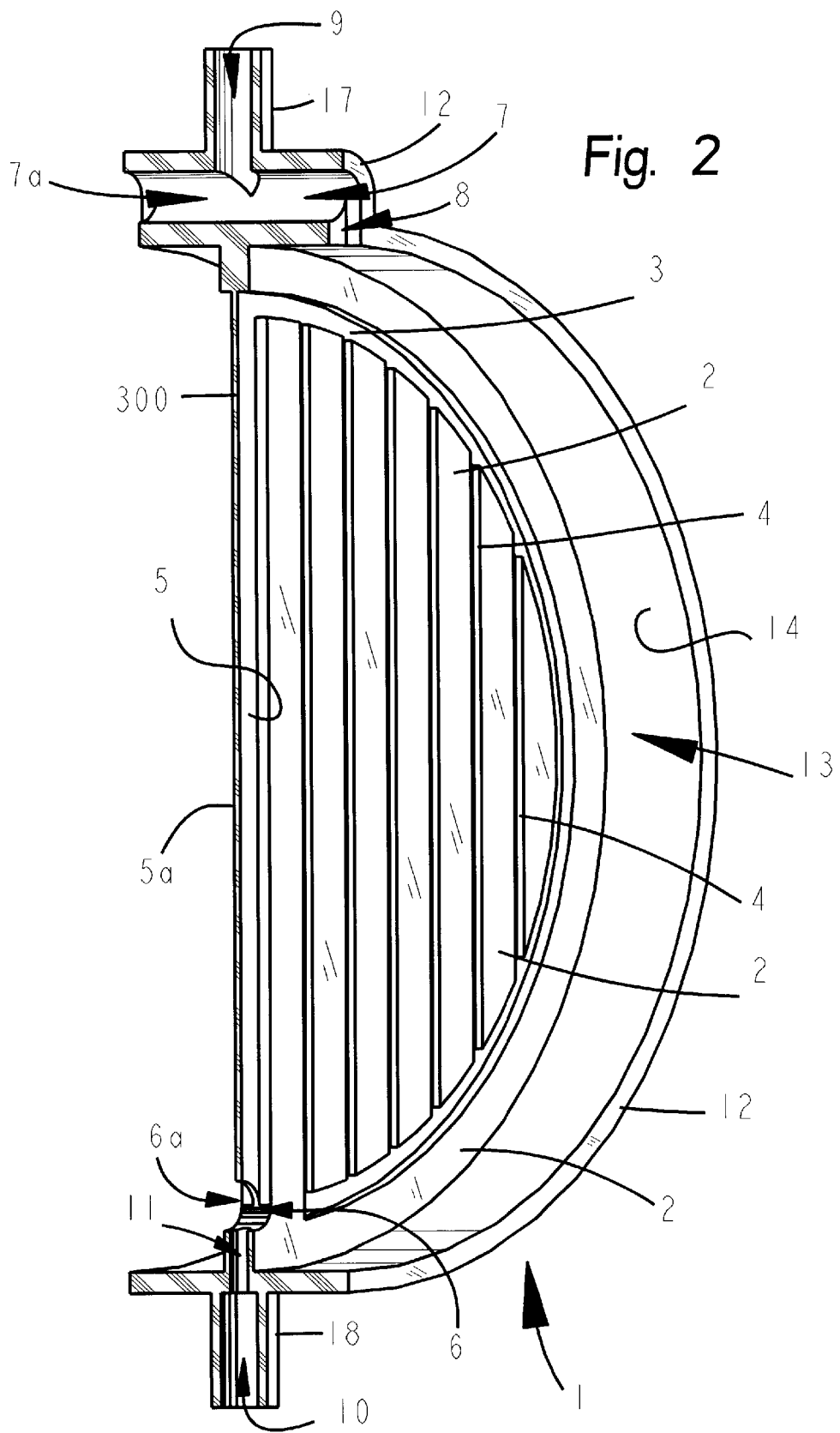
FIG. 2 is an isometric view, having portions thereof removed, of the body of the filtration apparatus depicted in FIG. 6.

Although various embodiments of the filtration device constructed in accordance with the present invention are disclosed herein, each embodiment enables the filtration device to filter more than one unit of blood.

One embodiment of the filtration device constructed in accordance with the principles of the present invention, is shown in FIG. 1A through FIG. 8. Referring to FIG. 6 this embodiment includes the following major components: front cover 20, body 1, back cover 30, filter elements 80, 81, 82, 80a, 81a, and 82a, and hydrophobic vent filter element 41.

FIG. 1A, FIG. 2, and FIG. 3A show the front part of body 1. The front part of body 1 contains a first filter well 13, defined by front flat surface 2 of partition wall 300 and cylindrical surface 14. The front face of partition wall 300 contains side vertical channels 4, circular channel 3, and center vertical channel 5. Preferably circular channel 3 is wider and deeper than side vertical channels 4, and center vertical channel 5 is wider than circular channel 3, and the same depth as circular channel 3. The upper and lower ends of side vertical channels 4 are in fluid flow relation with circular channel 3, and circular channel 3 is in fluid flow relation with center vertical channel 5. Center vertical channel 5 is in fluid flow relation with front outlet port 6. The upper central part of body 1 contains inlet tube socket 17, and cross protrusion 19. Inlet tube socket 17 contains inlet port 9, and cross protrusion 19 contains a cross port, with the front half of the cross port labeled front cross port 7, and the back half of the cross port labeled back cross port 7a. The outer end of cross port 7 contains front inlet channel 8, bounded by side walls 15 and wall 16. The lower central part of body 1 contains outlet tube socket 18. Outlet tube socket 18 contains outlet port 10. Front outlet port 6 is in fluid flow relation with outlet port 10 through link port 11.

FIG. 1B, and FIG. 3B show the back part of body 1. The back part of body 1 contains a second filter well 13a, defined by back flat surface 2a of partition wall 300 and cylindrical surface 14a. The back face of partition wall 300 contains side vertical channels 4a, circular channel 3a, and center vertical channel 5a. Preferably circular channel 3a is wider and deeper than side vertical channels 4a, and center vertical channel 5a is wider than circular channel 3a, and the same depth as circular channel 3a. The upper and lower ends of side vertical channels 4a are in fluid flow relation with circular channel 3a, and circular channel 3a is in fluid flow relation with center vertical channel 5a. Center vertical channel 5a is in fluid flow relation with back outlet port 6a. The upper central part of body 1 contains inlet tube socket 17, and cross protrusion 19. Inlet tube socket 17 contains inlet port 9, and cross protrusion 19 contains a cross port, with the front half of the cross port labeled front cross port 7, and the back half of the cross port labeled back cross port 7a. The outer end of cross port 7a contains back inlet channel 8a, bounded by side walls 15a and wall 16a. The lower central part of body 1 contains outlet tube socket 18. Outlet tube socket 18 contains outlet port 10. Back outlet port 6a is in fluid flow relation with outlet port 10 through link port 11. Front outlet port 6 may be a through hole as shown with the front half labeled front outlet port 6, and the back half labeled back outlet port 6a. As shown in FIGS. 1A through 3B the back part of body 1 is a mirror image of the front part of body 1. Body 1 is preferably made from an injection moldable medical grade plastic such acrylic, polycarbonate, polysulfone, polypropylene, polyethylene, but is not limited to these materials.

Figure 7:
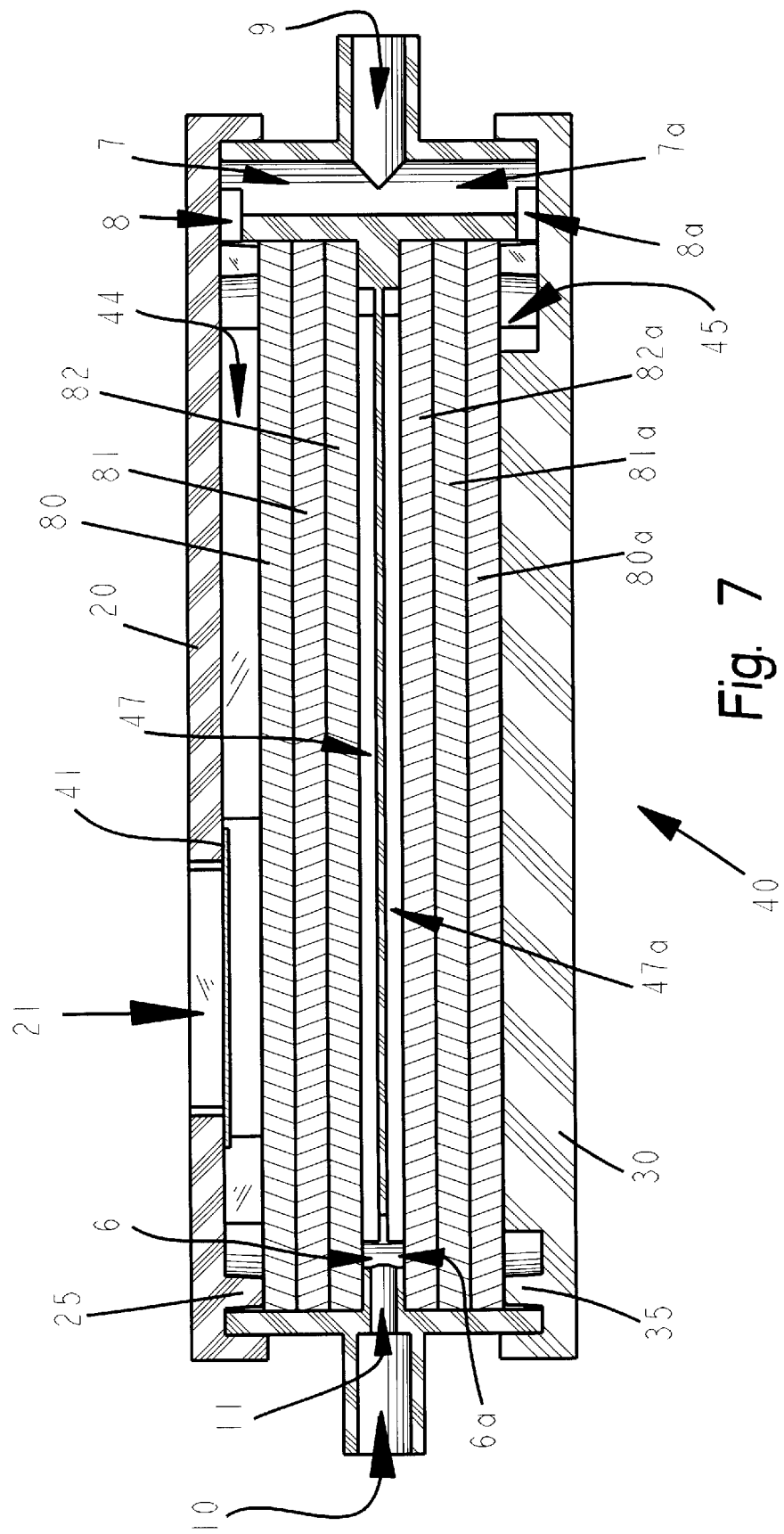
FIG. 7 is a cross-sectional view of the filtration apparatus depicted in FIG. 6.
Figure 21:
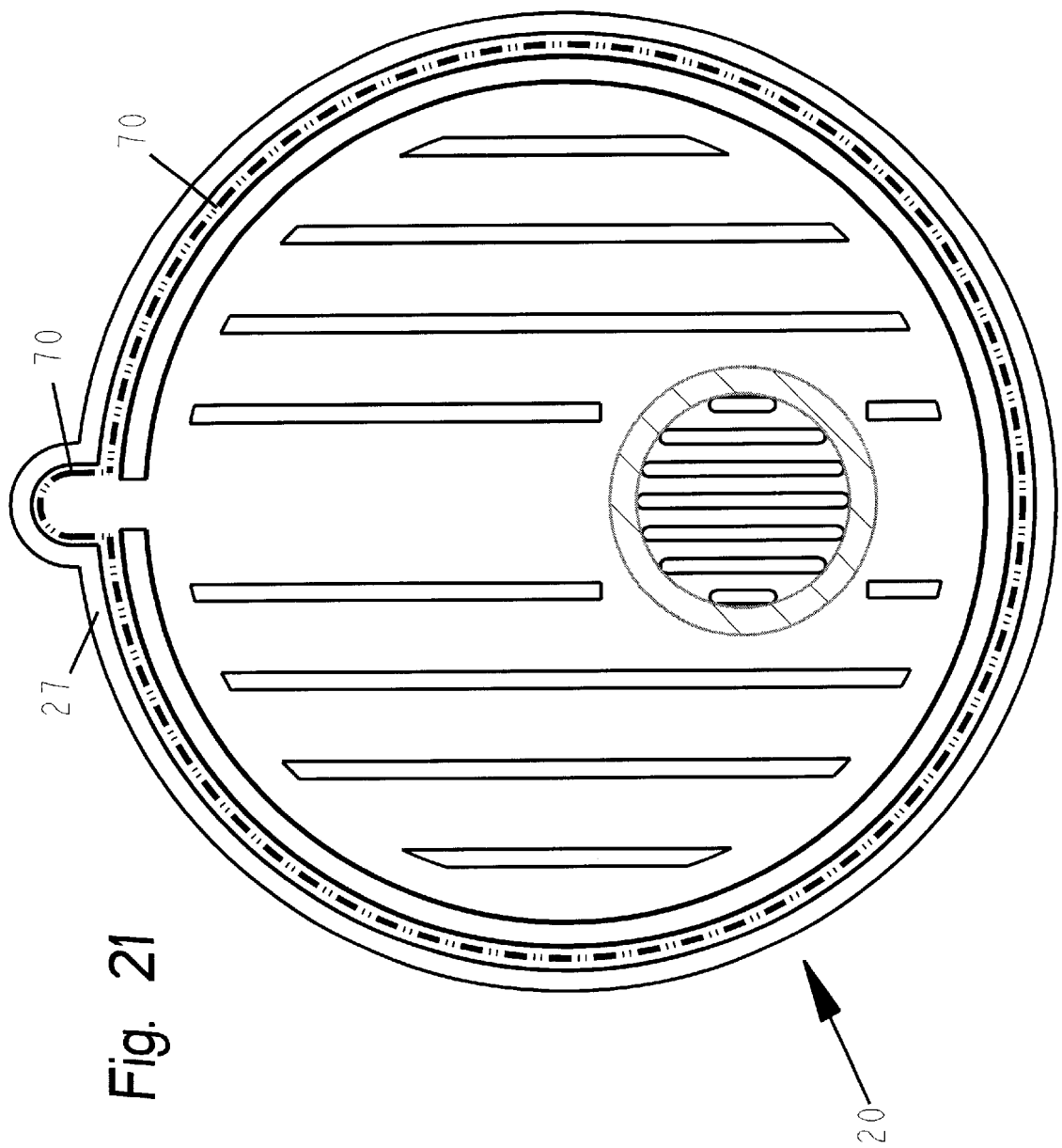
FIG. 21 is a back view of the front cover of the filtration apparatus depicted in FIG. 6.

FIG. 4A, FIG. 4B, and FIG. 21 show front cover 20. Front cover 20 is round in shape to match the shape of body 1, (if body 1 was square, then front cover 20 would also be square) and contains boss 29 at its upper end. The interior of front cover 20 contains flat surface 23. Vertical filter support ribs 24 protrude from flat surface 23. The vertical filter support ribs 24 could be replaced with ribs oriented in a direction other than vertical, or with a pattern of round pins, or with a pattern or rectangular pins, or with a pattern of concentric rings with gaps in the rings, or with any other filter support means that does not contain a closed loop. Outer rib 27 also protrudes from flat surface 23 and follows the outer periphery of front cover 20. Although it is not necessary for front cover 20 to contain outer rib 27, outer rib 27 acts as an alignment rib during assembly, and as a flash trap to contain flash when front cover 20 is assembled to body 1. Front cover 20 also contains round filter support rib 25. Round filter support rib 25 contains gap 26 located at the upper end of front cover 20, below boss 29. Front cover 20 also contains through slots 21, and vent filter bonding area 28. Although filter bonding area 28 is shown round for bonding a round vent filter, the vent filter could be square or any other shape, and then the filter bonding area 28 would conform to the shape of the vent filter. Through slots 21 are shown as vertical slots, but could be replaced by a pattern of round holes, or a pattern of square holes, or any other pattern of through holes that provide adequate filter support, and also provide air flow communication between the face of the vent filter that is bonded to flat surface 23, and to the outside atmosphere of front cover 20. FIG. 7 shows vent filter element 41 bonded to front cover 20. The outside of front cover 20 contains flat surface 22. Referring to FIG. 21, centerline 70 shows the center of the seal between front cover 20 and body 1. The seal could be an ultrasonic weld, a glue bond, a heat bond, a solvent bond, or any other type of leak tight bond. Front cover 20 is preferably made from an injection moldable medical grade plastic such acrylic, polycarbonate, polysulfone, polypropylene, polyethylene, but is not limited to these materials.

FIG. 5A, FIG. 5B, and FIG. 21 show back cover 30. Back cover 30 is round in shape to match the shape of body 1, (if body 1 was square, then back cover 30 would also be square) and contains boss 39 at its upper end. The interior of back cover 30 contains flat surface 33. Vertical filter support ribs 34 protrude from flat surface 33. The vertical filter support ribs 34 could be replaced with ribs oriented in a direction other than vertical, or with a pattern of round pins, or with a pattern of rectangular pins, or with a pattern of concentric rings with gaps in the rings, or with any other filter support means that does not contain a closed loop. Outer rib 37 also protrudes from flat surface 33 and follows the outer periphery of back cover 30. Although it is not necessary for back cover 30 to contain outer rib 37, outer rib 37 acts as an alignment rib during assembly, and as a flash trap to contain flash when back cover 30 is assembled to body 1. Back cover 30 also contains round filter support rib 35. Round filter support rib 35 contains gap 36 located at the upper end of back cover 30, below boss 39. The outside of back cover 30 contains flat surface 32. Back cover 30 is identical to front cover 20 with the exception that back cover 30 does not contain a vent filter. Referring to FIG. 21, centerline 70 shows the center of the seal between back cover 30 and body 1. Back cover 30 is preferably made from an injection moldable medical grade plastic such acrylic, polycarbonate, polysulfone, polypropylene, polyethylene, but is not limited to these materials.

Figure 8:
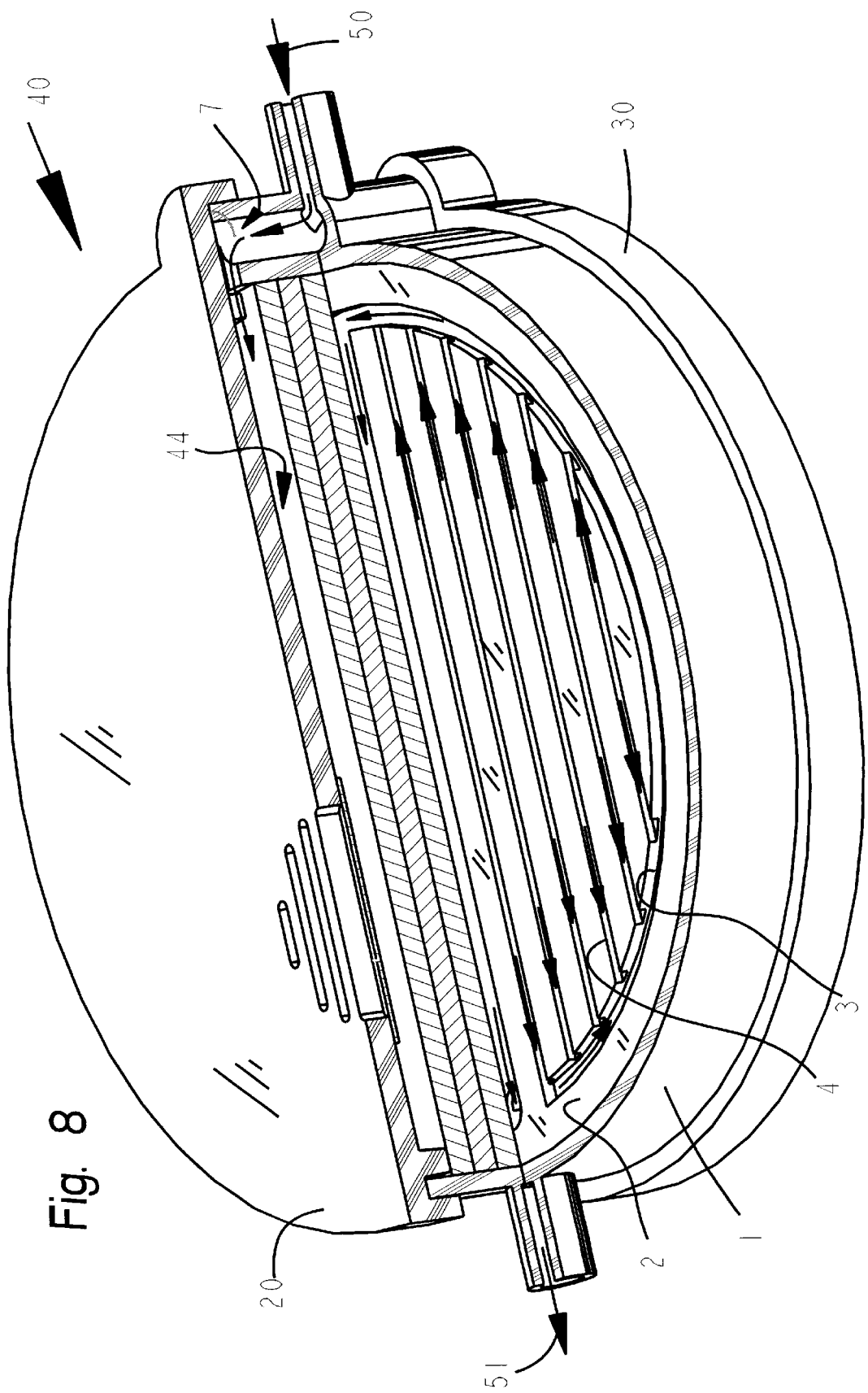
FIG. 8 is an isometric view of the filtration apparatus depicted in FIG. 6, having portions thereof removed.

FIG. 6 shows an exploded view of the components that comprise filter device 40. The components are body 1, front cover 20, back cover 30, vent filter element 41, and filter elements 80, 81, and 82, and filter elements 80a, 81a, and 82a. FIG. 7 and FIG. 8 show filter device 40 in the assembled state. Referring to FIG. 1A, FIG. 1B, FIG. 2, FIG. 4B, FIG. 5B, FIG. 6, FIG. 7, FIG. 8, and FIG. 21, the components that comprise filter device 40 are assembled as follows. The outer periphery of vent filter element 41 is sealed to front cover 20 at filter bonding area 28. The seal is preferably a heat seal but could be an ultrasonic seal, a glue bond, a solvent bond, or any other type of bond that will produce a leak tight seal capable of maintaining sterility. Filter element 41 is a hydrophobic filter with a pore size of 0.2 $\mu$ or smaller to maintain sterility. Filter elements 80, 81, and 82 are placed into first filter well 13. Front cover 20 is then bonded to body 1 so that edge 12 of body 1 is bonded to front cover 20 along centerline 70 shown in FIG. 21. The seal between front cover 20 and body 1 forms a single closed loop that encloses the outer periphery of first filter well 13 and the outer periphery of front inlet channel 8, thereby creating a closed first chamber 44 in first filter well 13, and a closed front inlet channel 8 that extends from front cross port 7 to first chamber 44 of first filter well 13, thereby creating a flow path from inlet port 9, through front cross port 7, through front inlet channel 8, into first chamber 44 of first filter well 13. Outer rib 27 of front cover 20 aligns front cover 20 to body 1 during the assembly procedure and also acts as a flash trap. The bond between front cover 20 and body 1 is preferably an ultrasonic seal but could be a glue bond, a heat bond, a solvent bond or any other type of bond that creates a leak tight seal. Filter elements 80, 81, and 82 are sealed to body 1 with a compression seal between the outer edges 84, 85, and 86 of filter elements 80, 81, and 82 respectively, and cylindrical surface 14 of body 1 in the filter device 40 shown. However, filter elements 80, 81, and 82 could be sealed to body 1 with a glue seal, a heat seal, a compression seal, or any other type of seal that eliminates bypass around filter elements 80, 81, and 82. Filter device 40 is shown with 3 filter elements 80, 81, and 82 in first filter well 13. However any number of filter elements greater than or equal to one could be used. The number of filter elements used is determined by the filter type and the fluid being filtered. The same number of filter elements that were placed into first filter well 13 of body 1 are now placed into second filter well 13a of body 1, and are designated as filter elements 80a, 81a, and 82a. These filter elements are sealed to body 1 using the same method that was used to seal filter elements 80, 81, and 82 to first filter well 13. Back cover 30 is then bonded to body 1 so that edge 12a of body 1 is bonded to back cover 30 along the same path as centerline 70 shown in FIG. 21. The seal between back cover 30 and body 1 forms a single closed loop that encloses the outer periphery of second filter well 13a and the outer periphery of back inlet channel 8a, thereby creating a closed first chamber 45 in second filter well 13a, and a closed back inlet channel 8a that extends from back cross port 7a to first chamber 45 of second filter well 13a, thereby creating a flow path from inlet port 9, through back cross port 7a, through back inlet channel 8a, into first chamber 45 of second filter well 13a. Outer rib 37 of back cover 30 aligns back cover 30 to body 1 during the assembly procedure and also acts as a flash trap. The bond between back cover 30 and body 1 is preferably an ultrasonic seal but could be a glue bond, a heat bond, a solvent bond or any other type of bond that creates a leak tight seal.

Referring to FIG. 4B, FIG. 6, FIG. 7, and FIG. 8, the assembled filter device 40 contains first chamber 44 of first filter well 13 bounded by flat surface 23 of front cover 20, inner surface 77 of round rib 25 of front cover 20, and the upstream surface 46 of the first filter element 80 in first filter well 13 of body 1. Referring to FIG. 5B, FIG. 6, and FIG. 7, the assembled filter device 40 also contains first chamber 45 of second filter well 13a bounded by flat surface 33 of back cover 30, inner surface 71 of round rib 35 of back cover 30, and the upstream surface 46a of the first filter element 80a in second filter well 13a of body 1. Referring to FIG. 3A and FIG. 7, in the assembled filter device 40, front inlet channel 8 becomes a closed channel bounded by side walls 15 and wall 16 of body 1, and by flat surface 23 of front cover 20. Referring to FIG. 7, front inlet channel 8 places first chamber 44 in fluid flow communication, and in air flow communication with front cross port 7. Referring to FIG. 3B and FIG. 7, in the assembled filter device 40, back inlet channel 8a becomes a closed channel bounded by side walls 15a and wall 16a of body 1, and by flat surface 33 of back cover 30. Referring to FIG. 7, back inlet channel 8a places first chamber 45 in fluid flow communication, and in air flow communication with back cross port 7a.

Referring to FIG. 1a, FIG. 2, FIG. 6 and FIG. 7, the assembled filter device 40 contains second chamber 47 of first filter well 13 bounded by the downstream surface 48 of the last filter element 82 in first filter well 13 of body 1, and by center vertical channel 5, circular channel 3, and side vertical channels 4. Second chamber 47 of first filter well 13 contains front outlet port 6. Referring to FIG. 1b, FIG. 6 and FIG. 7, the assembled filter device 40 contains second chamber 47a of second filter well 13a bounded by the downstream surface 48a of the last filter element 82a in second filter well 13a of body 1, and by center vertical channel 5a, circular channel 3a, and side vertical channels 4a. Second chamber 47a of second filter well 13a contains back outlet port 6a.

Referring to FIG. 9 one end of a length of outlet tubing 53 is bonded to outlet tube socket 18 of body 1, with the other end of said outlet tubing bonded to an empty blood bag 55. Another length of inlet tubing 52 is bonded to inlet tube socket 17 of body 1. The end user will preferably purchase the assembly of filter device 40, inlet tubing 52, outlet tubing 53, and receiving blood bag 55, assembled and sterile. The assembly will also contain an inlet tubing clamp 74 on inlet tubing 52, and an outlet tubing clamp 75 on outlet tubing 53.

In FIG. 9 the filter device 40 is in an operational assembly with inlet tubing 52, outlet tubing 53, feed blood bag 54, receiving blood bag 55, inlet tube clamp 76, and outlet tube clamp 75. Preferably, the user will purchase the assembly of FIG. 9 sterilized without feed blood bag 54 with the inlet end of inlet tubing 52 sealed to maintain system sterility. For performing filtration the user will first close inlet tube clamp 74 close to the inlet end of inlet tubing 52. Next the user will make sure that outlet tube clamp 75 is open. Inlet tubing 52 is now bonded by the user to a pigtail on feed blood bag 54 using a sterile docking device as is well known in the art.

Once the sterile docking connection is made the user will hang feed blood bag 54 from hook 57 on blood bag pole 56. Receiving blood bag 55 should be placed on a surface such as a table top or the like. The complete assembly 60 ready for filtration is illustrated in FIG. 9.

Referring to FIG. 1A, FIG. 4B, FIG. 5B, FIG. 7, FIG. 8 and FIG. 9 the filtration is performed as follows. The user opens inlet tube clamp 74. Gravity now forces blood to flow from feed blood bag 54, through inlet tubing 52, through inlet port 9 of body 1. After passing through inlet port 9, a portion of the blood passes through front cross port 7, while the remainder of the blood passes through back cross port 7a. The portion of the blood that passes through front cross port 7, then passes through front inlet channel 8, through gap 26 of front cover 20, into first chamber 44. The portion of the blood that passes through back cross port 7a, then passes through back inlet channel 8a, through gap 36 of back cover 30, into first chamber 45. A portion of the air that was in inlet tubing 52 and inlet port 9 before blood flow started will be pushed ahead of the blood, through front cross port 7, through front inlet channel 8, through gap 26 of front cover 20, into first chamber 44. The remainder of the air that was in inlet tubing 52 and inlet port 9 before blood flow started will be pushed ahead of the blood, through back cross port 7a, through back inlet channel 8a, through gap 36 of back cover 30, into first chamber 45. Because the usable surface area of hydrophobic filter 41 is much smaller than the usable surface area of filter elements 80, 81, and 82; and because the pressure drop across sterilizing grade hydrophobic filter 41 is much greater per unit volume of air flow per unit surface area of filter material than the combined pressure drop across filter elements 80, 81, and 82 per unit volume of air flow per unit surface area of filter material, only a very small portion of the air that was in inlet tubing 52, inlet port 9, front cross port 7, and front inlet channel 8 before blood flow started, will pass through hydrophobic filter 41, and then through slots 21 of front cover 20 to atmosphere.

As first chamber 44 fills from the bottom up most of the air in first chamber 44 will be forced through filter elements 80, 81, and 82, for the same reasons described in the previous paragraph. This initial air will flow into vertical channels 4, circular channel 3, and center vertical channel 5, and then flow through front outlet port 6, through link port 11, through outlet port 10, into outlet tubing 53, into receiving blood bag 55. Filter elements 80, 81, and 82 will also wet from the bottom up. The air that is initially in filter elements 80, 81, and 82 will be displaced by blood and flow into vertical channels 4, circular channel 3, and center vertical channel 5, and then flow through front outlet port 6, through link port 11, through outlet port 10, into outlet tubing 53, into receiving blood bag 55. Because the volume of first chamber 44 is small, and the flow rate of blood entering first chamber 44 is much greater than the initial flow rate of blood through filter elements 80, 81, and 82, first chamber 44 will fill in a very small fraction of the time that it takes to wet filter elements 80, 81, and 82. The pressure head at the bottom of first chamber 44 will be larger than the pressure head at the top of first chamber 44, because of the height difference between the top and bottom of first chamber 44. Therefore liquid will start to come through filter element 82 from the bottom up. As liquid starts to come through filter element 82 from the bottom up vertical channels 4, circular channel 3, and center vertical channel 5, of body 1 will fill from the bottom up. Because the total volume of these channels in is small (to minimize holdup) the channels may fill with blood (from the bottom up) before the upper part of filter element 82 has wet with blood. Once blood starts to flow from center, vertical channel 5 of body 1, into front outlet port 6 of body 1, through link port 11 of body 1, through outlet port 10 of body 1, into outlet tubing 53, and starts to flow down outlet tubing 53 toward receiving blood bag 55, the pressure in front outlet port 6 will become negative. Because center vertical channel 5 is in fluid flow relationship with front outlet port 6, the pressure inside the tube created by center vertical channel 5 and downstream surface 48 of filter element 82 will also be negative. Likewise since circular channel 3 is in fluid flow relationship with center vertical channel 5 the pressure inside the tube created by circular channel 3 and downstream surface 48 of filter element 82 will also be negative. Since the tube segments made up of vertical channels 4 and downstream surface 48 of filter element 82 are in fluid flow relationship with the tube created by circular channel 3 and downstream surface 48 of filter element 82, any air or liquid that flows from filter element 82 into vertical channels 4 will be sucked into circular channel 3, and then flow from circular channel 3 into center vertical channel 5, through front outlet port 6, through link port 11, through outlet port 10, into outlet tubing 53, and into receiving blood bag 55. This assures that filter elements 80, 81, and 82 will completely wet, and that all of the air that was in first chamber 44, filter elements 80, 81, and 82, vertical channels 4, circular channel 3, center circular channel 5, front outlet port 6, link port 11, outlet port 10, and the interior of outlet tubing 53 will be forced into receiving blood bag 55. Although vertical channels 4 are shown in the vertical orientation, they could be orientated at any angle from zero degrees to ninety degrees from vertical, as long as they are in fluid flow relationship with circular channel 3. Other channel designs such as the spiral channel filter underdrain disclosed in U.S. Ser No. 08/524,049 U.S. Pat. No. 5,798,041, and entitled "an In-Line Liquid Filtration Device Usable for Blood, Blood Products and the Like", could also be used in place of the design illustrated in FIG. 1A. It is however, imperative that all channels be either directly or indirectly in fluid flow relationship with front outlet port 6.

The portion of blood from feed blood bag 54 which flows through back cross port 7a, through back inlet channel 8a, through gap 36, into first chamber 45, will fill first chamber 45 from the bottom forcing all of the air in first chamber 45 through filter elements 80a, 81a, and 82a. This initial air will flow into vertical channels 4a, circular channel 3a, and center vertical channel 5a, and then flow through back outlet port 6a, through link port 11, through outlet port 10, into outlet tubing 53, into receiving blood bag 55. Filter elements 80a, 81a, and 82a will also wet from the bottom up. The air that is initially in filter elements 80a, 81a, and 82a will be displaced by blood and flow into vertical channels 4a, circular channel 3a, and center vertical channel 5a, and then flow through outlet port 6a, through link port 11, through outlet port 10, into outlet tubing 53, into receiving blood bag 55. Because the volume of first chamber 45 is small, and the flow rate of blood entering first chamber 45 is much greater than the initial flow rate of blood through filter elements 80a, 81a, and 82a, first chamber 45 will fill in a very small fraction of the time that it takes to wet filter elements 80a, 81a, and 82a. The pressure head at the bottom of first chamber 45 will be larger than the pressure head at the top of first chamber 45, because of the height difference between the top and bottom of first chamber 45. Therefore liquid will start to come through filter element 82a from the bottom up. As liquid starts to come through filter element 82a from the bottom up vertical channels 4a, circular channel 3a, and center vertical channel 5a, of body 1 will fill from the bottom up. Because the total volume of these channels in is small (to minimize holdup) the channels may fill with blood (from the bottom up) before the upper part of filter element 82a has wet with blood. Once blood starts to flow from center vertical channel 5a of body 1, into back outlet port 6a of body 1, through link port 11 of body 1, through outlet port 10 of body 1, into outlet tubing 53, and starts to flow down outlet tubing 53 toward receiving blood bag 55, the pressure in back outlet port 6a will become negative. Because center vertical channel 5a is in fluid flow relationship with back outlet port 6a, the pressure inside the tube created by center vertical channel 5a and the downstream surface 48a of filter element 82a will also be negative. Likewise since circular channel 3a is in fluid flow relationship with center vertical channel 5a the pressure inside the tube created by circular channel 3a and the downstream surface 48a of filter element 82a will also be negative. Since the tube segments made up of vertical channels 4a and the downstream surface 48a of filter element 82a are in fluid flow relationship with the tube created by circular channel 3a and the downstream surface 48a of filter element 82a, any air or liquid that flows from filter element 82a into vertical channels 4a will be sucked into circular channel 3a, and then flow from circular channel 3a into center vertical channel 5a, through back outlet port 6a, through link port 11, through outlet port 10, into outlet tubing 53, and into receiving blood bag 55. This assures that filter elements 80a, 81a, and 82a will completely wet, and that all of the air that was in first chamber 45, filter elements 80a, 81a, and 82a, vertical channels 4a, circular channel 3a, center circular channel 5a, back outlet port 6a, link port 11, outlet port 10, and the interior of outlet tubing 53 will be forced into receiving blood bag 55. Although vertical channels 4a are shown in the vertical orientation, they could be orientated at any angle from zero degrees to ninety degrees from vertical, as long as they are in fluid flow relationship with circular channel 3a. Other channel designs such as the spiral channel filter underdrain disclosed in U.S. Ser. No. 08/524,049, U.S. Pat. No. 5,798,041, and entitled "an In-Line Liquid Filtration Device Usable for Blood, Blood Products and the Like", could also be used in place of the design illustrated in FIG. 1B. It is however, imperative that all channels be either directly or indirectly in fluid flow relationship with back outlet port 6a.

Blood filtration will continue until feed blood bag 54 is empty. When feed blood bag 54 is empty it will be collapsed and therefore close the inlet end of inlet tubing 52. Because outlet tubing 53 will be full of blood, and because the outside of receiving blood bag 55 is at atmospheric pressure, the pressure head in front outlet port 6, and the pressure head in back outlet port 6a will be negative, as will be the pressure head in vertical channels 4, circular channel 3, center vertical channel 5, vertical channels 4a, circular channel 3a, and center vertical channel 5a, all of body 1. Once blood flow has stopped the pressure drop across filter elements 80, 81, and 82, will fall to zero. The pressure drop across filter elements 80a, 81a, and 82a, will also fall to zero. Hence the pressure in first chamber 44 and first chamber 45 will become negative. Once the pressure in first chamber 44 falls below atmospheric pressure air will begin to flow from atmosphere through slots 21, through sterilizing grade hydrophobic filter 41, into first chamber 44. The sterile air that enters first chamber 44 will bubble up to the top of first chamber 44, thus causing first chamber 44 to drain from the top down. Because of the negative pressure in first chamber 45, some of the air that bubbles to the top of first chamber 44 will pass through gap 26, through front inlet channel 8, through front cross port 7, through back cross port 7a, through gap 36, through back inlet channel 8a, into first chamber 45, causing first chamber 45 to drain from the top down, and causing the blood in front inlet channel 8 to drain into first chamber 44, and causing the blood in back inlet channel 8a to drain into first chamber 45, and causing the blood in front cross port 7 and back cross port 7a to drain into both first chamber 44 and first chamber 45. Because the air entering first chamber 44 bubbles to the top of first chamber 44, thus draining first chamber 44 from the top down, vent filter element 41 can be located anywhere on flat surface 23 of front cover 20. Filter elements 80, 81, 82, 80a, 81a, and 82a will be plugged sufficiently at this point, therefore very little if any blood will be sucked from these filter elements by the negative pressure in front outlet port 6, and by the negative pressure in back outlet port 6a. Hence blood flow will stop after first chamber 44 and first chamber 45 have drained and blood will remain in filter elements 80, 81, 82, 80a, 81a, and 82a, and in vertical channels 4, circular channel 3, center vertical channel 5, vertical channels 4a, circular channel 3a, and center vertical channel 5a, and in front outlet port 6, back outlet port 6a, link port 11, outlet port 10 all of body 1, and in outlet tubing 53.

The user can now close tube clamp 75 on outlet tubing 53 and then seal outlet tubing 53 above tube clamp 75, and then cut outlet tubing 53 above the seal just made. Feed blood bag 54, inlet tubing 52, and filter device 40 can now be discarded in a safe manner. Outlet tubing 53 will have segments marked on them. The user can now seal the tubing at the segment marks. The blood that is left in outlet tubing 53 will be used for cross matching and for quality control purposes.

Referring to FIG. 2, with front outlet port 6 and back outlet port 6a at the very bottom of center vertical channels 5 and 5a respectively, the length of link port 11 is minimized, thereby minimizing the diameter of the pin (a minimum diameter is needed to prevent breakage of the pin) in the injection mold, thereby minimizing the wall thickness of partition wall 300 of body 1, thereby reducing the cost of body 1.

A second embodiment of the filtration device constructed in accordance with the principles of the present invention, could be constructed by replacing the back cover 30 of the first embodiment with a second front cover 20. The second embodiment would work the same as the first embodiment, with the exception that after the feed blood bag is empty, air would enter first chamber 45 from the vent filter on the front cover 20 that replaces the back cover 30.

The first and second embodiments of the present invention contain the following shortcoming if it is desired to seal filter elements 80, 81, and 82 into first filter well 13 of body 1 by compressing the outer periphery of said filter elements between round filter support rib 25 of front cover 20 and front flat surface 2 of body 1. Referring to FIG. 2, FIG. 4B and FIG. 7, the peripheral compression seal contains a break at gap 26 of round filter support rib 25 of front cover 20. Therefore a small portion of unfiltered blood will flow into the gap between outer wall 72 of round filter support rib 25 of front cover 20 and cylindrical surface 14 of body 1. Likewise, referring to FIG. 1B, FIG. 5B, and FIG. 7, if it is desired to seal filter elements 80a, 81a, and 82a into second filter well 13a of body 1 by compressing the outer periphery of said filter elements between round filter support rib 35 and back flat surface 2a of body 1, said compression seal contains a break at gap 36 of round filter support rib 35 of back cover 30. Therefore a small portion of unfiltered blood will flow into the gap between outer wall 73 of round filter support rib 35 of back cover 30 and cylindrical surface 14a of body 1. The third embodiment constructed in accordance with the principles of the present invention overcomes these shortcomings.

FIG. 25 shows an exploded view of the components that comprise the third embodiment of the present invention. Referring to FIG. 25, body 101 replaces body 1 of the first and second embodiments of the present invention. Likewise, front cover 120 replaces front cover 20, and back cover 130 replaces back cover 30 of the first and second embodiments of the present invention. The third embodiment also contains two filter compression rings 195.

Figure 26:
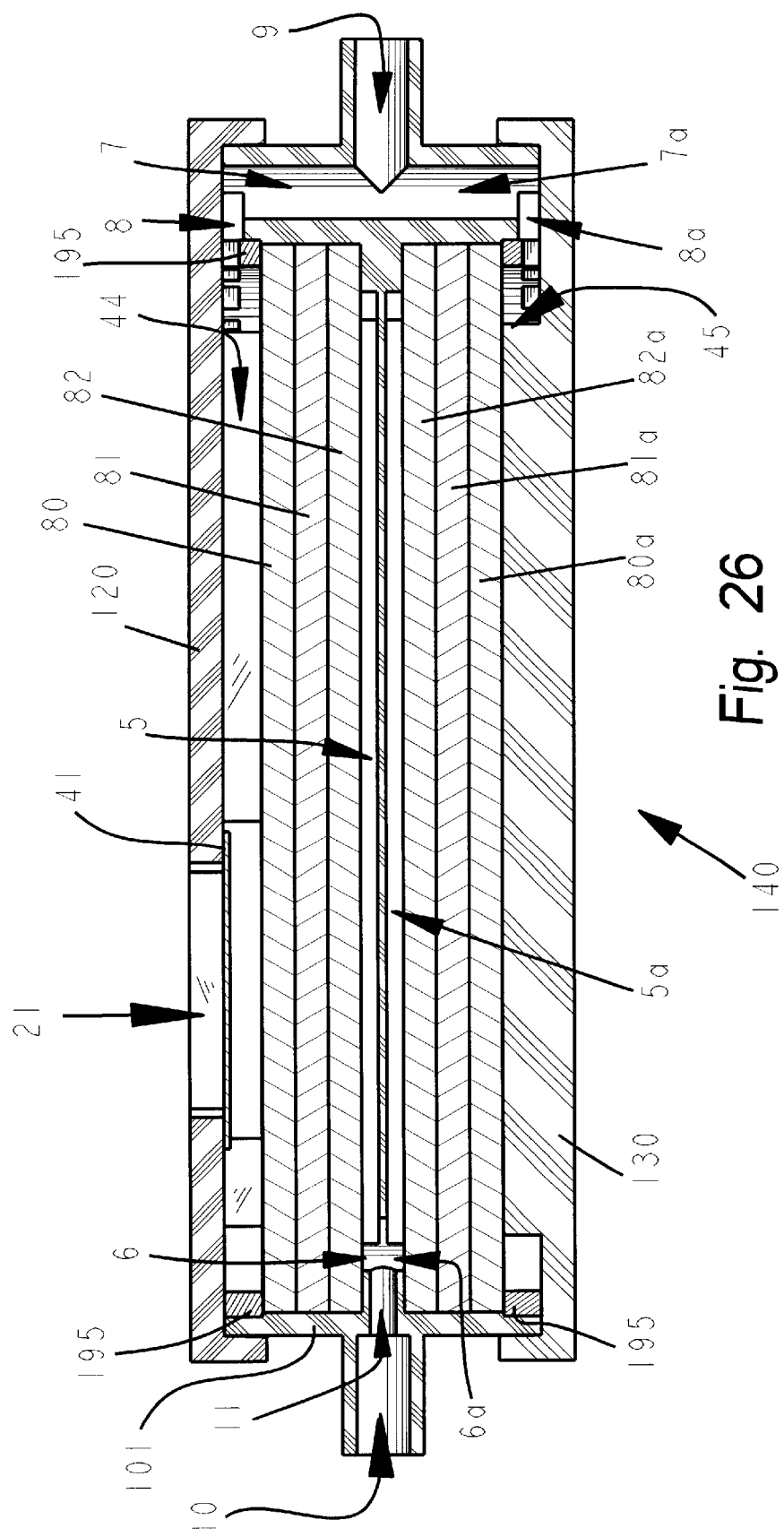
FIG. 26 is a cross-sectional view of the filtration apparatus depicted in FIG. 25.

Referring to FIG. 22, body 101 is the same as body 1 shown in FIG. 1a, FIG. 1B, and FIG. 2, with the exception that the front part of body 101 contains a counterbore in cylindrical surface 14, bounded by surface 90 and surface 91. The back part of body 101 shown in FIG. 25 also contains a corresponding counterbore. Referring to FIG. 23A and FIG. 23B, front cover 120 is identical to front cover 20 shown in FIG. 4A and FIG. 4B, with the exception that front cover 120 does not contain round filter support rib 25. Referring to FIG. 24A and FIG. 24B, back cover 130 is identical to back cover 30 shown in FIG. 5A and FIG. 5B, with the exception that back cover 130 does not contain round filter support rib 35. FIGS. 27A and 27B show filter compression ring 195. Filter compression ring 195 is a hollow cylinder, and contains one or more notches 196 in face 197. Each notch 196 is formed by two side walls 194 and an end wall 193. FIG. 25 and FIG. 26 show filter compression rings 195 properly oriented. When properly oriented notches 196 provide a liquid and gas flow path between front inlet channel 8 and first chamber 44, and provide a liquid and gas flow path between back inlet channel 8a and first chamber 45, as shown in FIG. 26. Only one notch 196 is necessary in compression ring 195 if compression ring 195 is properly aligned to front inlet channel 8, and back inlet channel 8a. Providing more than one notch 196 in filter compression ring 195 as shown in FIG. 27A, allows for some misalignment of filter compression ring 195 with respect to front inlet channel 8, and back inlet channel 8a, provided that the space between notches 196 is less than the width of front inlet channel 8 and back inlet channel 8a. If filter compression ring 195 contains more than one notch 196, said notches should be restricted to the top portion of filter compression ring 195 as shown in FIG. 25 and FIG. 27A, so that any blood that enters the notches during the filtration process can drain once filtration has stopped.

Referring to FIG. 22, FIG. 25, and FIG. 27a filter compression ring 195 should be sized so that outer wall 192 of filter compression ring 195 press fits into surface 90 of body 101, and so that outer wall 192 of filter compression ring 195 press fits into surface 90a of body 101, so that no gap will exist between outer wall 192 of filter compression ring 195 and surface 90 or surface 90a of body 101. Filter compression ring 195 is preferably made from an injection moldable plastic, and is preferably made of a softer plastic than body 101 to facilitate pressing filter compression ring 195 into body 101. Alternately filter compression ring 195 can be made of the same material as body 101, and sealed to body 101 with a sonic weld, a glue bond, a solvent bond or a heat bond, or any other type of suitable bond.

Filter device 140 shown in FIG. 26 functions the same as filter device 40 shown in FIG. 7. However the shortcomings of the first and second embodiments of the present invention as described above are overcome by the filter device shown in FIG. 26, because the filter compression rings provide a 360° compression seal for filter elements 80, 81, and 82, and for filter elements 80a, 81a, and 82a, and because the filter compression rings are press fitted into body 101, unfiltered blood can not flow between the outer wall 192 of the filter compression rings and body 101.

Referring to FIG. 22, with front outlet port 6 and back outlet port 6a at the very bottom of center vertical channels 5 and 5a respectively, the length of link port 11 is minimized, thereby minimizing the diameter of the pin (a minimum diameter is needed to prevent breakage of the pin) in the injection mold, thereby minimizing the wall thickness of the center section of body 101, thereby reducing the cost of body 101.

A fourth embodiment of the filtration device constructed in accordance with the principles of the present invention, could be constructed by replacing the back cover 130 of the third embodiment with a second front cover 120. The fourth embodiment would work the same as the third embodiment, with the exception that after the feed blood bag is empty, air would enter first chamber 45 from the vent filter on the front cover 120 that replaces the back cover 130.

Figure 17:
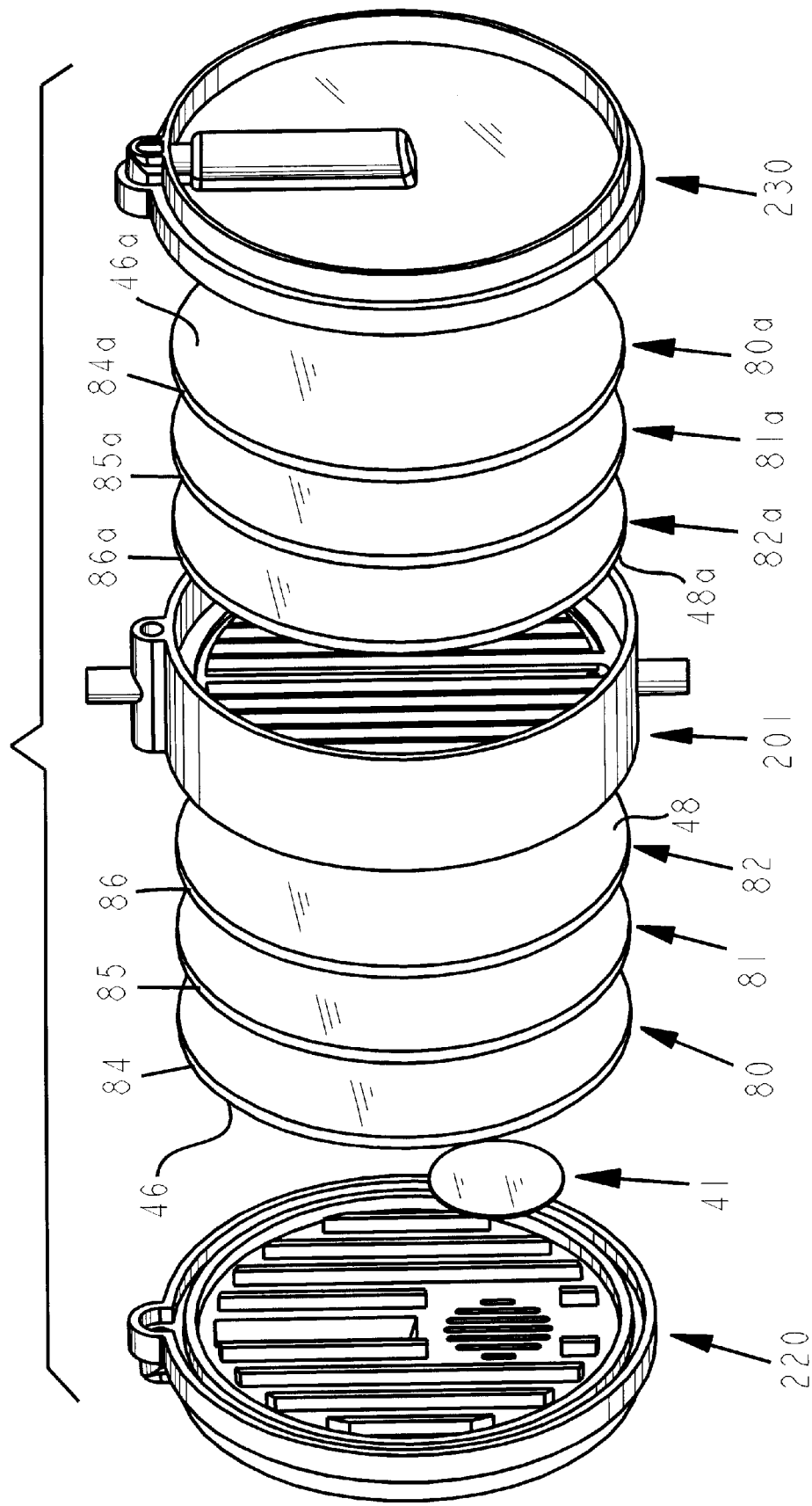
FIG. 17 is an exploded isometric view of the of the components that comprise the fifth embodiment of the filtration apparatus, constructed in accordance with the principles of the present invention, usable for the gravity filtration of blood and blood products.

A fifth embodiment of the filtration device constructed in accordance with the principles of the present invention, is shown in FIG. 10A through FIG. 20. Referring to FIG. 17 this embodiment includes the following major components: front cover 220, body 201, back cover 230, filter elements 80, 81, 82, 80a, 81a, and 82a, and hydrophobic vent filter element 41.

Figure 11:
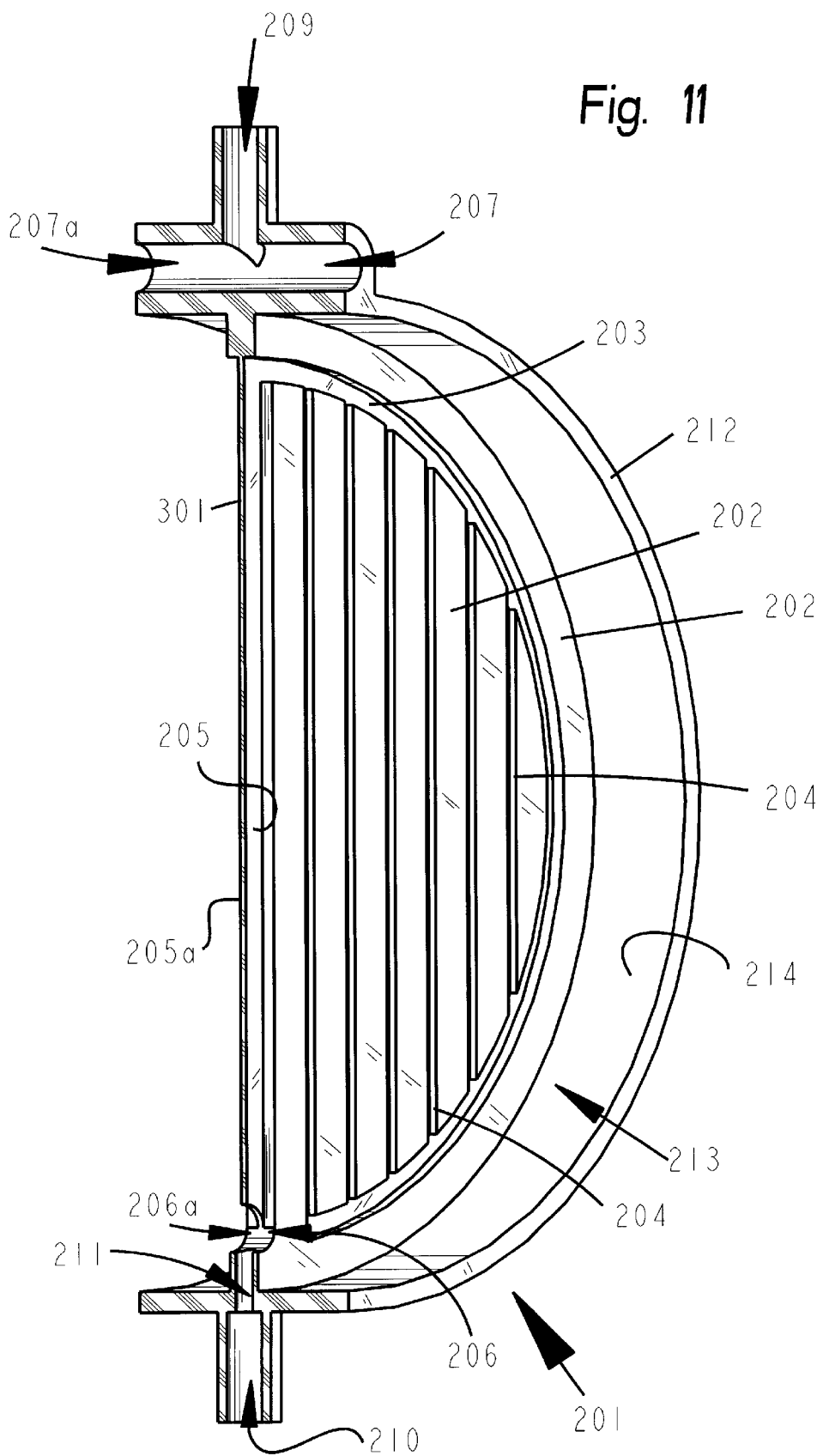
FIG. 11 is a front isometric view having portions thereof removed of the body of the filtration apparatus depicted in FIG. 17.

FIG. 10A, FIG. 11, and FIG. 12A show the front part of body 201. The front part of body 201 contains a first filter well 213, defined by flat surface 202 of partition wall 301 and cylindrical surface 214. The front part of body 201 also contains side vertical channels 204, circular channel 203, and center vertical channel 205. Preferably circular channel 203 is wider and deeper than side vertical channels 204, and center vertical channel 205 is wider than circular channel 203, and the same depth as circular channel 203. The upper and lower ends of side vertical channels 204 are in fluid flow relation with circular channel 203, and circular channel 203 is in fluid flow relation with center vertical channel 205. Center vertical channel 205 is in fluid flow relation with front outlet port 206. The upper central part of body 201 contains inlet tube socket 217, and cross protrusion 219. Inlet tube socket 217 contains inlet port 209, and cross protrusion 219 contains a cross port, with the front half of the cross port labeled front cross port 207, and the back half of the cross port labeled back cross port 207a. The lower central part of body 201 contains outlet tube socket 218. Outlet tube socket 218 contains outlet port 210. Front outlet port 206 is in fluid flow relation with outlet port 210 through link port 211.

FIG. 10B, and FIG. 12B show the back part of body 201. The back part of body 201 contains a second filter well 213a, defined by flat surface 202a of partition wall 301 and cylindrical surface 214a. The back part of body 201 also contains side vertical channels 204a, circular channel 203a, and center vertical channel 205a. Preferably circular channel 203a is wider and deeper than side vertical channels 204a, and center vertical channel 205a is wider than circular channel 203a, and the same depth as circular channel 203a. The upper and lower ends of side vertical channels 204a are in fluid flow relation with circular channel 203a, and circular channel 203a is in fluid flow relation with center vertical channel 205a. Center vertical channel 205a is in fluid flow relation with back outlet port 206a. The upper central part of body 201 contains inlet tube socket 217, and cross protrusion 219. Inlet tube socket 217 contains inlet port 209, and cross protrusion 219 contains a cross port, with the front half of the cross port labeled front cross port 207, and the back half of the cross port labeled back cross port 207a. The lower central part of body 201 contains outlet tube socket 218. Outlet tube socket 218 contains outlet port 210. Back outlet port 206a is in fluid flow relation with outlet port 210 through link port 211. Front outlet port 206 is a through hole with the front half labeled front outlet port 206, and the back half labeled back outlet port 206a. As shown in FIG. 10A, FIG. 10B, FIG. 12A and FIG. 12B the back part of body 201 is a mirror image of the front part of body 201. Body 201 is preferably made from an injection moldable medical grade plastic such acrylic, polycarbonate, polysulfone, polypropylene, polyethylene, but is not limited to these materials.

Figure 14:
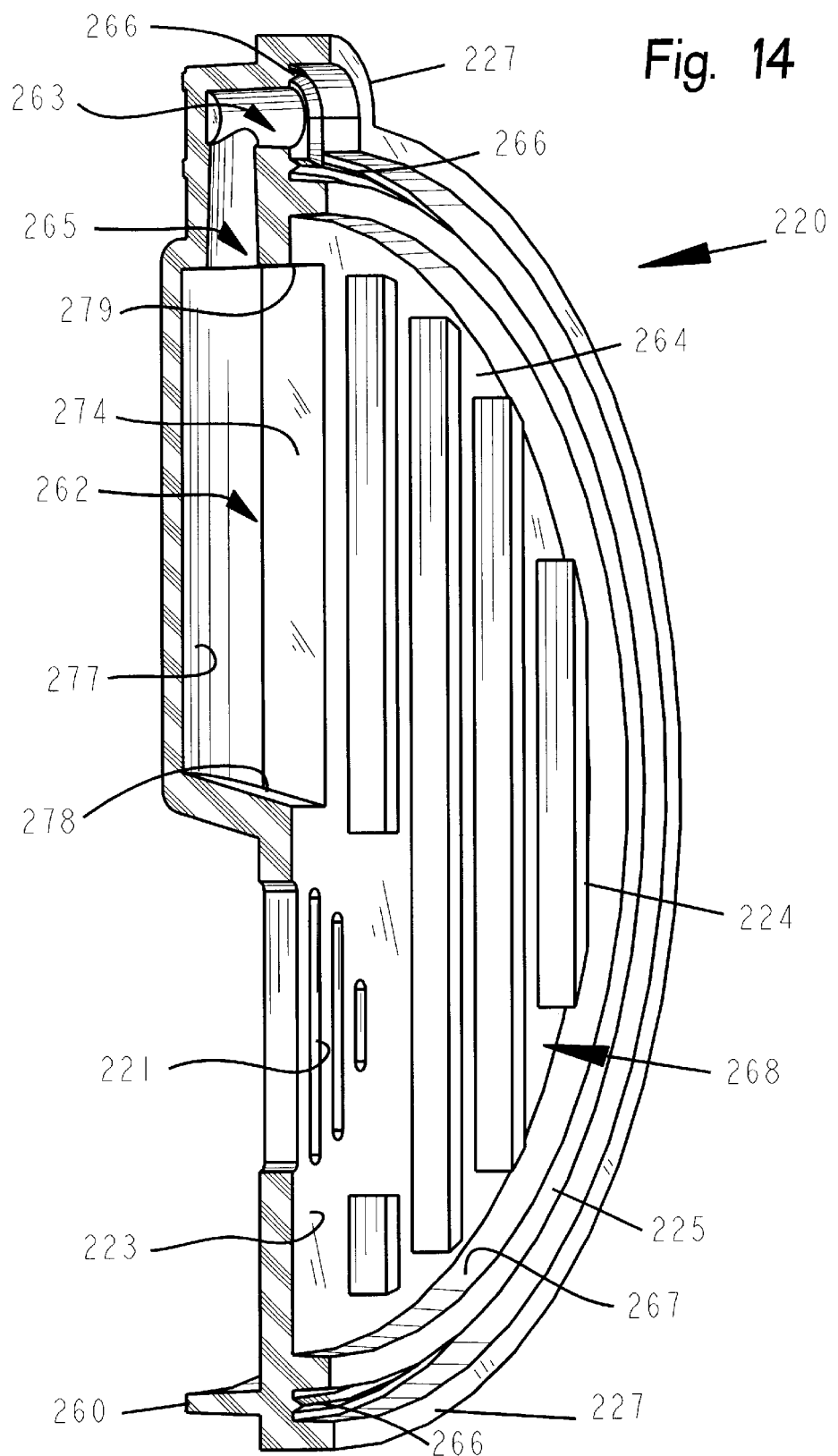
FIG. 14 is a front isometric view having portions thereof removed of the front cover of the filtration apparatus depicted in FIG. 17.
Figure 18:
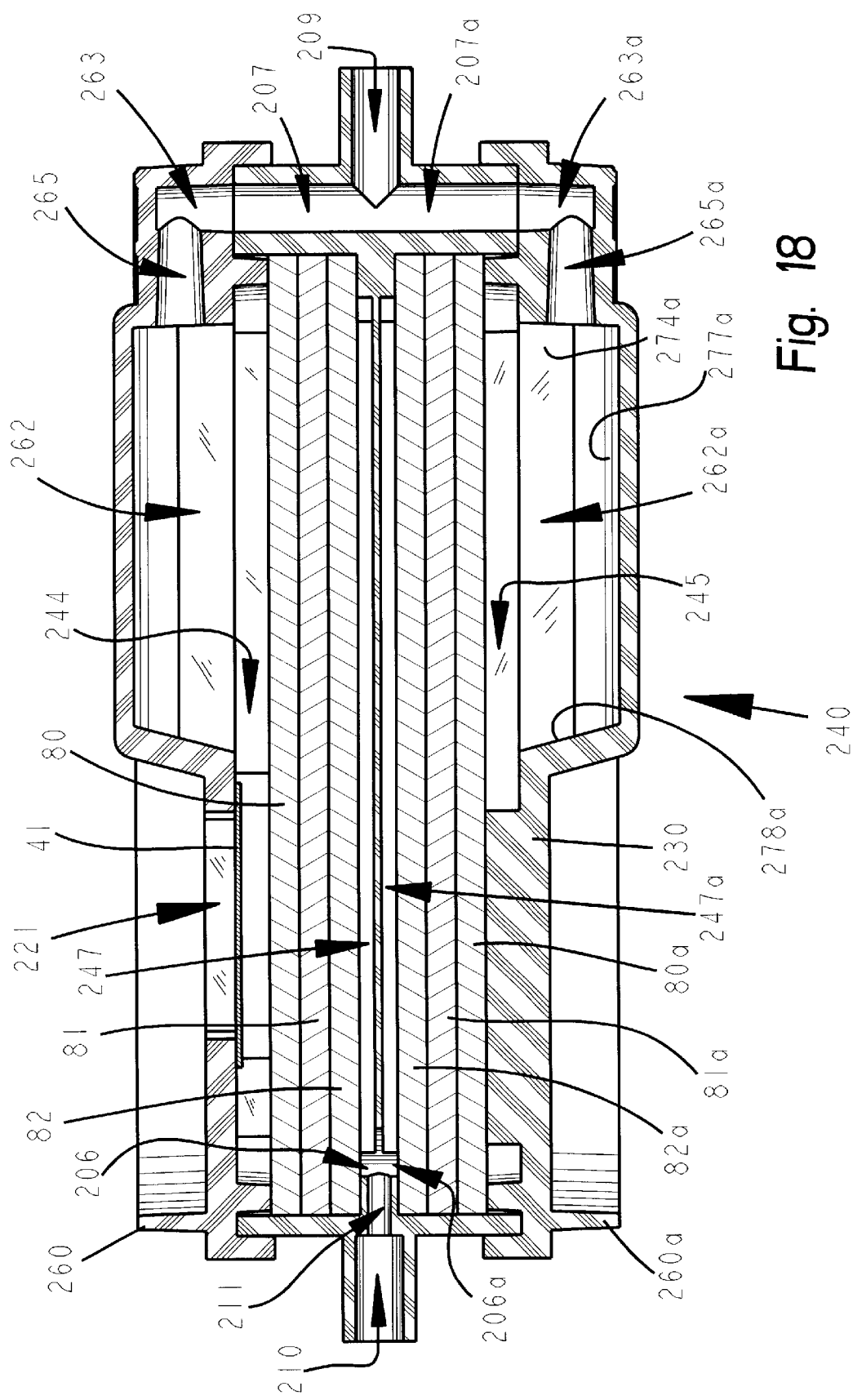
FIG. 18 is a cross-sectional view of the filtration apparatus depicted in FIG. 17.

FIG. 13A, FIG. 13B, and FIG. 14 show front cover 220. Front cover 220 is round in shape to match the shape of body 201, (if body 201 was square, then front cover 220 would also be square) and contains boss 229 at its upper end. The interior of front cover 220 contains flat surface 223. Vertical filter support ribs 224 protrude from flat surface 223. The vertical filter support ribs 224 could be replaced with ribs oriented in a direction other than vertical, or with a pattern of round pins, or with a pattern or rectangular pins, or with a pattern of concentric rings with gaps in the rings, or with any other filter support means that does not contain a closed loop. Outer rib 227 also protrudes from flat surface 223 and follows the outer periphery of front cover 220. Although it is not necessary for front cover 220 to contain outer rib 227, outer rib 227 acts as an alignment rib during assembly, and as a flash trap to contain flash when front cover 220 is assembled to body 201. Front cover 220 also contains round filter support rib 225. Round filter support rib 225 does not contain a gap, as round filter support rib 25 of front cover 20 of the first embodiment does. Front cover 220 also contains through slots 221, and vent filter bonding area 228. Although filter bonding area 228 is shown round for bonding a round vent filter, the vent filter could be square or any other shape, and then the filter bonding area 228 would conform to the shape of the vent filter. Through slots 221 are shown as vertical slots, they could be replaced by a pattern of round holes, or a pattern of square holes, or any other pattern of through holes that provide adequate filter support, and also provide air flow communication between the face of the vent filter that is bonded to flat surface 223, and to the outside atmosphere of front cover 220. Referring to FIG. 13B, FIG. 14, and FIG. 18, front cover 220 contains chamber 262 bounded by side walls 274, top wall 277, end wall 278, and end wall 279. Front cover 220 also contains port 263 and port 265. Port 263 is in fluid flow and air flow communication with chamber 262 through port 265. Referring to FIG. 14, front cover 220 contains energy director 266 if it is desired to bond front cover 220 to body 201 using an energy director ultrasonic weld. FIG. 18 shows vent filter element 41 bonded to front cover 220. Referring to FIG. 16, centerline 270 shows the center of the seal between front cover 220 and body 201. The seal could be an ultrasonic weld, a glue bond, a heat bond, a solvent bond, or any other type of leak tight bond. Referring to FIG. 13A, the outside of front cover 220 contains flat surface 222. Front cover 220 also contains weld rib 260 which protrudes above flat surface 222. The centerline of weld rib 260 is a mirror image of centerline 270, the center of the seal between front cover 220 and body 201. The outside of front cover 220 also contains protrusion 261, the outer wall of chamber 262 and port 265. Weld rib 260 is used to transmit sonic energy from a flat ultrasonic horn to energy director 266 (shown in FIG. 14) of front cover 220 during the process of welding front cover 220 to body 201, when an ultrasonic weld is used. Front cover 220 is preferably made from an injection moldable medical grade plastic such acrylic, polycarbonate, polysulfone, polypropylene, polyethylene, but is not limited to these materials. Front cover 220 is preferably made from the same material that body 201 is made of.

Figure 15B:
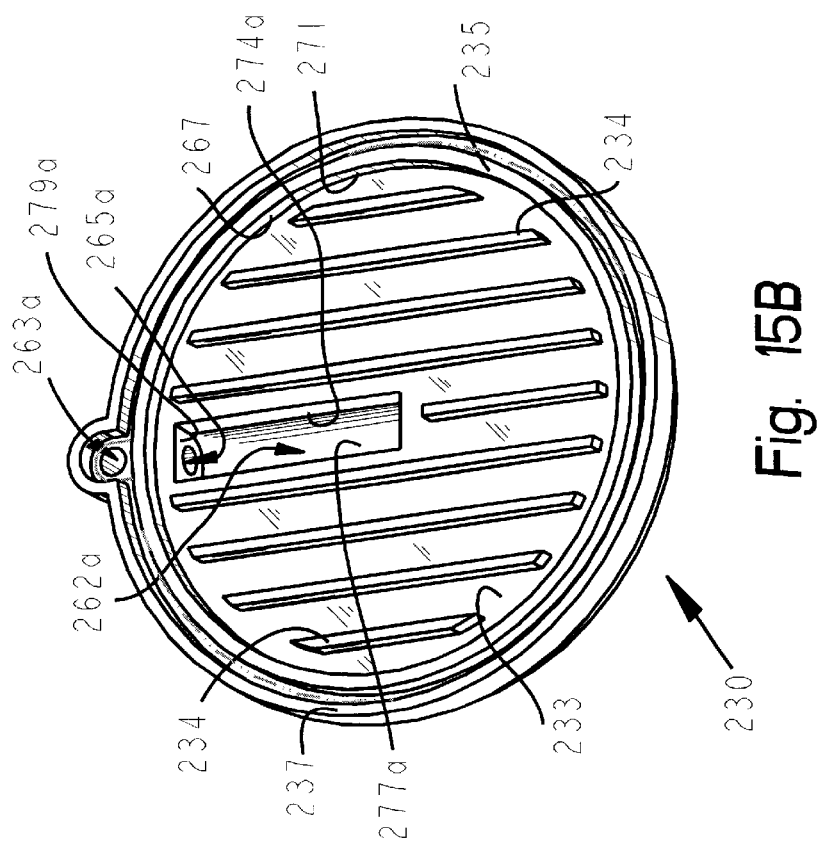
FIG. 15B is a back isometric view of the back cover of the filtration apparatus depicted in FIG. 17.
Figure 15A:
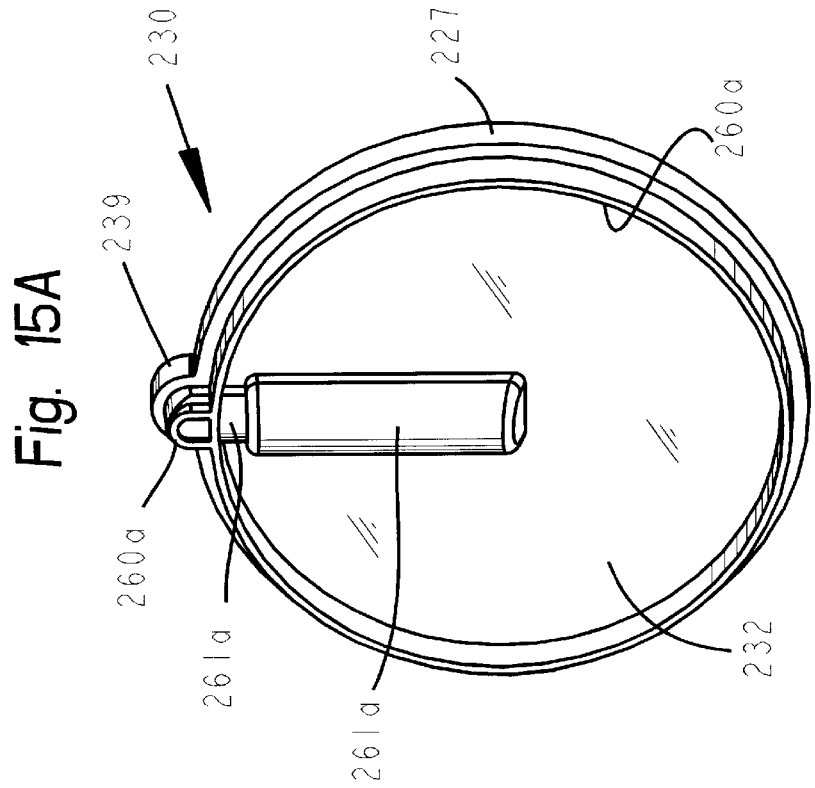
FIG. 15A is a front isometric view of the back cover of the filtration apparatus depicted in FIG. 17.

FIG. 15A, and FIG. 15B, show back cover 230. Back cover 230 is round in shape to match the shape of body 201, (if body 201 was square, then back cover 230 would also be square) and contains boss 239 at its upper end. The interior of back cover 230 contains flat surface 233. Vertical filter support ribs 234 protrude from flat surface 233. The vertical filter support ribs 234 could be replaced with ribs oriented in a direction other than vertical, or with a pattern of round pins, or with a pattern or rectangular pins, or with a pattern of concentric rings with gaps in the rings, or with any other filter support means that does not contain a closed loop. Outer rib 237 also protrudes from flat surface 233 and follows the outer periphery of back cover 230. Although it is not necessary for back cover 230 to contain outer rib 237, outer rib 237 acts as an alignment rib during assembly, and as a flash trap to contain flash when back cover 230 is assembled to body 201. Back cover 230 also contains round filter support rib 235. Round filter support rib 235 does not contains a gap, as round filter support rib of back cover 30 of the first embodiment does. Referring to FIG. 15A, FIG. 15B, and FIG. 18, back cover 230 contains chamber 262a bounded by side walls 274a, top wall 277a, end wall 278a, and end wall 279a. Back cover 230 also contains port 263a and port 265a. Port 263a is in fluid flow and air flow communication with chamber 262a through port 265a. Back cover 230 also contains an energy director 266a (not shown, like energy director 266 of front cover 220) if it is desired to bond back cover 230 to body 201 using an energy director ultrasonic weld. Back cover 230 seals to body 201 along a center line like centerline 270 shown in FIG. 16 for front cover 220. The seal could be an ultrasonic weld, a glue bond, a heat bond, a solvent bond, or any other type of leak tight bond. Referring to FIG. 15A, the outside of back cover 230 contains flat surface 232. Back cover 230 also contains weld rib 260a which protrudes above flat surface 232. The centerline of weld rib 260a is a mirror image of centerline 270, the center of the seal between back cover 230 and body 201. The outside of back cover 230 also contains protrusion 261a, the outer wall of chamber 262a and port 265a. Weld rib 260a is used to transmit sonic energy from a flat ultrasonic horn to energy director 266a of back cover 230 during the process of welding back cover 230 to body 201, when an ultrasonic weld is used. Back cover 230 is preferably made from an injection moldable medical grade plastic such acrylic, polycarbonate, polysulfone, polypropylene, polyethylene, but is not limited to these materials. Back cover 230 is preferably made from the same material that body 201 is made of. Back cover 230 is identical to front cover 220 with the exception that back cover 230 does not contain a vent filter.

Figure 19:
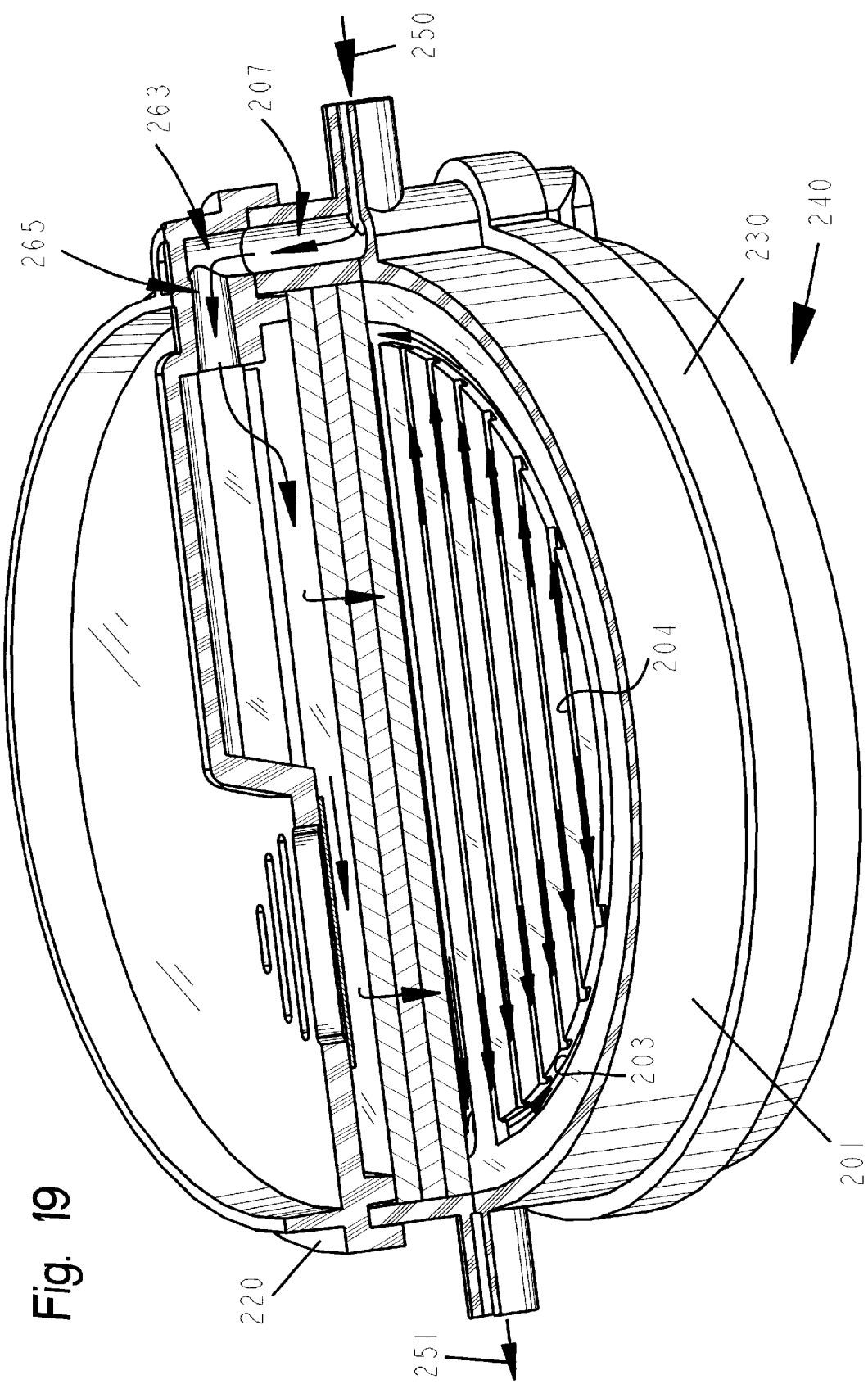
FIG. 19 is an isometric view of the filtration apparatus depicted in FIG. 17, having portions thereof removed.

FIG. 17 shows an exploded view of the components that comprise filter device 240. The components are body 201, front cover 220, back cover 230, vent filter element 41, and filter elements 80, 81, and 82, and filter elements 80a, 81a, and 82a. FIG. 18 and FIG. 19 show filter device 240 in the assembled state. Referring to FIG. 10A, FIG. 10B, FIG. 11, FIG. 13B, FIG. 14 FIG. 15B, FIG. 16, FIG. 17, FIG. 18, and FIG. 19, the components that comprise filter device 240 are assembled as follows. The outer periphery of vent filter element 41 is sealed to front cover 220 at filter bonding area 228. The seal is preferably a heat seal but could be an ultrasonic seal, a glue bond, a solvent bond, or any other type of bond that will produce a leak tight seal capable of maintaining sterility. Filter element 41 is a hydrophobic filter with a pore size of 0.2 μ or smaller to maintain sterility. Filter elements 80, 81, and 82 are placed into first filter well 213. Front cover 220 is then bonded to body 201 so that edge 212 of body 201 is bonded to front cover 220 along centerline 270 shown in FIG. 16. The seal between front cover 220 and body 201 forms a double closed loop. The first closed loop encloses the outer periphery of first filter well 213 of body 201, thereby creating a closed first chamber 244 in first filter well 213. The second closed loop encloses the outer periphery of front cross port 207, and the outer periphery of port 263, thereby creating a flow path from inlet port 209, through front cross port 207, through port 263, through port 265, into chamber 262, into first chamber 244 of first filter well 213. If first chamber 244 is made deeper chamber 262 may be eliminated, and the flow path would flow from inlet port 209, through port 263, through port 265, into first chamber 244. Outer rib 227 of front cover 220 aligns front cover 220 to body 201 during the assembly procedure and also acts as a flash trap. The bond between front cover 220 and body 201 is preferably an ultrasonic seal but could be a glue bond, a heat bond, a solvent bond or any other type of bond that creates a leak tight seal. Filter elements 80, 81, and 82 are sealed to body 201 with a compression seal between the outer edges 84, 85, and 86 of filter elements 80, 81, and 82 respectively, and cylindrical surface 214 of body 201 in the filter device 240 shown. This seal could be augmented or replaced by a compression seal created by compressing the outer periphery of filter elements 80, 81, and 82 between round filter support rib 225 of front cover 220 and flat surface 202 of body 201. Filter elements 80, 81, and 82 also could be sealed to body 201 with a glue seal, a heat seal, or any other type of seal that eliminates bypass around filter elements 80, 81, and 82. Filter device 240 is shown with 3 filter elements 80, 81, and 82 in first filter well 213. However any number of filter elements greater than or equal to one could be used. The number of filter elements used is determined by the filter type and the fluid being filtered. The same number of filter elements that were placed into first filter well 213 of body 201 are now placed into second filter well 213a of body 201, and are designated as filter elements 80a, 81a, and 82a. These filter elements are sealed to body 201 using the same method that was used to seal filter elements 80, 81, and 82 to first filter well 213. Back cover 230 is then bonded to body 201 so that edge 212a of body 201 is bonded to back cover 230 along the same path as centerline 270 shown in FIG. 16. The seal between back cover 230 and body 201 forms a double closed loop. The first closed loop encloses the outer periphery of second filter well 213a of body 201, thereby creating a closed first chamber 245 in second filter well 213a. The second closed loop encloses the outer periphery of back cross port 207a, and the outer periphery of port 263a, thereby creating a flow path from inlet port 209, through back cross port 207a, through port 263a, through port 265a, into chamber 262a, into first chamber 245 of second filter well 213a. If first chamber 245 is made deeper chamber 262a may be eliminated, and the flow path would flow from inlet port 209, through back cross port 207a, through port 263a, through port 265a, into first chamber 245. Outer rib 237 of back cover 230 aligns back cover 230 to body 201 during the assembly procedure and also acts as a flash trap. The bond between back cover 230 and body 201 is preferably an ultrasonic seal but could be a glue bond, a heat bond, a solvent bond or any other type of bond that creates a leak tight seal.

Referring to FIG. 13B, FIG. 17, FIG. 18, and FIG. 19, the assembled filter device 240 contains first chamber 244 bounded by flat surface 223 of front cover 220, inner surface 277 of round filter support rib 225 of front cover 220, and the upstream surface 46 of the first filter element 80 in first filter well 213 of body 201. Referring to FIG. 15B, FIG. 17, and FIG. 18, the assembled filter device 240 also contains first chamber 245 bounded by flat surface 233 of back cover 230, inner surface 271 of round rib 235 of back cover 230, and the upstream surface 46a of the first filter element 80a in second filter well 213a of body 201. Referring to FIG. 18, in the assembled filter device 240, front cross port 207 of body 201 is in fluid flow communication and air flow communication with first chamber 244 through port 263, port 265, and chamber 262 of front cover 220. Referring to FIG. 18, in the assembled filter device 240, back cross port 207a of body 201 is in fluid flow communication and air flow communication with first chamber 245 through port 263a, port 265a, and chamber 262a of back cover 220.

Referring to FIG. 10a, FIG. 14, FIG. 17 and FIG. 18, the assembled filter device 240 contains second chamber 247 of first filter well 213 bounded by the downstream surface 48 of the last filter element 82 in first filter well 213 of body 201, and by center vertical channel 205, circular channel 203, and side vertical channels 204. Second chamber 247 of first filter well 213 contains front outlet port 206. Referring to FIG. 10b, FIG. 17 and FIG. 18, the assembled filter device 240 contains second chamber 247a of second filter well 213a bounded by the downstream surface 48a of the last filter element 82a in second filter well 213a of body 201, and by center vertical channel 205a, circular channel 203a, and side vertical channels 204a. Second chamber 247a of second filter well 213a contains back outlet port 206a.

Figure 20:
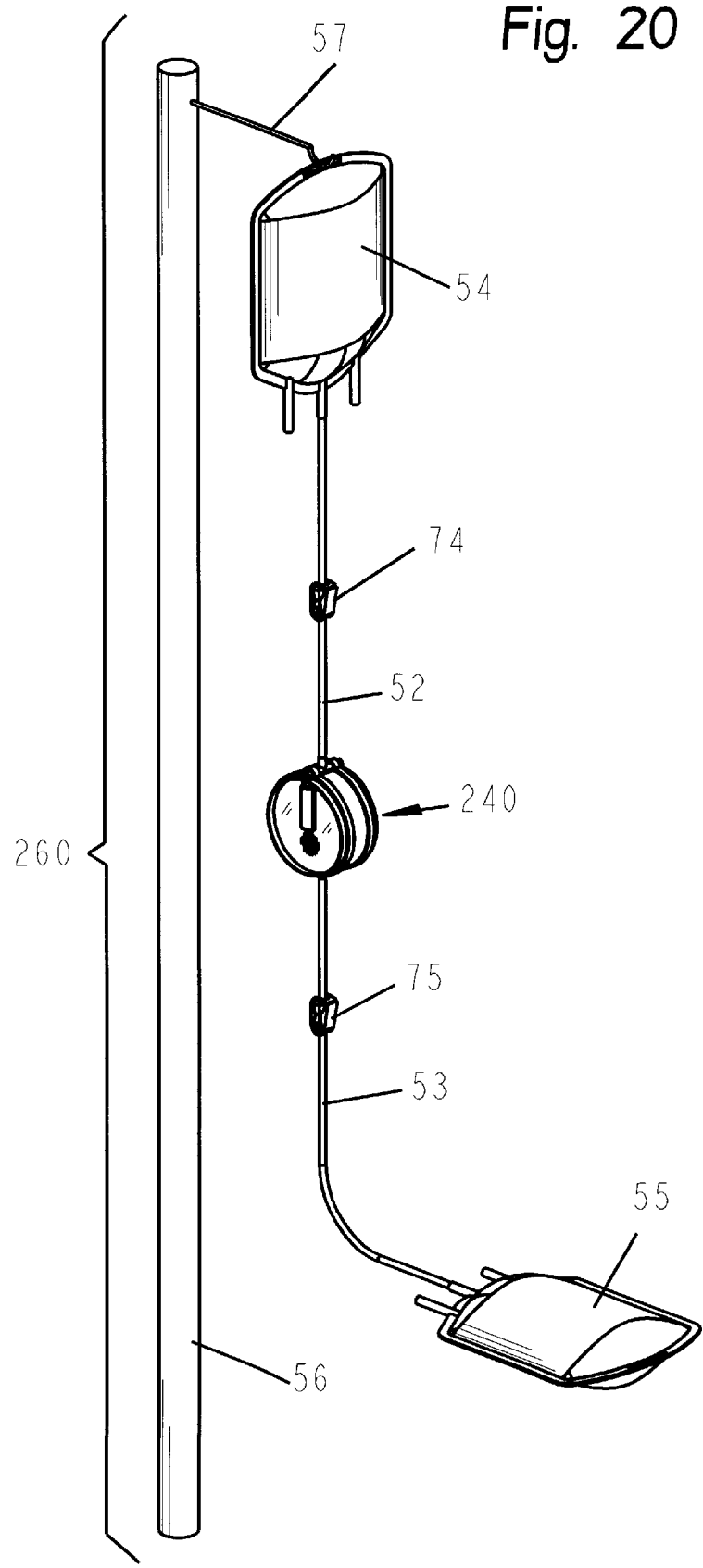
FIG. 20 is an isometric view of a blood filtration assembly containing the filtration apparatus depicted in FIG. 17.

Referring to FIG. 20 one end of a length of outlet tubing 53 is bonded to outlet tube socket 218 of body 201, with the other end of said outlet tubing bonded to an empty blood bag 55. Another length of inlet tubing 52 is bonded to inlet tube socket 217 of body 201. The end user will purchase the assembly of filter device 240, inlet tubing 52, outlet tubing 53, and receiving blood bag 55, assembled and sterile. The assembly will also contain an inlet tubing clamp 74 on inlet tubing 52, and an outlet tubing clamp 75 on outlet tubing 53.

In FIG. 20 the filter device 240 is in an operational assembly with inlet tubing 52, outlet tubing 53, feed blood bag 54, receiving blood bag 55, inlet tube clamp 74, and outlet tube clamp 75. Preferably, the user will purchase the assembly of FIG. 20 sterilized without feed blood bag 54 with the inlet end of inlet tubing 52 sealed to maintain system sterility. For performing filtration the user will first close inlet tube clamp 74 close to the inlet end of inlet tubing 52. Next the user will make sure that outlet tube clamp 75 is open. Inlet tubing 52 is now bonded by the user to a pigtail on feed blood bag 54 using a sterile docking device as is well known in the art.

Once the sterile docking connection is made the user will hang feed blood bag 54 from hook 57 on blood bag pole 56. Receiving blood bag 55 should be placed on a surface such as a table top or the like. The complete assembly 260 ready for filtration is illustrated in FIG. 20.

Referring to FIG. 10A, FIG. 10B, FIG. 18, FIG. 19 and FIG. 20 the filtration is performed as follows. The user opens inlet tube clamp 74. Gravity now forces blood to flow from feed blood bag 54, through inlet tubing 52, through inlet port 209 of body 201. After passing through inlet port 209, a portion of the blood passes through front cross port 207, while the remainder of the blood passes through back cross port 207a. The portion of the blood that passes through front cross port 207, then passes through port 263, through port 265, into chamber 262, and then into first chamber 244. The portion of the blood that passes through back cross port 207a, then passes through port 263a, through port 265a, into chamber 262a, and then into first chamber 245. A portion of the air that was in inlet tubing 52 and inlet port 209 before blood flow started will be pushed ahead of the blood, through front cross port 207, through port 263, through port 265, into chamber 262, and then into first chamber 244. The remainder of the air that was in inlet tubing 52 and inlet port 9 before blood flow started will be pushed ahead of the blood, through back cross port 207a, through port 263a, thorough port 265a, into chamber 262a, and then into first chamber 245. Because the usable surface area of hydrophobic filter 41 is much smaller than the usable surface area of filter elements 80, 81, and 82; and because the pressure drop across sterilizing grade hydrophobic filter 41 is much greater per unit volume of air flow per unit surface area of filter material than the combined pressure drop across filter elements 80, 81, and 82 per unit volume of air flow per unit surface area of filter material, only a very small portion of the air that was in inlet tubing 52, inlet port 9, front cross port 207, port 263, and port 265 before blood flow started, will pass through hydrophobic filter 41, and then through slots 221 of front cover 220 to atmosphere.

As first chamber 244 fills from the bottom up most of the air in first chamber 244 and in chamber 262 will be forced through filter elements 80, 81, and 82, for the same reasons described in the previous paragraph. This initial air will flow into vertical channels 204, circular channel 203, and center vertical channel 205, and then flow through front outlet port 206, through link port 211, through outlet port 210, into outlet tubing 53, into receiving blood bag 55. Filter elements 80, 81, and 82 will also wet from the bottom up. The air that is initially in filter elements 80, 81, and 82 will be displaced by blood and flow into vertical channels 204, circular channel 203, and center vertical channel 205, and then flow through front outlet port 206, through link port 211, through outlet port 210, into outlet tubing 53, into receiving blood bag 55. Because the combined volume of first chamber 244 and chamber 262 is small, and the flow rate of blood entering first chamber 244 is much greater than the initial flow rate of blood through filter elements 80, 81, and 82, first chamber 244 will fill in a small fraction of the time that it takes to wet filter elements 80, 81, and 82. The pressure head at the bottom of first chamber 244 will be larger than the pressure head at the top of chamber 244, because of the height difference between the top and bottom of first chamber 244. Therefore liquid will start to come through filter element 82 from the bottom up. As liquid starts to come through filter element 82 from the bottom up vertical channels 204, circular channel 203, and center vertical channel 205, of body 201 will fill from the bottom up. Because the total volume of these channels in is small (to minimize holdup) the channels may fill with blood (from the bottom up) before the upper part of filter element 82 has wet with blood. Once blood starts to flow from center vertical channel 205 of body 201, into front outlet port 206 of body 201, through link port 211 of body 201, into outlet tubing 53, and starts to flow down outlet tubing 53 toward receiving blood bag 55, the pressure in front outlet port 206 will become negative. Because center vertical channel 205 is in fluid flow relationship with front outlet port 206, the pressure inside the tube created by center vertical channel 205 and downstream surface 48 of filter element 82 will also be negative. Likewise since circular channel 203 is in fluid flow relationship with center vertical channel 205 the pressure inside the tube created by circular channel 203 and downstream surface 48 of filter element 82 will also be negative. Since the tube segments made up of vertical channels 204 and downstream surface 48 of filter element 82 are in fluid flow relationship with the tube created by circular channel 203 and downstream surface 48 of filter element 82, any air or liquid that flows from filter element 82 into vertical channels 204 will be sucked into circular channel 203, and then flow from circular channel 203 into center vertical channel 205, through front outlet port 206, through link port 211, through outlet port 210, into outlet tubing 53, and into receiving blood bag 55. This assures that filter elements 80, 81, and 82 will completely wet, and that all of the air that was in first chamber 244 and chamber 262, filter elements 80, 81, and 82, vertical channels 204, circular channel 203, center circular channel 205, front outlet port 206, link port 211, outlet port 210, and the interior of outlet tubing 53 will be forced into receiving blood bag 55. Although vertical channels 204 are shown in the vertical orientation, they could be orientated at any angle from zero degrees to ninety degrees from vertical, as long as they are in fluid flow relationship with circular channel 3. Other channel designs such as the spiral channel filter underdrain disclosed in U.S. Ser. No. 08/524,049, U.S. Pat. No. 5,798,041, and entitled "an In-Line Liquid Filtration Device Usable for Blood, Blood Products and the Like", could also be used in place of the design illustrated in FIG. 10A. It is however, imperative that all channels be either directly or indirectly in fluid flow relationship with front outlet port 206.

The portion of blood from feed blood bag 54 which flows through back cross port 7a, through port 263a, through port 265a, into chamber 262a, into first chamber 245, will fill first chamber 245 from the bottom up forcing all of the air in first chamber 45 and chamber 262a through filter elements 80a, 81a, and 82a. This initial air will flow into vertical channels 204a, circular channel 203a, and center vertical channel 205a, and then flow through back outlet port 206a, through link port 211, through outlet port 210, into outlet tubing 53, into receiving blood bag 55. Filter elements 80a, 81a, and 82a will also wet from the bottom up. The air that is initially in filter elements 80a, 81a, and 82a will be displaced by blood and flow into vertical channels 204a, circular channel 203a, and center vertical channel 205a, and then flow through outlet port 206a, through link port 211, through outlet port 210, into outlet tubing 53, into receiving blood bag 55. Because the combined volume of first chamber 245 and chamber 262a is small, and the flow rate of blood entering chamber 262a and first chamber 245 is much greater than the initial flow rate of blood through filter elements 80a, 81a, and 82a, first chamber 245 and chamber 262a will fill in a small fraction of the time that it takes to wet filter elements 80a, 81a, and 82a. The pressure head at the bottom of first chamber 245 will be larger than the pressure head at the top of first chamber 245, because of the height difference between the top and bottom of first chamber 245. Therefore liquid will start to come through filter element 82a from the bottom up. As liquid starts to come through filter element 82a from the bottom up vertical channels 204a, circular channel 203a, and center vertical channel 205a, of body 201 will fill from the bottom up. Because the total volume of these channels in is small (to minimize holdup) the channels may fill with blood (from the bottom up) before the upper part of filter element 82a has wet with blood. Once blood starts to flow from center vertical channel 205a of body 201, into back outlet port 206a of body 201, through link port 211 of body 201, into outlet tubing 53, and starts to flow down outlet tubing 53 toward receiving blood bag 55, the pressure in back outlet port 206a will become negative. Because center vertical channel 205a is in fluid flow relationship with back outlet port 206a, the pressure inside the tube created by center vertical channel 205a and the downstream surface 48a of filter element 82a will also be negative. Likewise since circular channel 203a is in fluid flow relationship with center vertical channel 205a the pressure inside the tube created by circular channel 203a and the downstream surface 48a of filter element 82a will also be negative. Since the tube segments made up of vertical channels 204a and the downstream surface 48a of filter element 82a are in fluid flow relationship with the tube created by circular channel 203a and the downstream surface 48a of filter element 82a, any air or liquid that flows from filter element 82a into vertical channels 204a will be sucked into circular channel 203a, and then flow from circular channel 203a into center vertical channel 205a, through back outlet port 206a, through link port 211, through outlet port 210, into outlet tubing 53, and into receiving blood bag 55. This assures that filter elements 80a, 81a, and 82a will completely wet, and that all of the air that was in chamber 245, chamber 262a, filter elements 80a, 81a, and 82a, vertical channels 204a, circular channel 203a, center vertical channel 205a, back outlet port 206a, link port 211, outlet port 210, and the interior of outlet tubing 53 will be forced into receiving blood bag 55. Although vertical channels 204a are shown in the vertical orientation, they could be orientated at any angle from zero degrees to ninety degrees from vertical, as long as they are in fluid flow relationship with circular channel 203a. Other channel designs such as the spiral channel filter underdrain disclosed in U.S. Ser. No. 08/524,049, U.S. Pat. No. 5,798,041, and entitled "an In-Line Liquid Filtration Device Usable for Blood, Blood Products and the Like", could also be used in place of the design illustrated in FIG. 10B. It is however, imperative that all channels be either directly or indirectly in fluid flow relationship with back outlet port 206a.

Blood filtration will continue until feed blood bag 54 is empty. When feed blood bag 54 is empty it will be collapsed and therefore close the inlet end of inlet tubing 52. Because outlet tubing 53 will be full of blood, and because the outside of receiving blood bag 55 is at atmospheric pressure, the pressure head in front outlet port 206, and the pressure head in back outlet port 206a will be negative, as will be the pressure head in vertical channels 204, circular channel 203, center vertical channel 205, vertical channels 204a, circular channel 203a, and center vertical channel 205a, all of body 201. Once blood flow has stopped the pressure drop across filter elements 80, 81, and 82, will fall to zero. The pressure drop across filter elements 80a, 81a, and 82a, will also fall to zero. Hence the pressure in first chamber 244 and chamber 262, and the pressure in first chamber 245 and chamber 262a will become negative. Once the pressure in chamber 244 and chamber 262 falls below atmospheric pressure air will begin to flow from atmosphere through slots 221, through sterilizing grade hydrophobic filter 41, into first chamber 244. The sterile air that enters first chamber 244 will bubble up to the top of first chamber 244 and chamber 262, thus causing first chamber 244 and chamber 262 to drain from the top down. Because of the negative pressure in first chamber 245, some of the air that bubbles to the top of first chamber 244 will pass through port 265, through port 263, through front cross port 207, through back cross port 207a, through port 263a, through port 265a, into chamber 262a and first chamber 245, causing chamber 262a and first chamber 245 to drain from the top down, and causing the blood in port 263 and port 265 to drain into chamber 262, and causing the blood in port 263a and port 265a to drain into chamber 262a, and causing the blood in front cross port 207 and back cross port 207a to drain into both chamber 262 and chamber 262a. Because the air entering first chamber 244 bubbles to the top of first chamber 244 and to the top of chamber 262, thus draining first chamber 244 and chamber 262 from the top down, vent filter element 41 can be located anywhere on flat surface 223 of front cover 220. Filter elements 80, 81, 82, 80a, 81a, and 82a will be plugged sufficiently at this point, therefore very little if any blood will be sucked from these filter elements by the negative pressure in front outlet port 206, and by the negative pressure in back outlet port 206a. Hence blood flow will stop after first chamber 244 and chamber 262, and after first chamber 245 and chamber 262a have drained and blood will remain in filter elements 80, 81, 82, 80a, 81a, and 82a, and in vertical channels 204, circular channel 203, center vertical channel 205, vertical channels 204a, circular channel 203a, and center vertical channel 205a, and in front outlet port 206, back outlet port 206a, link port 211, outlet port 210, all of body 201, and in outlet tubing 53.

The user can now close tube clamp 75 on outlet tubing 53 and then seal outlet tubing 53 above tube clamp 75, and then cut outlet tubing 53 above the seal just made. Feed blood bag 54, inlet tubing 52, and filter device 240 can now be discarded in a safe manner. Outlet tubing 53 will have segments marked on it. The user can now seal the tubing at the segment marks. The blood that is left in outlet tubing 53 will be used for cross matching and for quality control purposes.

Referring to FIG. 10A, FIG. 10B, FIG. 13B, FIG. 15B, and FIG. 18, front cover 220 and back cover 230 of filter device 240 provide a 360° continuous filter compression seal via round filter support rib 225 and round filter support rib 235 respectively. Because unfiltered blood enters chamber 262 and first chamber 244 on the inside of round filter support rib 225, unfiltered blood is prevented from entering the gap between the outside of round filter support rib 225 of front cover 220 and cylindrical surface 214 of body 201. Likewise, unfiltered blood enters chamber 262a and first chamber 245 on the inside of round filter support rib 235, thus unfiltered blood is prevented from entering the gap between the outside of round filter support rib 235 of back cover 230 and cylindrical surface 214a of body 201. Hence the fifth embodiment of the present invention overcomes the shortcomings of the first two embodiments of the present invention, with the added benefit that the two filter compression rings of the third embodiment are not required in the fifth embodiment.

Referring to FIG. 11, with front outlet port 206 and back outlet port 206a at the very bottom of center vertical channels 205 and 205a respectively, the length of link port 211 is minimized, thereby minimizing the diameter of the pin (a minimum diameter is needed to prevent breakage of the pin) in the injection mold, thereby minimizing the wall thickness of partition wall 301 of body 201, thereby reducing the cost of body 201.

A sixth embodiment of the filtration device constructed in accordance with the principles of the present invention, could be constructed by replacing the back cover 230 of the fifth embodiment with a second front cover 220. The sixth embodiment would work the same as the fifth embodiment, with the exception that after the feed blood bag is empty, air would enter first chamber 245 and chamber 262a from the vent filter on the front cover 220 that replaces the back cover 230.

Figure 29:
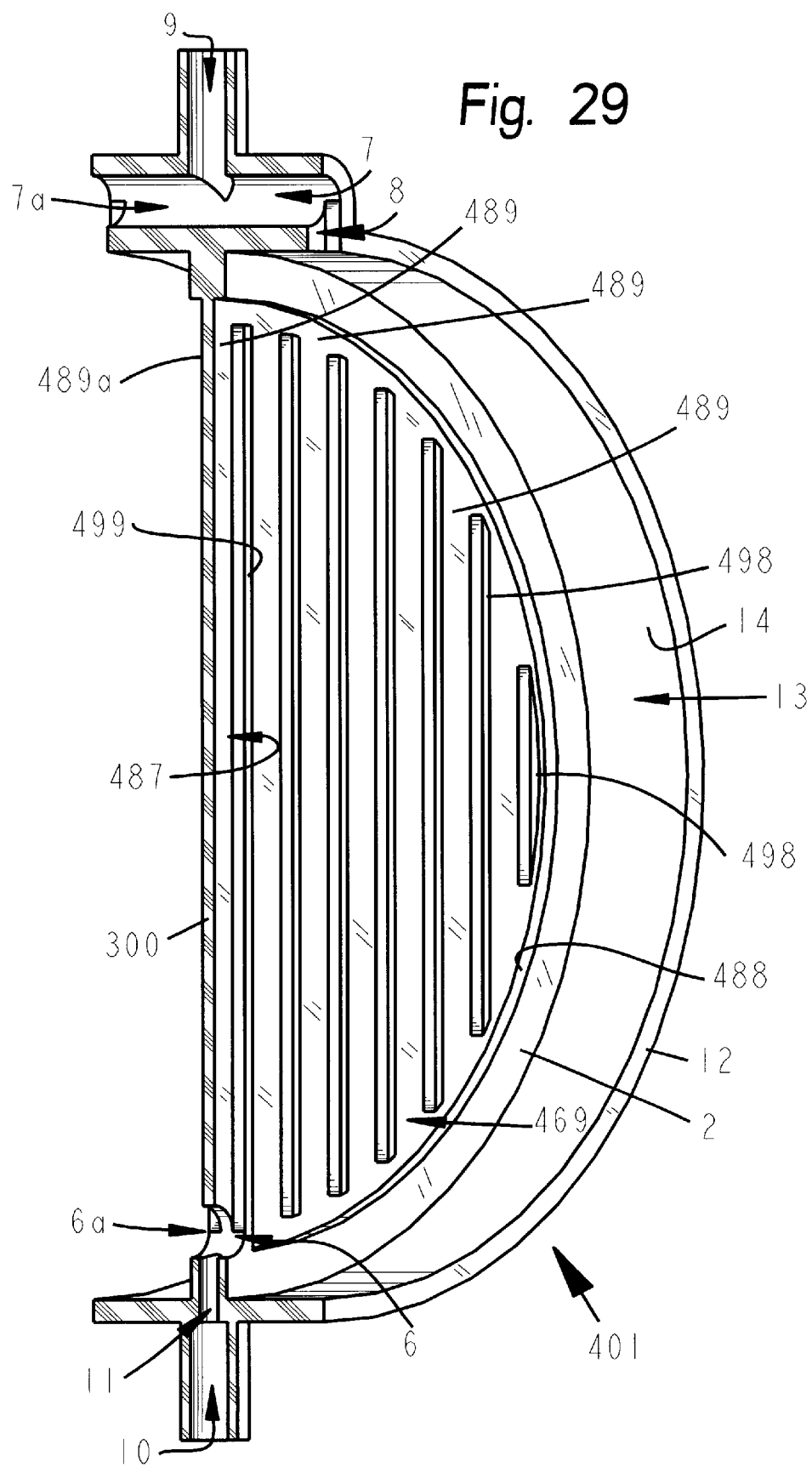
FIG. 29 is an isometric view, having portions thereof removed, of the body of the filtration apparatus depicted in FIG. 30.
Figure 30:
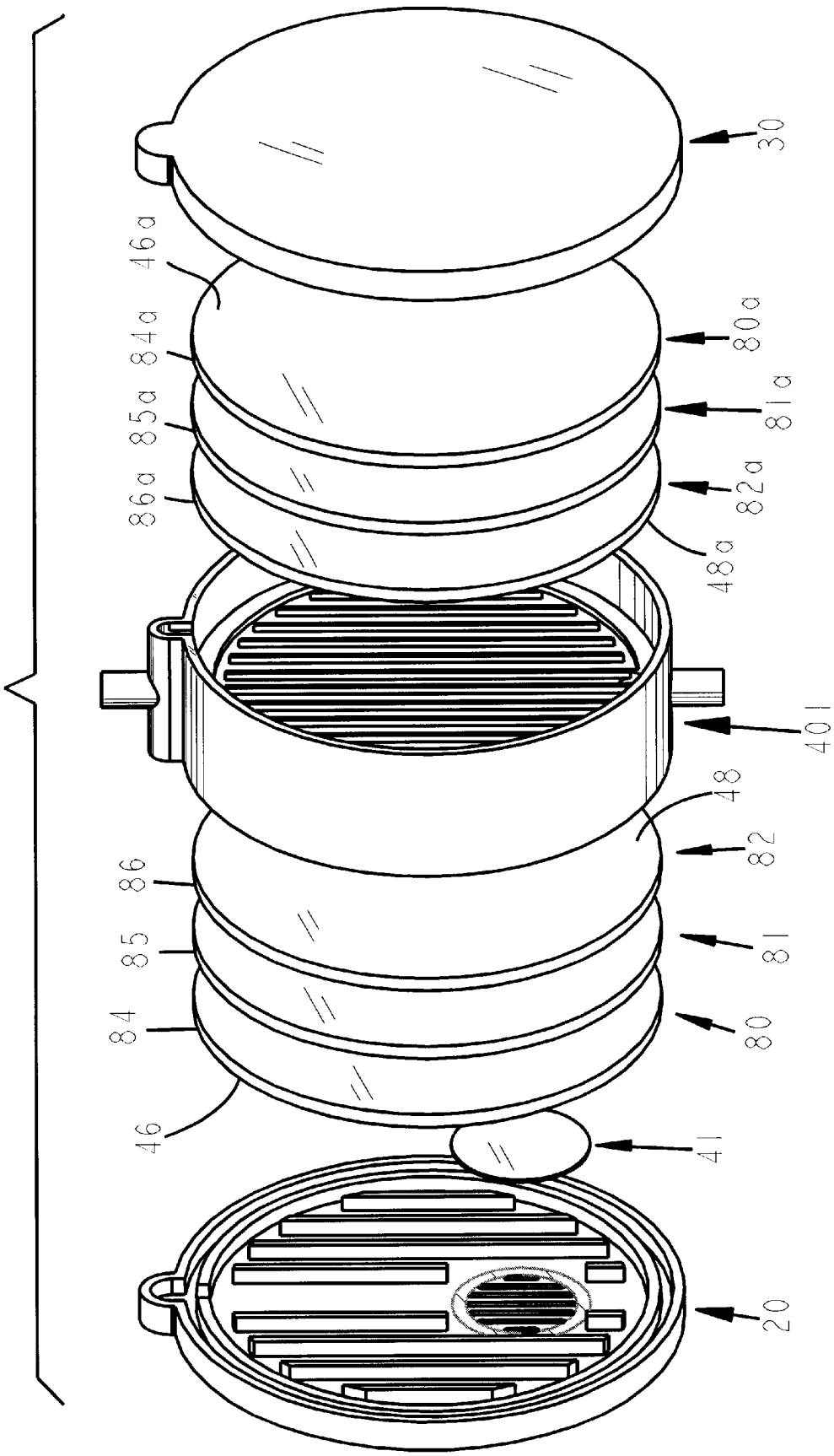
FIG. 30 is an exploded isometric view of the of the components that comprise the seventh embodiment of the filtration apparatus, constructed in accordance with the principles of the present invention, usable for the gravity filtration of blood and blood products.

A seventh embodiment of the filtration device constructed in accordance with the principles of the present invention, is shown in FIG. 28a, FIG. 28b, FIG. 29, FIG. 30, and FIG. 31. FIG. 30 shows an exploded view of the components that comprise filter device 440. Filter device 440 includes the following major components: front cover 20, body 401, back cover 30, filter elements 80, 81, 82, 80a, 81a, and 82a, and hydrophobic vent filter element 41. The only difference between filter device 40 of the first embodiment, shown in FIG. 6, and filter device 440 of the seventh embodiment, shown in FIG. 30, is that body 1 of the first embodiment is replaced with body 401 in the seventh embodiment.

Referring to FIG. 1, FIG. 2, FIG. 28a, FIG. 28b, and FIG. 29, body 401 is identical to body 1 with the following exceptions. Side vertical channels 4, circular channel 3, and center vertical channel 5 of front flat surface 2 of partition wall 300 of body 1 are eliminated from body 401. Referring to FIG. 28a and FIG. 29, the front part of body 401 replaces these components with well 469, defined by flat surface 489 of partition wall 300, and side wall 488 of partition wall 300. Vertical filter support ribs 498 protrude from flat surface 489 of partition wall 300. A gap must exist between the top of vertical filter support ribs 498 and side wall 488. The gap should small enough to provide the proper support for filter elements 80, 81, and 82, but large enough to allow liquid or gas to flow through the gap to the top of vertical channel 487. The top face of filter support ribs 498 should lie in the same plane as flat surface 2 of partition wall 300. Vertical filter support ribs 498 could be replaced with a pattern of round pins, or with a pattern or rectangular pins, or with any other filter support means that will allow air to bubble to the top of well 469. Body 401 contains two vertical filter support ribs 499 that are attached to side wall 488 at the bottom of side wall 488. A gap must exist between the top of vertical support ribs 499 and side wall 488. Vertical channel 487 is bounded by the side walls of vertical filter support ribs 499 adjacent to channel 487, and by flat surface 489. The bottom of vertical channel 487 is in fluid flow communication with outlet port 10 via link port 11 and front outlet port 6. The top of vertical channel 487 is open. Referring to FIG. 28b, the back face of partition wall 300 of body 401 is a mirror image of the front face of partition wall 300 of body 401 just described.

The components that comprise filter device 440 are assembled in the same manner as those of filter device 40 as described above for the first embodiment.

Figure 31:
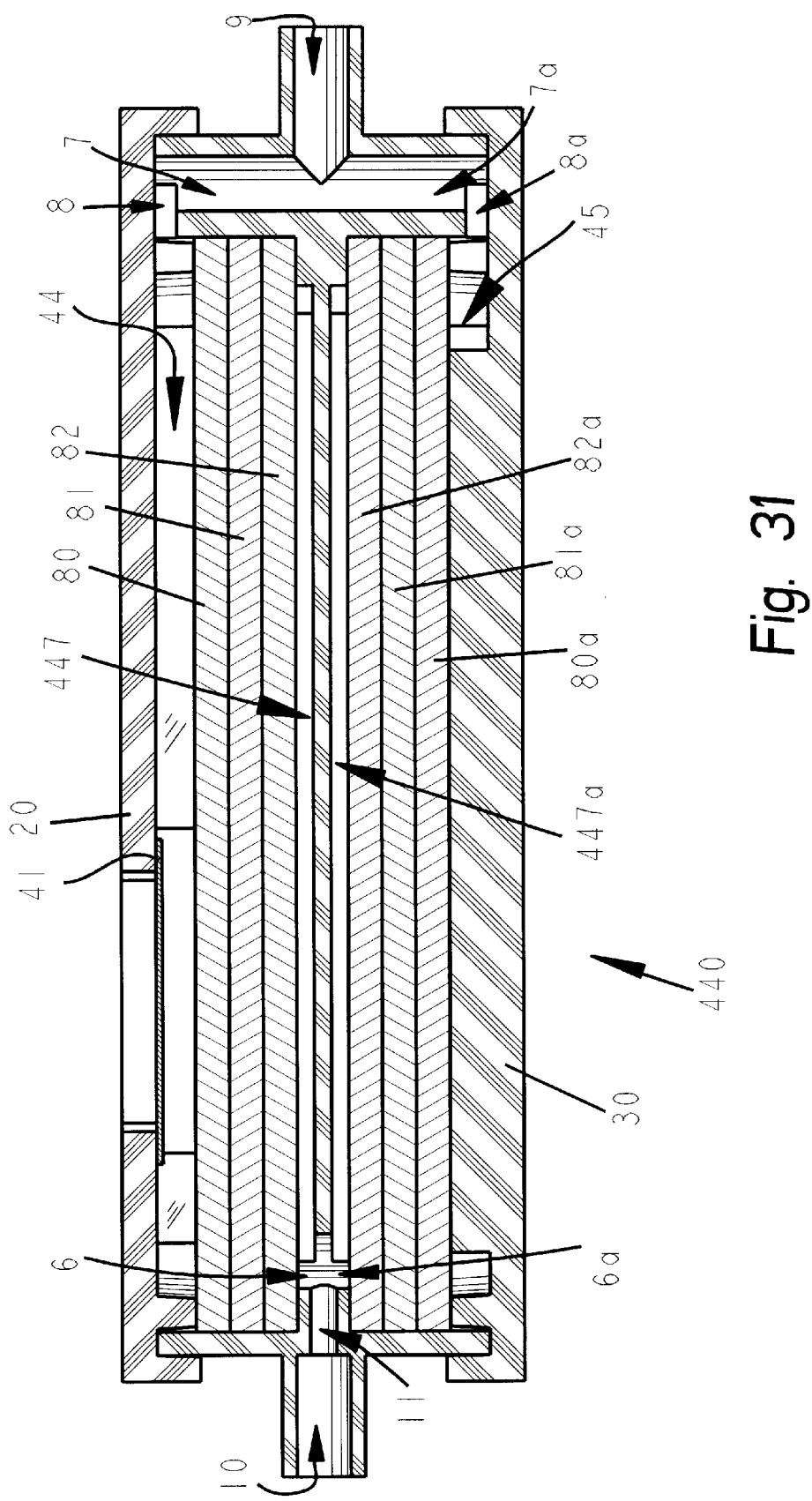
FIG. 31 is a cross-sectional view of the filtration apparatus depicted in FIG. 30.

Referring to FIG. 4B, FIG. 30, and FIG. 31, the assembled filter device 440 contains first chamber 44 of first filter well 13 bounded by flat surface 23 of front cover 20, inner surface 77 of round rib 25 of front cover 20, and the upstream surface 46 of the first filter element 80 in first filter well 13 of body 401. Referring to FIG. 5B, FIG. 30, and FIG. 31, the assembled filter device 440 also contains first chamber 45 of second filter well 13a bounded by flat surface 33 of back cover 30, inner surface 71 of round rib 35 of back cover 30, and the upstream surface 46a of the first filter element 80a in second filter well 13a of body 401. Referring to FIG. 3A and FIG. 31, in the assembled filter device 440, front inlet channel 8 becomes a closed channel bounded by side walls 15 and wall 16 of body 401, and by flat surface 23 of front cover 20. Referring to FIG. 31, front inlet channel 8 places first chamber 44 in fluid flow communication, and in air flow communication with front cross port 7. Referring to FIG. 3B and FIG. 31, in the assembled filter device 440, back inlet channel 8a becomes a closed channel bounded by side walls 15a and wall 16a of body 401, and by flat surface 33 of back cover 30. Referring to FIG. 31, back inlet channel 8a places first chamber 45 in fluid flow communication, and in air flow communication with back cross port 7a.

Referring to FIG. 28a, FIG. 29, FIG. 30 and FIG. 31, the assembled filter device 440 contains second chamber 447 of first filter well 13 bounded by the downstream surface 48 of the last filter element 82 in first filter well 13 of body 401, and by well 469. Second chamber 447 of first filter well 13 contains vertical channel 487, vertical filter support ribs 499, vertical filter support ribs 498, and front outlet port 6. As shown in FIG. 28a and FIG. 29, the portion of well 469 outside of vertical channel 487 is an open well with a pattern of vertical filter support ribs 498 protruding from flat surface 489. The space between vertical filter support ribs 498 should be small enough to provide the proper support for filter elements 80, 81, and 82, but large enough to allow gas, or gas bubbles in liquid to freely flow vertically through second chamber 447, between vertical filter support ribs 498. Furthermore, the height of vertical filter support ribs 498 and 499 should be high enough to allow gas, or gas bubbles in liquid to freely flow vertically through second chamber 447, between vertical filter support ribs 498. Referring to FIG. 28b, FIG. 30 and FIG. 31, the assembled filter device 440 contains second chamber 447a of second filter well 13a bounded by the downstream surface 48a of the last filter element 82a in second filter well 13a of body 401, and by well 469a. Second chamber 447a of second filter well 13a contains vertical channel 487a, vertical filter support ribs 499a, vertical filter support ribs 498a, and back outlet port 6a. As shown in FIG. 28b the portion of well 469a outside of vertical channel 487a is an open well with a pattern of vertical filter support ribs 498a protruding from flat surface 489a. The space between vertical filter support ribs 498a should be small enough to provide the proper support for filter elements 80, 81, and 82, but large enough to allow gas, or gas bubbles in liquid to freely flow vertically through second chamber 447a, between vertical filter support ribs 498a. Furthermore, the height of vertical filter support ribs 498 and 499 should be high enough to allow gas, or gas bubbles in liquid to freely flow vertically through second chamber 447, between vertical filter support ribs 498.

Filter device 440 could replace filter device 40 of assembly 60 shown in FIG. 9. Referring to FIG. 28A, FIG. 4B, FIG. 5B, FIG. 9, and FIG. 31 the filtration with filter device 440 replacing filter device 40 in FIG. 9 is performed as follows. The user opens inlet tube clamp 74. Gravity now forces blood to flow from feed blood bag 54, through inlet tubing 52, through inlet port 9 of body 401. After passing through inlet port 9, a portion of the blood passes through front cross port 7, while the remainder of the blood passes through back cross port 7a. The portion of the blood that passes through front cross port 7, then passes through front inlet channel 8, through gap 26 of front cover 20, into first chamber 44 of filter device 440. The portion of the blood that passes through back cross port 7a, then passes through back inlet channel 8a, through gap 36 of back cover 30, into first chamber 45 of filter device 440. A portion of the air that was in inlet tubing 52 and inlet port 9 before blood flow started will be pushed ahead of the blood, through front cross port 7, through front inlet channel 8, through gap 26 of front cover 20, into first chamber 44 of filter device 440. The remainder of the air that was in inlet tubing 52 and inlet port 9 before blood flow started will be pushed ahead of the blood, through back cross port 7a, through back inlet channel 8a, through gap 36 of back cover 30, into first chamber 45 of filter device 440. Because the usable surface area of hydrophobic filter 41 is much smaller than the usable surface area of filter elements 80, 81, and 82; and because the pressure drop across sterilizing grade hydrophobic filter 41 is much greater per unit volume of air flow per unit surface area of filter material than the combined pressure drop across filter elements 80, 81, and 82 per unit volume of air flow per unit surface area of filter material, only a very small portion of the air that was in inlet tubing 52, inlet port 9, front cross port 7, and front inlet channel 8 before blood flow started, will pass through hydrophobic filter 41, and then through slots 21 of front cover 20 to atmosphere. Therefore, most of the air that is forced into first chamber 44 by blood flow from the blood bag, and most of the air that was initially in first chamber 44 will be forced by the positive pressure (due to the blood flow) in first chamber 44, through filter elements 80, 81, and 82, into second chamber 447, through vertical channel 487, through front outlet port 6, through link port 11, through outlet port 10, through outlet tubing 53, into receiving blood bag 55; and all of the air that is forced into first chamber 45 by blood flow from the blood bag, and all of the air that was initially in first chamber 45 will be forced by the positive pressure (due to the blood flow) in first chamber 45, through filter elements 80a, 81a, and 82a, into second chamber 447a, through vertical channel 487a, through back outlet port 6a, through link port 11, through outlet port 10, through outlet tubing 53, into receiving blood bag 55.

As first chamber 44 of filter device 440 fills from the bottom up most of the air in first chamber 44 will be forced (by the positive pressure in first chamber 44) through filter elements 80, 81, and 82, for the same reasons described in the previous paragraph. This initial air will flow into second chamber 447 of first filter well 13 of filter device 440. Second chamber 447 is a closed chamber bounded by flat surface 489 and side wall 488, both of partition wall 300 of body 401, and by downstream surface 48 of filter element 82. Second chamber 447 contains closed vertical channel 487, bound by flat surface 489 of partition wall 300 of body 401, the side walls of vertical filter support ribs 499 of body 401 adjacent to vertical channel 487, and by downstream surface 48 of filter element 82. The bottom of vertical channel 487 is in fluid flow relation to outlet port 10 via front outlet port 6 and link port 11. The top end of vertical channel 487 is open to the top portion of second chamber 447. The initial air that enters second chamber 447 from filter elements 80, 81, and 82 plus all of the initial air that was in second chamber 447 will be forced from second chamber 447, through vertical channel 487, through front outlet port 6, through link port 11 through outlet port 10, through outlet tubing 53, into receiving blood bag 55. Because the volume of first chamber 44 is small, and the flow rate of blood entering first chamber 44 is much greater than the initial flow rate of blood through filter elements 80, 81, and 82, first chamber 44 will fill in a very small fraction of the time that it takes to wet filter elements 80, 81, and 82. The pressure head at the bottom of first chamber 44 will be larger than the pressure head at the top of first chamber 44, because of the height difference between the top and bottom of first chamber 44. Therefore liquid will start to come through filter element 82 into second chamber 447 from the bottom up. As second chamber 447 fills from the bottom up with blood the remaining air in second chamber 447 will be forced from second chamber 447, through vertical channel 487, through front outlet port 6, through link port 11 through outlet port 10, through outlet tubing 53, into receiving blood bag 55. Because the total volume of second chamber 447 is small (to minimize holdup) second chamber 447 may fill with blood (from the bottom up) before the upper part of filter element 82 has wet with blood. Once second chamber 447 is filled with blood, the blood from the top of second chamber 447 will flow through vertical channel 487, through front outlet port 6, through link port 11 through outlet port 10, through outlet tubing 53, into receiving blood bag 55. Once blood starts to flow through outlet tubing 53 the pressure head at the top of vertical channel 487 will become negative. (The negative pressure head at the top of vertical channel 487 will reach its maximum negative value when the blood in outlet tubing reaches receiving blood bag 55). Any additional air that is forced through the filter elements into second chamber 447 by blood flowing through and wetting the top portion of the filter elements will bubble to the top of second chamber 447 (because of the buoyancy of air in the blood) and be sucked out of second chamber 447, through vertical channel 487, through front outlet port 6, through link port 11 through outlet port 10, through outlet tubing 53, into receiving blood bag 55, by the negative pressure at the top of vertical channel 487 (as long as blood flow continues). This assures that filter elements 80, 81, and 82 will completely wet, and that all of the air that was in first chamber 44, filter elements 80, 81, and 82, second chamber 447, front outlet port 6, link port 11, outlet port 10, and the interior of outlet tubing 53 will be forced into receiving blood bag 55.

As first chamber 45 of filter device 440 fills from the bottom up all of the air in first chamber 45 will be forced (by the positive pressure in first chamber 45) through filter elements 80a, 81a, and 82a, for the same reasons described in the previous paragraph. This initial air will flow into second chamber 447a of second filter well 13a of filter device 440. Second chamber 447a is a closed chamber bounded by flat surface 489a and side wall 488a, both of partition wall 300 of body 401, and by downstream surface 48a of filter element 82a. Second chamber 447a contains closed vertical channel 487a, bound by flat surface 489a of partition wall 300 of body 401, the side walls of vertical filter support ribs 499a of body 401 adjacent to vertical channel 487a, and by downstream surface 48a of filter element 82a. The bottom of vertical channel 487a is in fluid flow relation to outlet port 10 via back outlet port 6a and link port 11. The top end of vertical channel 487a is open to the top portion of second chamber 447a. The initial air that enters second chamber 447a from filter elements 80a, 81a, and 82a plus all of the initial air that was in second chamber 447a will be forced from second chamber 447a, through vertical channel 487a, through back outlet port 6a, through link port 11 through outlet port 10, through outlet tubing 53, into receiving blood bag 55. Because the volume of first chamber 45 is small, and the flow rate of blood entering first chamber 45 is much greater than the initial flow rate of blood through filter elements 80a, 81a, and 82a, first chamber 45 will fill in a very small fraction of the time that it takes to wet filter elements 80a, 81a, and 82a. The pressure head at the bottom of first chamber 45 will be larger than the pressure head at the top of first chamber 45, because of the height difference between the top and bottom of first chamber 45. Therefore liquid will start to come through filter element 82a into second chamber 447a from the bottom up. As second chamber 447a fills from the bottom up with blood the remaining air in second chamber 447a will be forced from second chamber 447a, through vertical channel 487a, through back outlet port 6a, through link port 11 through outlet port 10, through outlet tubing 53, into receiving blood bag 55. Because the total volume of second chamber 447a is small (to minimize holdup) second chamber 447a may fill with blood (from the bottom up) before the upper part of filter element 82a has wet with blood. Once second chamber 447a is filled with blood, the blood from the top of second chamber 447a will flow through vertical channel 487a, through back outlet port 6a, through link port 11 through outlet port 10, through outlet tubing 53, into receiving blood bag 55. Once blood starts to flow through outlet tubing 53 the pressure head at the top of vertical channel 487a will become negative. (The negative pressure at the top of vertical channel 487a will reach its maximum negative value when the blood in outlet tubing reaches receiving blood bag 55). Any additional air that is forced through the filter elements into second chamber 447a by blood flowing through and wetting the top portion of the filter elements will bubble to the top of second chamber 447a (because of the buoyancy of air in blood) and be sucked out of second chamber 447a, through vertical channel 487a, through back outlet port 6a, through link port 11 through outlet port 10, through outlet tubing 53, into receiving blood bag 55, by the negative pressure at the top of vertical channel 487a (as long as blood flow continues). This assures that filter elements 80a, 81a, and 82a will completely wet, and that all of the air that was in first chamber 45, filter elements 80a, 81a, and 82a, second chamber 447a, back outlet port 6a, link port 11, outlet port 10, and the interior of outlet tubing 53 will be forced into receiving blood bag 55.

Figures 32A, 32B:
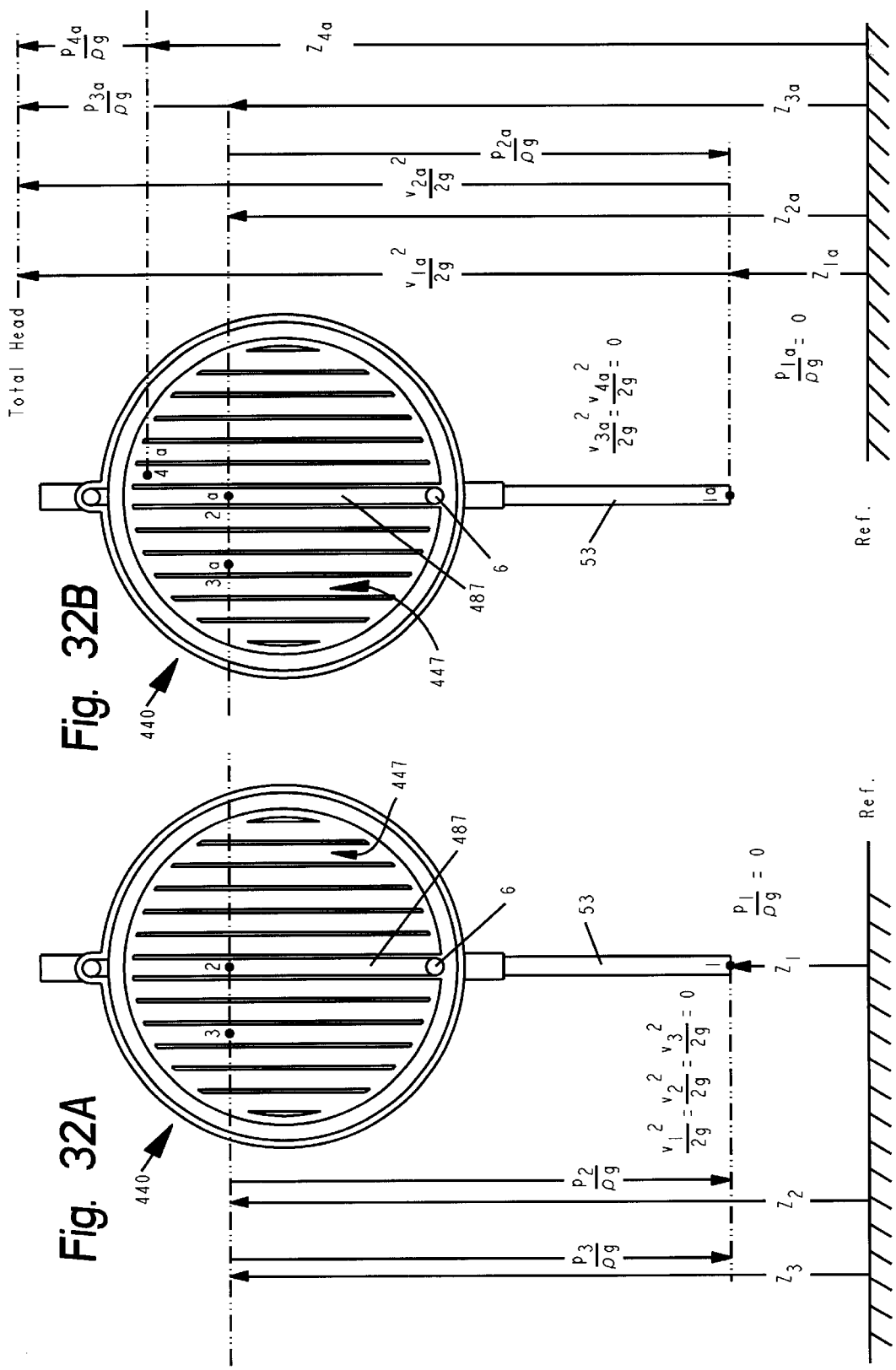
FIG. 32A is a schematic representation of the pressures in the downstream chamber of the filtration device depicted in FIG. 30, after the filtration device has been primed, for static conditions.
FIG. 32B is a schematic representation of the pressures in the downstream chamber of the filtration device depicted in FIG. 30, after the filtration device has been primed, for dynamic conditions.

FIG. 32A shows a schematic representation of second chamber 447 after the initial air that was in first chamber 44 and in second chamber 447 has been forced form chamber 447, through vertical channel 487, through front outlet port 6, through link port 11, through outlet port 10, through outlet tubing 53, into receiving blood bag 55; and after blood has filled second chamber 447, and at least a portion of the top of vertical channel 487, as explained above. FIG. 32A shows that the blood level has reached point 1 in outlet tubing 53. Because the receiving blood bag is surrounded by atmospheric pressure, point 1 is considered to be at atmospheric pressure. In FIG. 32A it is assumed that blood flow from the feed blood bag has been shut off, so that blood flow through filter elements 80, 81, and 82 has also stopped. Applying Bernoulli's equation to FIG. 32A, we have:

$$(v_1^2/2g)+(p_1/\rho g)+(z_1)=(v_2^2/2g)+(p_2/\rho g)+(z_2)=(v_3^2/2g)+(p_3/\rho g)+(z_3)$$

Where:

($v^2/2g$) is the velocity head ($p/\rho g$) is the pressure head z is the elevation head Because the blood bag is surrounded by atmospheric pressure:

$$(p_1/\rho g)=0$$

Because it is assumed that flow has stopped:

$$v_1=v_2=v_3=0$$

Therefore:

$$z_1=(z_2+(p_2/\rho g))=(z_3+(p_3/\rho g))$$

Therefore the pressure at any point on any horizontal line in second chamber 447 is equal to the pressure at any other point on the same horizontal line, as shown by points 2 and 3 in FIG. 32A. Because there is no pressure differential between point 2 inside of vertical channel 487 and point 3 outside of vertical channel 487, or between any other two points on any horizontal line in second chamber 447, any air that bubbles to the top of second chamber 447 because of the buoyancy of the air will not be sucked out of second chamber 447 into vertical channel 487 if there is no blood flow through the filter elements.

FIG. 32B shows a schematic representation of second chamber 447 after the initial air that was in first chamber 44 and in second chamber 447 has been forced form chamber 447, through vertical channel 487, through front outlet port 6, through link port 11, through outlet port 10, through outlet tubing 53, into receiving blood bag 55; and after blood has filled second chamber 447, and at least a portion of the top of vertical channel 487, as explained above. FIG. 32A shows that the blood level has reached point 1a in outlet tubing 53. Because the receiving blood bag is surrounded by atmospheric pressure, point 1a is considered to be at atmospheric pressure. In FIG. 32B it is assumed that blood is flowing from the feed blood bag, hence blood will also be flowing through filter elements 80, 81, and 82.

Applying Bernoulli's equation to FIG. 32B, we have:

$$(v_{1a}^2/2g)+(p_{1a}/\rho g)+(z_{1a})=(v_{2a}^2/2g)+(p_{2a}/\rho g)+(z_{2a})=(v_{3a}^2/2g)+(p_{3a}/\rho g)+(z_{3a})=(v_{4a}^2/2g)+(p_{4a}/\rho g)+(z_{4a})=\text{Total Head}$$

Because the blood bag is surrounded by atmospheric pressure:

$$(p_{1a}/\rho g)=0$$

Because all of the blood flow through filter elements 80, 81, and 82, must flow through vertical channel 487 and outlet tubing 53, the flow rate through vertical channel 487 and outlet tubing will be at least ten times the flow through any channel between adjacent pairs of vertical filter support ribs outside of vertical channel 487. Since the velocity head is proportional to the square of velocity it is assumed that the velocity head outside of vertical channel 487 equals zero, hence:

$$(v_{3a}^2/2g)=(v_{4a}^2/2g)=0$$

Therefore applying Bernoulli's equation to FIG. 32B, it can be seen that when blood flows through the filter elements because of a positive pressure on the upstream side of the filter elements, the head pressure inside of vertical channel 487 will be negative, with the maximum negative value at the top of vertical channel 487. It can also be seen that in a small region immediately outside of vertical channel 487 the head pressure will be negative, but less negative than the head pressure at the top of vertical channel 487. For all other points outside of vertical channel 487, inside of second chamber 447 the head pressure will be positive. Hence any air that is forced from the filter elements into second chamber 447 by blood flow through the filter will bubble to the top of second chamber 447 because of the buoyancy of the air in blood, and will then be sucked into vertical channel 487 because of the negative pressure head inside of vertical channel 487, and the positive pressure head outside of vertical channel 487. Both the forcing of air out of the filter elements into second chamber 447, and the sucking of the air out of the top of second chamber 447 into vertical channel 487, are dependent on blood flow through the filter elements, which is in turn dependent upon a positive pressure in first chamber 44. The positive pressure in first chamber 44 can be created by gravity flow from a reservoir positioned above chamber 44, or by any other source of positive pressure such as a pump.

Bernoulli's equation can be applied in the same way as above, for first chamber 45, filter elements 80a, 81a, 82a, and second chamber 447a.

In FIG. 32B it is assumed that the cross-sectional area of the vertical channel and that of the outlet tubing are equal. Therefore, the velocity head at point 2 equals the velocity head at point 1.

However, in FIG. 2, FIG. 11, and in FIG. 29, the cross-sectional area of the link port is shown smaller than that of the vertical channels of either the first filter well or the second filter well. Therefore, by applying Bernoulli's equation it can be seen that the maximum negative pressure will occur in the link port, not at the top of the vertical channel, because the velocity head will have its maximum value in the link port, and the total head at all points on the downstream side of the filter elements must be equal as described above. With the cross-sectional area of the link port less than that of the vertical channel, air that bubbles to the top of the second chamber will be sucked into the vertical channel as described above. Hence it can be seen that the link port, or the front outlet port, or the back outlet port, or the outlet port may have a cross-sectional area less than that of the vertical channel.

Blood filtration will continue until feed blood bag 54 is empty. When feed blood bag 54 is empty it will be collapsed and therefore close the inlet end of inlet tubing 52. Because outlet tubing 53 will be full of blood, and because the outside of receiving blood bag 55 is at atmospheric pressure, the pressure head in front outlet port 6, and the pressure head in back outlet port 6a will be negative, as will be the pressure head in second chamber 447, and second chamber 447a, all of body 401. Once blood flow has stopped the pressure drop across filter elements 80, 81, and 82, will fall to zero. The pressure drop across filter elements 80a, 81a, and 82a, will also fall to zero. Hence the pressure in first chamber 44 and first chamber 45 will become negative. Once the pressure in first chamber 44 falls below atmospheric pressure air will begin to flow from atmosphere through slots 21, through sterilizing grade hydrophobic filter 41, into first chamber 44. The sterile air that enters first chamber 44 will bubble up to the top of first chamber 44, thus causing first chamber 44 to drain from the top down. Because of the negative pressure in first chamber 45, some of the air that bubbles to the top of first chamber 44 will pass through gap 26, through front inlet channel 8, through front cross port 7, through back cross port 7a, through gap 36, through back inlet channel 8a, into first chamber 45, causing first chamber 45 to drain from the top down, and causing the blood in front inlet channel 8 to drain into first chamber 44, and causing the blood in back inlet channel 8a to drain into first chamber 45, and causing the blood in front cross port 7 and back cross port 7a to drain into both first chamber 44 and first chamber 45. Because the air entering first chamber 44 bubbles to the top of first chamber 44, thus draining first chamber 44 from the top down, vent filter element 41 can be located anywhere on flat surface 23 of front cover 20. Filter elements 80, 81, 82, 80a, 81a, and 82a will be plugged sufficiently at this point, therefore very little if any blood will be sucked from these filter elements by the negative pressure in second chamber 447, and by the negative pressure in second chamber 447a. Hence blood flow will stop after first chamber 44 and first chamber 45 have drained and blood will remain in filter elements 80, 81, 82, 80a, 81a, and 82a, in second chamber 447, in second chamber 447a, and in front outlet port 6, back outlet port 6a, link port 11, outlet port 10 all of body 401, and in outlet tubing 53.

The user can now close tube clamp 75 on outlet tubing 53 and then seal outlet tubing 53 above tube clamp 75, and then cut outlet tubing 53 above the seal just made. Feed blood bag 54, inlet tubing 52, and filter device 440 can now be discarded in a safe manner. Outlet tubing 53 will have segments marked on them. The user can now seal the tubing at the segment marks. The blood that is left in outlet tubing 53 will be used for cross matching and for quality control purposes.

Although the filter support means (including vertical channel 487) of second chamber 447 and the filter support means (including vertical channel 487a) of second chamber 447a are used in conjunction with the two sided filter device of the seventh embodiment of the present invention it will be appreciated by those skilled in the art that the same filter support means could be used with a single sided filter.

Body 101, and body 201, could also be modified to incorporate second chamber 447 of body 401, and second chamber 447a of body 401. Hence any of the embodiments from the first embodiment to the sixth embodiment could function like the seventh embodiment.

Although the present invention has been shown and described in terms of specific preferred embodiments, it will be appreciated by those skilled in the art that changes or modifications are possible which do not depart from the inventive concepts described and taught herein. Such changes and modifications are deemed to fall within the purview of these inventive concepts. In addition it is contemplated that the filter assembly may be employed in an environment other than blood filtration. A fluid system in which components of the fluid must be removed can benefit from the use of a filter apparatus embodying the teachings of the present invention.

What is claimed is:

1. A filter device for filtering blood or blood product to remove components of the blood or blood product from the blood or blood product comprising:

a body having a substantially vertical partition wall fixed to the inner periphery of said body, said partition wall dividing said body into a first filter well on one side of said partition wall, and a second filter well on the other side of said partition wall, with the central axis of both said first and said second filter wells oriented substantially horizontal, at least one filter element disposed within said first filter well, thereby dividing said first filter well into a first chamber upstream of said at least one filter element disposed in said first filter well, and a second chamber downstream of said at least one filter element disposed in said first filter well, said at least one filter element sealed to said first filter well, to prevent unfiltered blood or blood product from flowing between said first filter well and said at least one filter element disposed in said first filter well, at least one filter element disposed within said second filter well, thereby dividing said second filter well into a first chamber upstream of said at least one filter element disposed in said second filter well, and a second chamber downstream of said at least one filter element disposed in said second filter well, said at least one filter element sealed to said second filter well, to prevent unfiltered blood or blood product from flowing between said second filter well and said at least one filter element disposed in said second filter well, a cross port located on said body and entirely outside of said first filter well and said second filter well, with the central axis of said cross port oriented substantially parallel to the central axis of said first filter well and said second filter well, an inlet port located entirely outside of said first filter well and said second filter well, with one end of said inlet port adjoining and in direct fluid flow communication with a portion of said cross port, thereby dividing said cross port into a front cross port between the intersection of said inlet port and one end of said cross port, and a back cross port between the intersection of said inlet port and the opposite end of said cross port, a front inlet channel extending from said front cross port into said first filter well, thereby placing said front cross port in fluid flow communication with said first chamber of said first filter well, a back inlet channel extending from said back cross port into said second filter well, thereby placing said back cross port in fluid flow communication with said first chamber of said second filter well, a front cover sealed with a first seal to said body, said first seal forming a single closed loop that encloses the outer periphery of said first filter well and the outer periphery of said front inlet channel, thereby creating a closed first chamber in said first filter well, and a closed front inlet channel that extends from said front cross port to said first chamber of said first filter well, thereby creating a flow path from said inlet port, through said front cross port, through said front inlet channel, into said first chamber of said first filter well, a back cover sealed with a second seal to said body, said second seal forming a single closed loop that encloses the outer periphery of said second filter well and the outer periphery of said back inlet channel, thereby creating a closed first chamber in said second filter well, and a closed back inlet channel that extends from said back cross port to said first chamber of said second filter well, thereby creating a flow path from said inlet port, through said back cross port, through said back inlet channel, into said first chamber of said second filter well, an outlet port located below said second chamber of said first filter well, and below said second chamber of said second filter well, said outlet port in fluid flow communication with said second chamber of said first filter well, and in fluid flow communication with said second chamber of said second filter well.

2. The filter device of claim 1 wherein a front outlet port is interposed between said second chamber of said first filter well and said outlet port, thereby creating a flow path from said second chamber of said first filter well, through said front outlet port, into said outlet port, and wherein a back outlet port is interposed between said second chamber of said second filter well and said outlet port, thereby creating a flow path from said second chamber of said second filter well, through said back outlet port, into said outlet port.

3. The filter device of claim 2 wherein said second chamber of said first filter well contains a first closed bottom, open top substantially vertical channel, the cross sectional area of said first substantially vertical channel defined by the inner surface of said first substantially vertical channel, and by the downstream surface of the at least one filter element in said first filter well, with the open top of said first substantially vertical channel disposed adjacent the top of said second chamber of said first filter well, and with said front outlet port located within and adjacent the bottom of said first substantially vertical channel of said first filter well, and wherein said second chamber of said second filter well contains a second closed bottom, open top substantially vertical channel, the cross sectional area of said second substantially vertical channel defined by the inner surface of said second substantially vertical channel, and by the downstream surface of the at least one filter element in said second filter well, with the open top of said second substantially vertical channel disposed adjacent the top of said second chamber of said second filter well, and with said back outlet port located within and adjacent the bottom of said second substantially vertical channel of said second filter well.

4. The filter device of claim 3 wherein the top of said first closed bottom, open top substantially vertical channel of said first filter well is in direct fluid flow communication with said second chamber of said first filter well, and wherein the top of said first closed bottom, open top substantially vertical channel of said second filter well is in direct fluid flow communication with said second chamber of said second filter well.

5. The filter device of claim 4 wherein the portion of said second chamber of said first filter well outside of said first substantially vertical channel is an open chamber, and wherein the portion of said second chamber of said second filter well outside of said second substantially vertical channel is an open chamber.

6. The filter device of claim 1 wherein said at least one filter element of said first filter well is sealed to said first filter well by a compression fit between the outer edge of said at least one filter element and the inner periphery of said first filter well, and wherein said at least one filter element of said second filter well is sealed to said second filter well by a compression fit between the outer edge of said at least one filter element and the inner periphery of said second filter well.

7. The filter device of claim 1 wherein said at least one filter element of said first filter well is sealed to said first filter well by compressing the outer periphery of said at least one filter element of said first filter well between a first filter compression ring disposed in said first chamber of said first filter well, and the outer periphery of said second chamber of said first filter well, and wherein said at least one filter element of said second filter well is sealed to said second filter well by compressing the outer periphery of said at least one filter element of said second filter well between a second filter compression ring disposed in said first chamber of said second filter well, and the outer periphery of said second chamber of said second filter well.

8. The filter device of claim 7 wherein said first filter compression ring is an integral part of said front cover, and wherein said second filter compression ring is an integral part of said back cover.

9. The filter device of claim 7 wherein said first filter compression ring forms a closed loop, and wherein said second filter compression ring forms a closed loop.

10. The filter device of claim 9 wherein said first filter compression ring is press fitted into said first filter well, and wherein said second filter compression ring is press fitted into said second filter well.

11. The filter device of claim 10 wherein said first filter compression ring contains one or more notches, and wherein said second filter compression ring contains one or more notches.

12. The filter device of claim 1 wherein said front cover contains at least one opening between said first chamber of said first filter well and atmosphere, and
wherein a hydrophobic vent filter is sealed to said front cover, the inner periphery of said seal enclosing said at least one opening, thereby preventing the flow of unfiltered blood or blood product, or air between said vent filter and said body.

13. The filter device of claim 1 wherein said at least one filter element in said first filter well, and said at least one filter element in said second filter well are capable of removing leukocytes from blood or blood product.

14. A filter device for filtering blood or blood product to remove components of the blood or blood product from the blood or blood product comprising:
a body having a substantially vertical partition wall fixed to the inner periphery of said body, said partition wall dividing said body into a first filter well on one side of said partition wall, and a second filter well on the other side of said partition wall, with the central axis of both said first and said second filter wells oriented substantially horizontal,
at least one filter element disposed within said first filter well, thereby dividing said first filter well into a first chamber upstream of said at least one filter element disposed in said first filter well, and a second chamber downstream of said at least one filter element disposed in said first filter well, said at least one filter element sealed to said first filter well, to prevent un-filtered blood or blood product from flowing between said first filter well and said at least one filter element disposed in said first filter well,
at least one filter element disposed within said second filter well, thereby dividing said second filter well into a first chamber upstream of said at least one filter element disposed in said second filter well, and a second chamber downstream of said at least one filter element disposed in said second filter well, said at least one filter element sealed to said second filter well, to prevent unfiltered blood or blood product from flowing between said second filter well and said at least one filter element disposed in said second filter well,
a cross port located on said body and entirely outside of said first filter well and said second filter well, with the central axis of said cross port oriented substantially parallel to the central axis of said first filter well and said second filter well,
an inlet port located entirely outside of said first filter well and said second filter well, with one end of said inlet port adjoining and in direct fluid flow communication with a portion of said cross port, thereby dividing said cross port into a front cross port between the intersection of said inlet port and one end of said cross port, and a back cross port between the intersection of said inlet port and the opposite end of said cross port,
a front cover sealed with a first seal to said body, said front cover containing a first port with the central axis of said first port substantially aligned with the central axis of said front cross port, and with the first end of said first port adjoining said front cross port and in fluid flow communication with said front cross port, said front cover further containing a second port with the central axis of said second port being substantially perpendicular to the central axis of said first port, with the first end of said second port adjoining and in fluid flow communication with the second end of said first port, and with the second end of said second port in fluid flow communication with said first chamber of said first filter well, with said first seal forming a double closed loop, said double closed loop containing a first closed loop that encloses the outer periphery of said first filter well, thereby creating a closed first chamber in said first filter well, said double closed loop further containing a second closed loop that encloses the outer periphery of said front cross port, and the outer periphery of said first port, thereby creating a flow path from said inlet port, through said front cross port, through said first port, through said second port, into said first chamber of said first filter well,
a back cover sealed with a second seal to said body, said back cover containing a third port with the central axis of said third port substantially aligned with the central axis of said back cross port, and with the first end of said third port adjoining said back cross port and in fluid flow communication with said back cross port, said back cover further containing a fourth port with the central axis of said fourth port being substantially perpendicular to the central axis of said third port, with the first end of said fourth port adjoining and in fluid flow communication with the second end of said third port, and with the second end of said fourth port in fluid flow communication with said first chamber of said second filter well, with said second seal forming a double closed loop, said double closed loop containing a first closed loop that encloses the outer periphery of said second filter well, thereby creating a closed first chamber in said second filter well, said double closed loop further containing a second closed loop that encloses the outer periphery of said back cross port, and the outer periphery of said third port, thereby creating a flow path from said inlet port, through said back cross port, through said third port, through said fourth port, into said first chamber of said second filter well,
an outlet port located below said second chamber of said first filter well, and below said second chamber of said second filter well, said outlet port in fluid flow communication with said second chamber of said first filter well, and in fluid flow communication with said second chamber of said second filter well.

15. The filter device of claim 14 wherein a front outlet port is interposed between said second chamber of said first filter well and said outlet port, thereby creating a flow path from said second chamber of said first filter well, through said front outlet port, into said outlet port, and
wherein a back outlet port is interposed between said second chamber of said second filter well and said outlet port, thereby creating a flow path from said second chamber of said second filter well, through said back outlet port, into said outlet port.

16. The filter device of claim 15 wherein said second chamber of said first filter well contains a first closed bottom, open top substantially vertical channel, the cross sectional area of said first substantially vertical channel defined by the inner surface of said first substantially vertical channel, and by the downstream surface of the at least one filter element in said first filter well, with the open top of said first substantially vertical channel disposed adjacent the top of said second chamber of said first filter well, and with said front outlet port located within and adjacent the bottom of said first substantially vertical channel of said first filter well, and wherein said second chamber of said second filter well contains a second closed bottom, open top substantially vertical channel, the cross sectional area of said second substantially vertical channel defined by the inner surface of said second substantially vertical channel, and by the downstream surface of the at least one filter element in said second filter well, with the open top of said second substantially vertical channel disposed adjacent the top of said second chamber of said'second filter well, and with said back outlet port located within and adjacent the bottom of said second substantially vertical channel of said second filter well.

17. The filter device of claim 16 wherein the top of the first closed bottom, open top substantially vertical channel of said first filter well is in direct fluid flow communication with said second chamber of said first filter well, and wherein the top of second closed bottom, open top substantially vertical channel of said second filter well is in direct fluid flow communication with said second chamber of said second filter well.

18. The filter device of claim 17 wherein the portion of said second chamber of said first filter well outside of said first substantially vertical channel is an open chamber, and wherein the portion of said second chamber of said second filter well outside of said second substantially vertical channel is an open chamber.

19. The filter device of claim 14 wherein said at least one filter element of said first filter well is sealed to said first filter well by a compression fit between the outer edge of said at least one filter element and the inner periphery of said first filter well, and wherein said at least one filter element of said second filter well is sealed to said second filter well by a compression fit between the outer edge of said at least one filter element and the inner periphery of said second filter well.

20. The filter device of claim 14 wherein said at least one filter element of said first filter well is sealed to said first filter well by compressing the outer periphery of said at least one filter element of said first filter well between a first filter compression ring disposed in said first chamber of said first filter well, and the outer periphery of said second chamber of said first filter well, and wherein said at least one filter element of said second filter well is sealed to said second filter well by compressing the outer periphery of said at least one filter element of said second filter well between a second filter compression ring disposed in said first chamber of said second filter well, and the outer periphery of said second chamber of said second filter well.

21. The filter device of claim 20 wherein said first filter compression ring is an integral part of said front cover, and wherein said second filter compression ring is an integral part of said back cover.

22. The filter device of claim 21 wherein said first filter compression ring forms a closed loop, and wherein said second filter compression ring forms a closed loop.

23. The filter device of claim 20 wherein said first filter compression ring is press fitted into said first filter well, and wherein said second filter compression ring is press fitted into said second filter well.

24. The filter device of claim 14 wherein said front cover contains at least one opening between said first chamber of said first filter well and atmosphere, and wherein a hydrophobic vent filter is sealed to said front cover, the inner periphery of said seal enclosing said at least one opening, thereby preventing the flow of unfiltered blood or blood product, or air between said vent filter and said body.

25. The filter device of claim 14 wherein said at least one filter element in said first filter well, and said at least one filter element in said second filter well are capable of removing leukocytes from blood or blood product.

26. A method for processing blood or blood product comprising:

1) providing a filter device for filtering blood or blood product to remove components of the blood or blood product from the blood or blood product comprising:

a body having a substantially vertical partition wall fixed to the inner periphery of said body, said partition wall dividing said body into a first filter well on one side of said partition wall, and a second filter well on the other side of said partition wall, with the central axis of both said first and said second filter wells oriented substantially horizontal, at least one filter element disposed within said first filter well, thereby dividing said first filter well into a first chamber, and a second chamber, said at least one filter element sealed to said first filter well, to prevent unfiltered blood or blood product from flowing between said first filter well and said at least one filter element disposed in said first filter well, at least one filter element disposed within said second filter well, thereby dividing said second filter well into a first chamber, and a second chamber, said at least one filter element sealed to said second filter well, to prevent unfiltered blood or blood product from flowing between said second filter well and said at least one filter element disposed in said second filter well, an inlet port, said inlet port located above said first chamber of said first filter well, and above said first chamber of said second filter well, a cross port located below said inlet port, with the central axis of said cross port substantially parallel to the central axis of said first filter well, and substantially parallel to the central axis of said second filter well, said cross port placing said inlet port in fluid flow communication with said first chamber of said first filter well, and in fluid flow communication with said first chamber of said second filter well, an outlet port, said outlet port located at a level equal to or below the bottom of said second chamber of said first filter well, and at a level equal to or below the bottom of said second chamber of said second filter well, a means to place said outlet port in fluid flow communication with said second chamber of said first filter well, and in fluid flow communication with said second chamber of said second filter well, with said second chamber of said first filter well containing a first closed bottom, open top substantially vertical channel, the cross sectional area of said first substantially vertical channel defined by the inner surface of said first substantially vertical channel, and by the downstream surface of the at least one filter element in said first filter well, with the open top of said first substantially vertical channel disposed adjacent the top of said second chamber of said first filter well and in direct fluid flow communication with said second chamber of said first filter well, and with the bottom portion of said first substantially vertical channel in fluid flow communication with said outlet port, and with said second chamber of said second filter well containing a second closed bottom, open top substantially vertical channel, the cross sectional area of said second substantially vertical channel defined by the inner surface of said second substantially vertical channel, and by the downstream surface of the at least one filter element in said second filter well, with the open top of said second substantially vertical channel disposed adjacent the top of said second chamber of said second filter well and in direct fluid flow communication with said second chamber of said second filter well, and with the bottom portion of said second substantially vertical channel in fluid flow communication with said outlet port, 2) flowing unfiltered blood or blood product into the inlet port of said filter device, 3) flowing a first portion of said unfiltered blood or blood product from said inlet port, through said cross port, into said first chamber of said first filter well, filtering said first portion of blood or blood product through said at least one filter element of said first filter well, flowing the first portion of filtered blood or blood product into said second chamber of said first filter well, and then into said outlet port, 4) flowing a second portion of said unfiltered blood or blood product from said inlet port, through said cross port, into said first chamber of said second filter well, filtering said second portion of blood or blood product through said at least one filter element of said second filter well, flowing the second portion of filtered blood or blood product into said second chamber of said second filter well, and then into said outlet port.

27. A method for processing blood or blood product comprising:

1) providing a filter device for filtering blood or blood product to remove components of the blood or blood product from the blood or blood product comprising:

a body having a substantially vertical partition wall fixed to the inner periphery of said body, said partition wall dividing said body into a first filter well on one side of said partition wall, and a second filter well on the other side of said partition wall, with the central axis of both said first and said second filter wells oriented substantially horizontal, at least one filter element disposed within said first filter well, thereby dividing said first filter well into a first chamber, and a second chamber, said at least one filter element sealed to said first filter well, to prevent unfiltered blood or blood product from flowing between said first filter well and said at least one filter element disposed in said first filter well, at least one filter element disposed within said second filter well, thereby dividing said second filter well into a first chamber, and a second chamber, said at least one filter element sealed to said second filter well, to prevent unfiltered blood or blood product from flowing between said second filter well and said at least one filter element disposed in said second filter well, with said at least one filter element of said first filter well sealed to said first filter well by compressing the outer periphery of said at least one filter element of said first filter well between a filter compression ring disposed in said first chamber of said first filter well, and the outer periphery of said second chamber of said first filter well, and with said at least one filter element of said second filter well is sealed to said second filter well by compressing the outer periphery of said at least one filter element of said second filter well between a filter compression ring disposed in said first chamber of said second filter well, and the outer periphery of said second chamber of said second filter well, an inlet port, said inlet port located above said first chamber of said first filter well, and above said first chamber of said second filter well, a cross port located below said inlet port, with the central axis of said cross port substantially parallel to the central axis of said first filter well, and substantially parallel to the central axis of said second filter well, said cross port placing said inlet port in fluid flow communication with said first chamber of said first filter well, and in fluid flow communication with said first chamber of said second filter well, an outlet port, a means to place said outlet port in fluid flow communication with said second chamber of said first filter well, and in fluid flow communication with said second chamber of said second filter well, with said body further containing a front cover, the outer periphery of said front cover sealed to the outer periphery of said first filter well, and to the outer periphery of the portion of said cross port in fluid flow communication with said first chamber of said first filter well, and with said body containing a back cover, the outer periphery of said back cover sealed to the outer periphery of said second filter well, and to the outer periphery of the portion of said cross port in fluid flow communication with said first chamber of said second filter well, 2) flowing unfiltered blood or blood product into the inlet port of said filter device, 3) flowing a first portion of said unfiltered blood or blood product from said inlet port, through said cross port, into said first chamber of said first filter well, filtering said first portion of blood or blood product through said at least one filter element of said first filter well, flowing the first portion of filtered blood or blood product into said second chamber of said first filter well, and then into said outlet port, 4) flowing a second portion of said unfiltered blood or blood product from said inlet port, through said cross port, into said first chamber of said second filter well, filtering said second portion of blood or blood product through said at least one filter element of said second filter well, flowing the second portion of filtered blood or blood product into said second chamber of said second filter well, and then into said outlet port.

28. A method for processing blood or blood product comprising:

1) providing a filter device for filtering blood or blood product to remove components of the blood or blood product from the blood or blood product comprising:

a body having a substantially vertical partition wall fixed to the inner periphery of said body, said partition wall dividing said body into a first filter well on one side of said partition wall, and a second filter well on the other side of said partition wall, with the central axis of both said first and said second filter wells oriented substantially horizontal, at least one filter element disposed within said first filter well, thereby dividing said first filter well into a first chamber upstream of said at least one filter element disposed in said first filter well, and a second chamber downstream of said at least one filter element disposed in said first filter well, said at least one filter element sealed to said first filter well, to prevent unfiltered blood or blood product from flowing between said first filter well and said at least one filter element disposed in said first filter well, at least one filter element disposed within said second filter well, thereby dividing said second filter well into a first chamber upstream of said at least one filter element disposed in said second filter well, and a second chamber downstream of said at least one filter element disposed in said second filter well, said at least one filter element sealed to said second filter well, to prevent unfiltered blood or blood product from flowing between said second filter well and said at least one filter element disposed in said second filter well, a cross port located on said body and entirely outside of said first filter well and said second filter well, with the central axis of said cross port oriented substantially parallel to the central axis of said first filter well and said second filter well, an inlet port located entirely outside of said first filter well and said second filter well, with one end of said inlet port adjoining and in direct fluid flow communication with a portion of said cross port, thereby dividing said cross port into a front cross port between the intersection of said inlet port and one end of said cross port, and a back cross port between the intersection of said inlet port and the opposite end of said cross port, a front inlet channel extending from said front cross port into said first filter well, thereby placing said front cross port in fluid flow communication with said first chamber of said first filter well, a back inlet channel extending from said back cross port into said second filter well, thereby placing said back cross port in fluid flow communication with said first chamber of said second filter well, a front cover sealed with a first seal to said body, said first seal forming a single closed loop that encloses the outer periphery of said first filter well and the outer periphery of said front inlet channel, thereby creating a closed first chamber in said first filter well, and a closed front inlet channel that extends from said front cross port to said first chamber of said first filter well, thereby creating a flow path from said inlet port, through said front cross port, through said front inlet channel, into said first chamber of said first filter well, a back cover sealed with a second seal to said body, said second seal forming a single closed loop that encloses the outer periphery of said second filter well and the outer periphery of said back inlet channel, thereby creating a closed first chamber in second filter well, and a closed back inlet channel that extends from said back cross port to said first chamber of said second filter well, thereby creating a flow path from said inlet port, through said back cross port, through said back inlet channel, into said first chamber of said second filter well, an outlet port located below said second chamber of said first filter well, and below said second chamber of said second filter well, with said outlet port in fluid flow communication with said second chamber of said first filter well, and in fluid flow communication with said second chamber of said second filter well, 2) flowing unfiltered blood or blood product into the inlet port of said filter device, 3) flowing a first portion of said un-filtered blood or blood product from said inlet port through said front cross port, through said front inlet channel, into said first chamber of said first filter well, filtering said first portion of blood or blood product through said at least one filter element of said first filter well, flowing the first portion of filtered blood or blood product into said second chamber of said first filter well, and then into said outlet port, 4) flowing a second portion of said unfiltered blood or blood product from said inlet port through said back cross port, through said back inlet channel, into said first chamber of said second filter well, filtering said second portion of blood or blood product through said at least one filter element of said second filter well, flowing the second portion of filtered blood or blood product into said second chamber of said second filter well, and then into said outlet port.

29. The method of claim 28 wherein said at least one filter element of said first filter well is sealed to said first filter well by a compression fit between the outer edge of said at least one filter element and the inner periphery of said first filter well, and wherein said at least one filter element of said second filter well is sealed to said second filter well by a compression fit between the outer edge of said at least one filter element and the inner periphery of said second filter well.

30. The method of claim 28 wherein said at least one filter element of said first filter well is sealed to said first filter well by compressing the outer periphery of said at least one filter element of said first filter well between a first filter compression ring disposed in said first chamber of said first filter well, and the outer periphery of said second chamber of said first filter well, and wherein said at least one filter element of said second filter well is sealed to said second filter well by compressing the outer periphery of said at least one filter element of said second filter well between a second filter compression ring disposed in said first chamber of said second filter well, and the outer periphery of said second chamber of said second filter well.

31. A method for processing blood or blood product comprising:

1) providing a filter device for filtering blood or blood product to remove components of the blood or blood product from the blood or blood product comprising:

a body having a substantially vertical partition wall fixed to the inner periphery of said body, said partition wall dividing said body into a first filter well on one side of said partition wall, and a second filter well on the other side of said partition wall, with the central axis of both said first and said second filter wells oriented substantially horizontal, at least one filter element disposed within said first filter well, thereby dividing said first filter well into a first chamber upstream of said at least one filter element disposed in said first filter well, and a second chamber downstream of said at least one filter element disposed in said first filter well, said at least one filter element sealed to said first filter well, to prevent unfiltered blood or blood product from flowing between said first filter well and said at least one filter element disposed in said first filter well, at least one filter element disposed within said second filter well, thereby dividing said second filter well into a first chamber upstream of said at least one filter element disposed in said second filter well, and a second chamber downstream of said at least one filter element disposed in said second filter well, said at least one filter element sealed to said second filter well, to prevent unfiltered blood or blood product from flowing between said second filter well and said at least one filter element disposed in said second filter well, a cross port located on said body and entirely outside of said first filter well and said second filter well, with the central axis of said cross port oriented substantially parallel to the central axis of said first filter well and said second filter well, an inlet port located entirely outside of said first filter well and said second filter well, with one end of said inlet port adjoining and in direct fluid flow communication with a portion of said cross port, thereby dividing said cross port into a front cross port between the intersection of said inlet port and one end of said cross port, and a back cross port between the intersection of said inlet port and the opposite end of said cross port, a front cover sealed with a first seal to said body, said front cover containing a first port with the central axis of said first port substantially aligned with the central axis of said front cross port, and with the first end of said first port adjoining said front cross port and in fluid flow communication with said front cross port, said front cover further containing a second port with the central axis of said second port being substantially perpendicular to the central axis of said first port, with the first end of said second port adjoining and in fluid flow communication with the second end of said first port, and with the second end of said second port in fluid flow communication with said first chamber of said first filter well, with said first seal forming a double closed loop, said double closed loop containing a first closed loop that encloses the outer periphery of said first filter well, thereby creating a closed first chamber in said first filter well, said double closed loop further containing a second closed loop that encloses the outer periphery of said front cross port, and the outer periphery of said first port, thereby creating a flow path from said inlet port, through said front cross port, through said first port, through said second port, into said first chamber of said first filter well, a back cover sealed with a second seal to said body, said back cover containing a third port with the central axis of said third port substantially aligned with the central axis of said back cross port, and with the first end of said third port adjoining said back cross port and in fluid flow communication with said back cross port, said back cover further containing a fourth port with the central axis of said fourth port being substantially perpendicular to the central axis of said third port, with the first end of said fourth port adjoining and in fluid flow communication with the second end of said third port, and with the second end of said fourth port in fluid flow communication with said first chamber of said second filter well, with said second seal forming a double closed loop, said double closed loop containing a first closed loop that encloses the outer periphery of said second filter well, thereby creating a closed first chamber in said second filter well, said double closed loop further containing a second closed loop that encloses the outer periphery of said back cross port, and the outer periphery of said third port, thereby creating a flow path from said inlet port, through said back cross port, through said third port, through said fourth port, into said first chamber of said second filter well, an outlet port located below said second chamber of said first filter well, and below said second chamber of said second filter well, with said outlet port in fluid flow communication with said second chamber of said first filter well, and in fluid flow communication with said second chamber of said second filter well, 2) flowing unfiltered blood or blood product into the inlet port of said filter device, 3) flowing a first portion of said unfiltered blood or blood product from said inlet port through said front cross port, through said first port, through said second port, into said first chamber of said first filter well, filtering said first portion of blood or blood product through said at least one filter element of said first filter well, flowing the first portion of filtered blood or blood product into said second chamber of said first filter well, and then into said outlet port, 4) flowing a second portion of said unfiltered blood or blood product from said inlet port through said back cross port, through said third port, through said fourth port, into said first chamber of said second filter well, filtering said second portion of blood or blood product through said at least one filter element of said second filter well, flowing the second portion of filtered blood or blood product into said second chamber of said second filter well, and then into said outlet port.

32. The method of claim 31 wherein said at least one filter element of said first filter well is sealed to said first filter well by a compression fit between the outer edge of said at least one filter element and the inner periphery of said first filter well, and wherein said at least one filter element of said second filter well is sealed to said second filter well by a compression fit between the outer edge of said at least one filter element and the inner periphery of said second filter well.

33. The method of claim 31 wherein said at least one filter element of said first filter well is sealed to said first filter well by compressing the outer periphery of said at least one filter element of said first filter well between a first filter compression ring disposed in said first chamber of said first filter well, and the outer periphery of said second chamber of said first filter well, and wherein said at least one filter element of said second filter well is sealed to said second filter well by compressing the outer periphery of said at least one filter element of said second filter well between a second filter compression ring disposed in said first chamber of said second filter well, and the outer periphery of said second chamber of said second filter well.

* * * * *